United States Patent
Arlett et al.

(10) Patent No.: US 11,027,281 B2
(45) Date of Patent: Jun. 8, 2021

(54) INSTRUMENT FOR PERFORMING A DIAGNOSTIC TEST ON A FLUIDIC CARTRIDGE

(71) Applicant: Atlas Genetics Limited, Trowbridge (GB)

(72) Inventors: Ben Arlett, Bristol (GB); Tom Edwards, Salisbury (GB)

(73) Assignee: Binx Health Limited, Trowbridge (GB)

( * ) Notice: Subject to any disclaimer, the term of this patent is extended or adjusted under 35 U.S.C. 154(b) by 404 days.

(21) Appl. No.: 15/547,875

(22) PCT Filed: Feb. 2, 2016

(86) PCT No.: PCT/GB2016/050234
§ 371 (c)(1),
(2) Date: Aug. 1, 2017

(87) PCT Pub. No.: WO2016/124908
PCT Pub. Date: Aug. 11, 2016

(65) Prior Publication Data
US 2018/0015475 A1 Jan. 18, 2018

(30) Foreign Application Priority Data
Feb. 2, 2015 (GB) ..................... 1501705

(51) Int. Cl.
*B01L 3/00* (2006.01)
*G01N 35/00* (2006.01)
(Continued)

(52) U.S. Cl.
CPC ......... *B01L 3/527* (2013.01); *B01L 3/502715* (2013.01); *B01L 7/52* (2013.01);
(Continued)

(58) Field of Classification Search
CPC ...................................................... B01L 3/527
(Continued)

(56) References Cited

U.S. PATENT DOCUMENTS

2013/0331298 A1   12/2013   Rea
2014/0206074 A1*  7/2014    Peterson ................. B01L 3/502
                                                435/287.2

FOREIGN PATENT DOCUMENTS

EP       3027317 A1     6/2016
WO   WO-9727324 A1     7/1997
(Continued)

OTHER PUBLICATIONS

Great Britain Search Report for Application No. GB 1501705.6 dated Nov. 22, 2015.
(Continued)

*Primary Examiner* — Holly Kipouros
(74) *Attorney, Agent, or Firm* — Brown Rudnick LLP; Thomas C. Meyers

(57) ABSTRACT

A cartridge reader controlled by processing means for carrying out a diagnostic test on a sample contained in a fluidic cartridge comprises a mechanical valve for isolating the sample with the cartridge. A system for actuating the mechanical valve comprises an actuation member configured to move the mechanical valve from an open position to a closed position and an armature connected to the actuation member. The armature is configured to engage an electromagnet, wherein the electromagnet can be switched between an active state in which it electromagnetically holds the armature and an inactive state in which it does not electromagnetically hold the armature. First biasing means are disposed between the actuation member and a bearing surface, wherein the first biasing means is configured to bias the actuation member into a first position in which it actuates (Continued)

a mechanical valve in a fluidic cartridge inserted into the reader.

10 Claims, 52 Drawing Sheets

(51) Int. Cl.
    *G01N 33/487*     (2006.01)
    *B01L 7/00*     (2006.01)
    *C12Q 1/686*     (2018.01)

(52) U.S. Cl.
    CPC .............. *B01L 7/525* (2013.01); *C12Q 1/686* (2013.01); *G01N 33/48785* (2013.01); *G01N 35/00029* (2013.01); *B01L 2200/025* (2013.01); *B01L 2200/04* (2013.01); *B01L 2200/10* (2013.01); *B01L 2200/146* (2013.01); *B01L 2200/16* (2013.01); *B01L 2300/0816* (2013.01); *B01L 2300/0867* (2013.01); *B01L 2300/0874* (2013.01); *B01L 2300/0887* (2013.01); *B01L 2300/123* (2013.01); *B01L 2300/1822* (2013.01); *B01L 2400/0478* (2013.01); *B01L 2400/0481* (2013.01); *B01L 2400/0487* (2013.01); *B01L 2400/0633* (2013.01); *B01L 2400/0666* (2013.01); *B01L 2400/0683* (2013.01); *G01N 2035/00128* (2013.01)

(58) Field of Classification Search
    USPC ........................................................ 422/63
    See application file for complete search history.

(56) References Cited

FOREIGN PATENT DOCUMENTS

| WO | 0073412 A2 | 12/2000 |
|----|----|----|
| WO | WO-0073412 A2 | 12/2000 |
| WO | WO-03074731 A2 | 9/2003 |
| WO | WO-2012085591 A1 | 6/2012 |
| WO | 2012178166 A1 | 12/2012 |
| WO | WO-2012178166 A1 | 12/2012 |
| WO | WO-2013190328 A1 | 12/2013 |

OTHER PUBLICATIONS

Hillier et al., An electrochemical study of enzymatic oligonucleotide digestion. Bioelectrochemistry. Jun. 2004;63(1-2):307-10.

Ihara et al., Ferrocene-oligonucleotide conjugates for electrochemical probing of DNA. Nucleic Acids Res. Nov. 1, 1996;24(21):4273-80.

International Search Report and Written Opinion for Application No. PCT/GB2016/050234 dated Apr. 28, 2016.

European Examination Report issued in European Application No. 16702799.4, dated Dec. 23, 2020, 6 pages.

\* cited by examiner

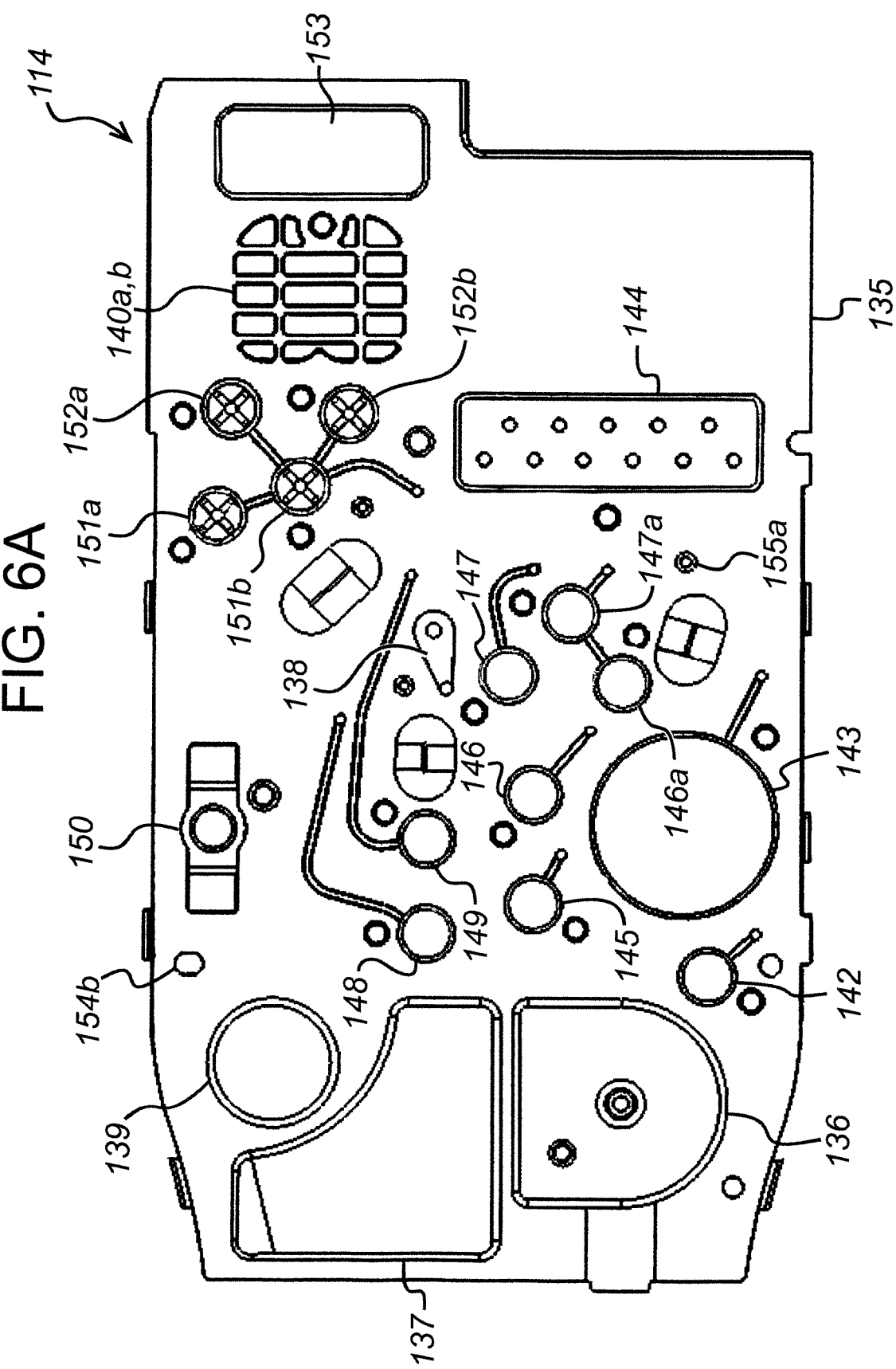

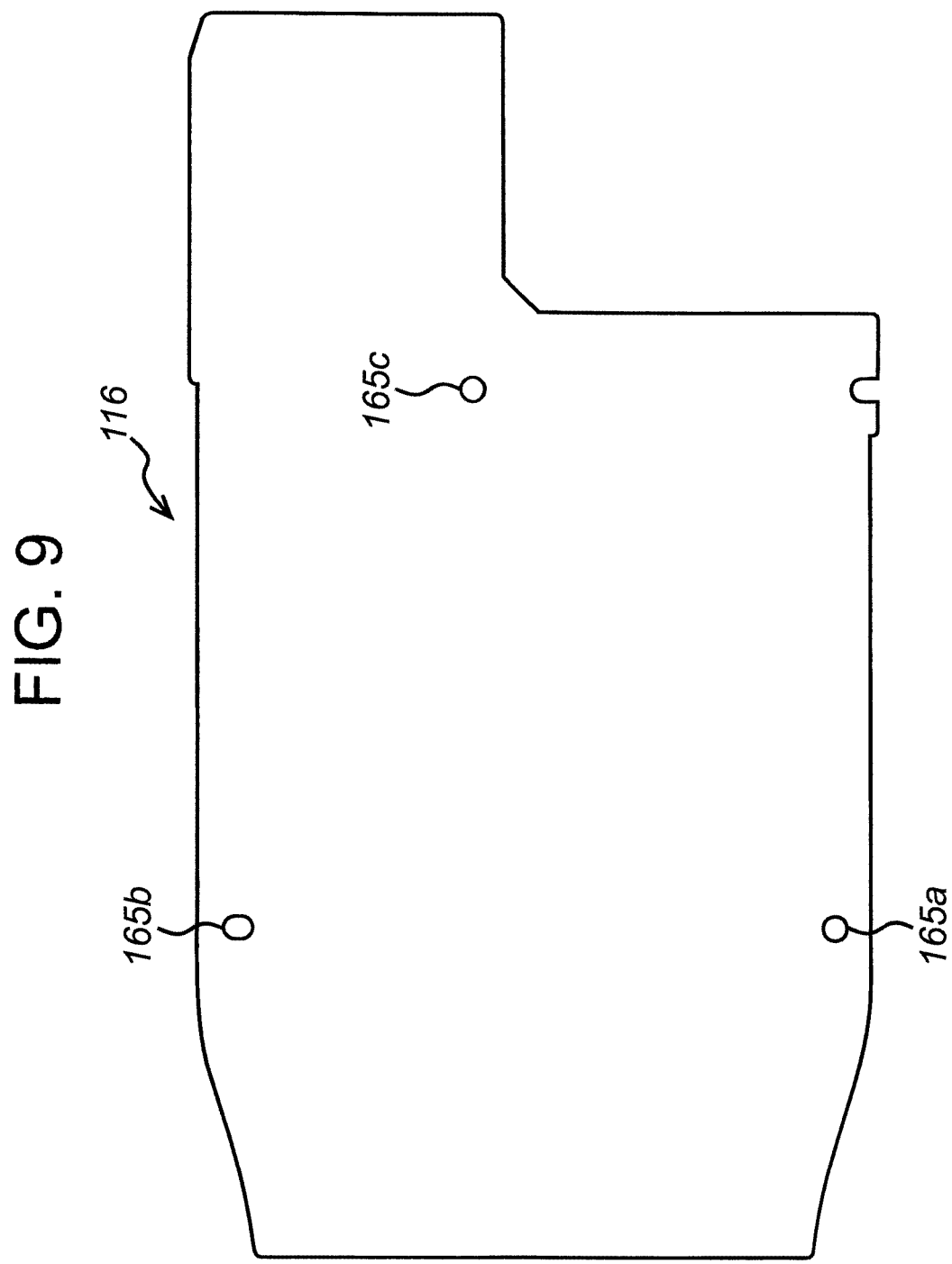

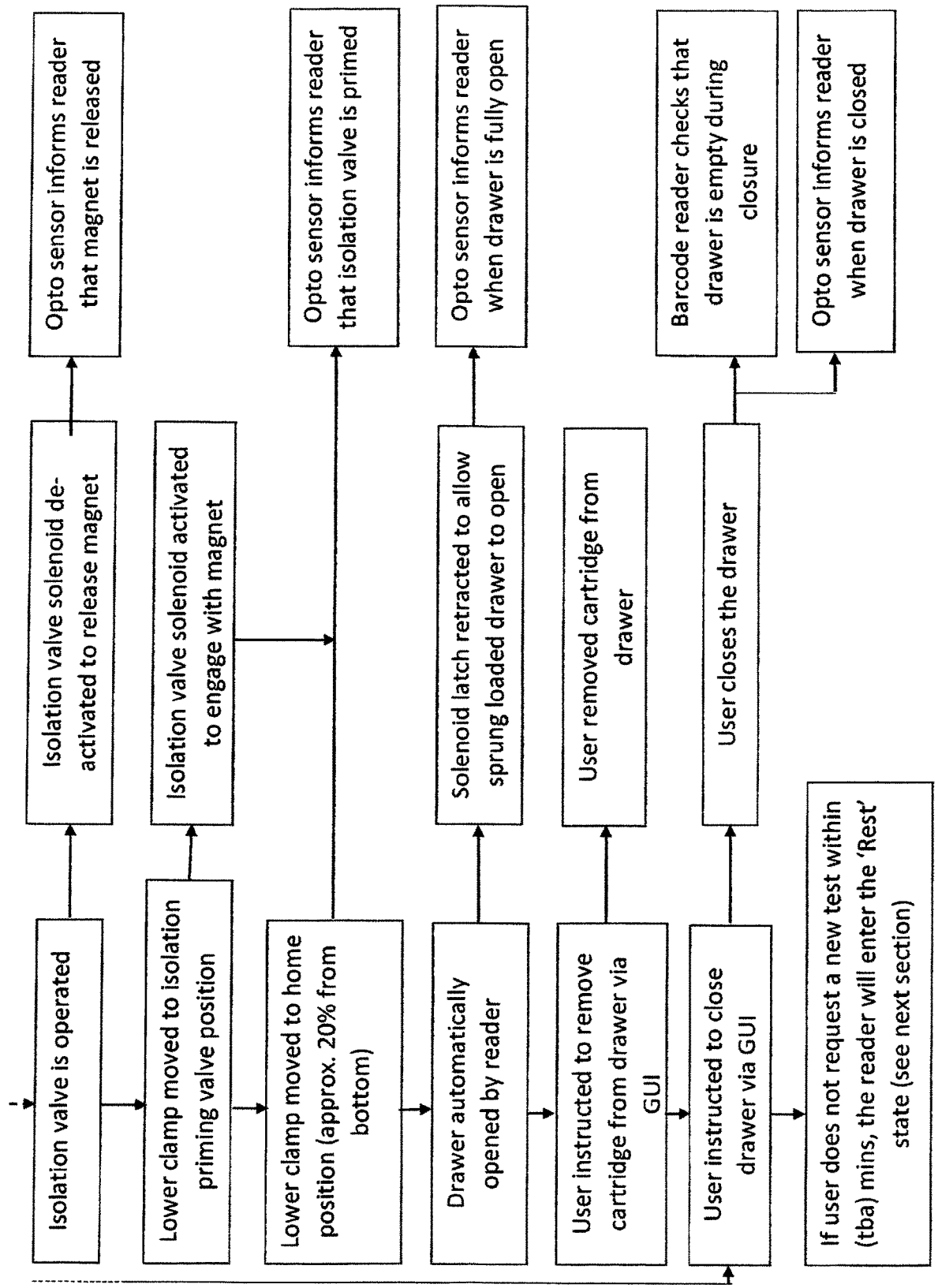
FIG. 23(iii)

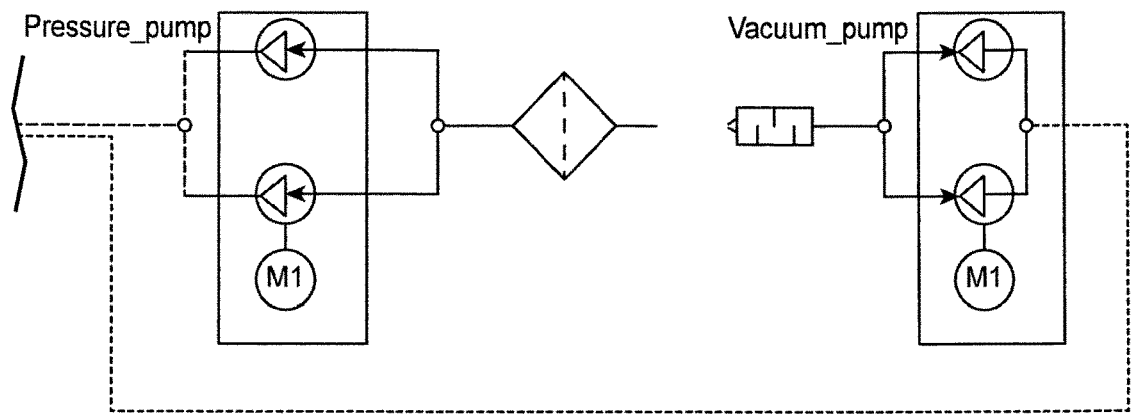
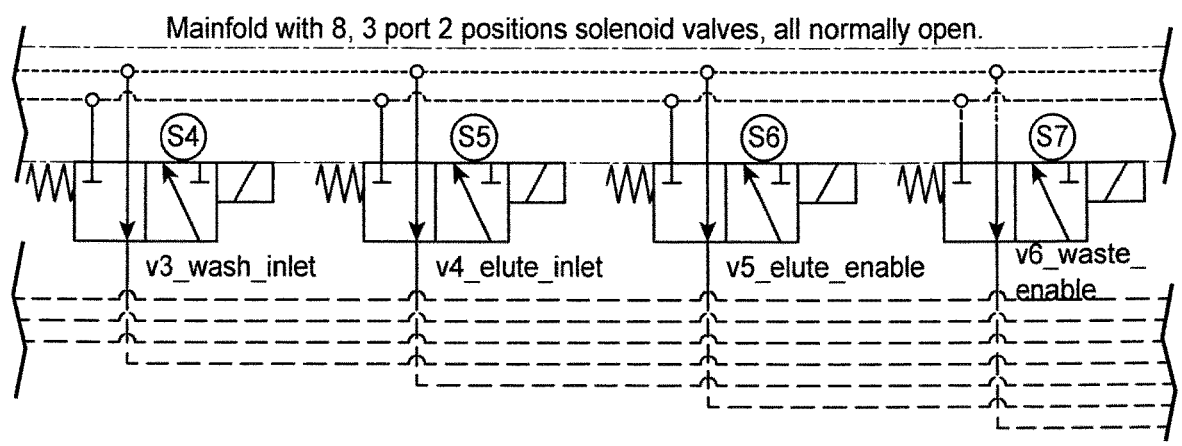
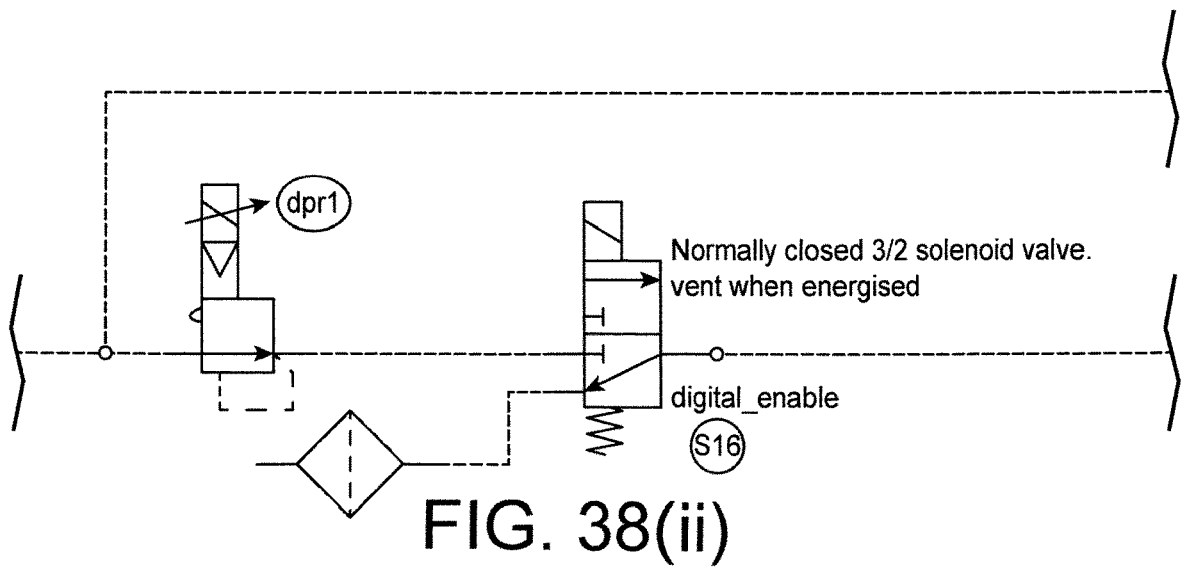
FIG. 38(ii)

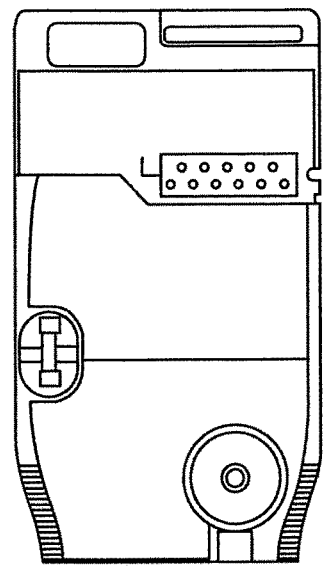
| Cartridge port No. | Solenoid No. on pneumatic block | Cartridge port name |
|---|---|---|
| 1 | S1 | bellows |
| 2 | S2 | pump_v1_pcr |
| 3 | S3 | pump_v2 |
| 4 | S4 | v3_wash_inlet |
| 5 | S9 | eash_airdry |
| 6 | S8 | airdry_enable |
| 7 | S10 | elute_airdry |
| 8 | S5 | v4_elute_inlet |
| 9 | S16 | digital_enable |
| 10 | S6 | v5_elute_enable |
| 11 | S7 | v6_waste_enable |
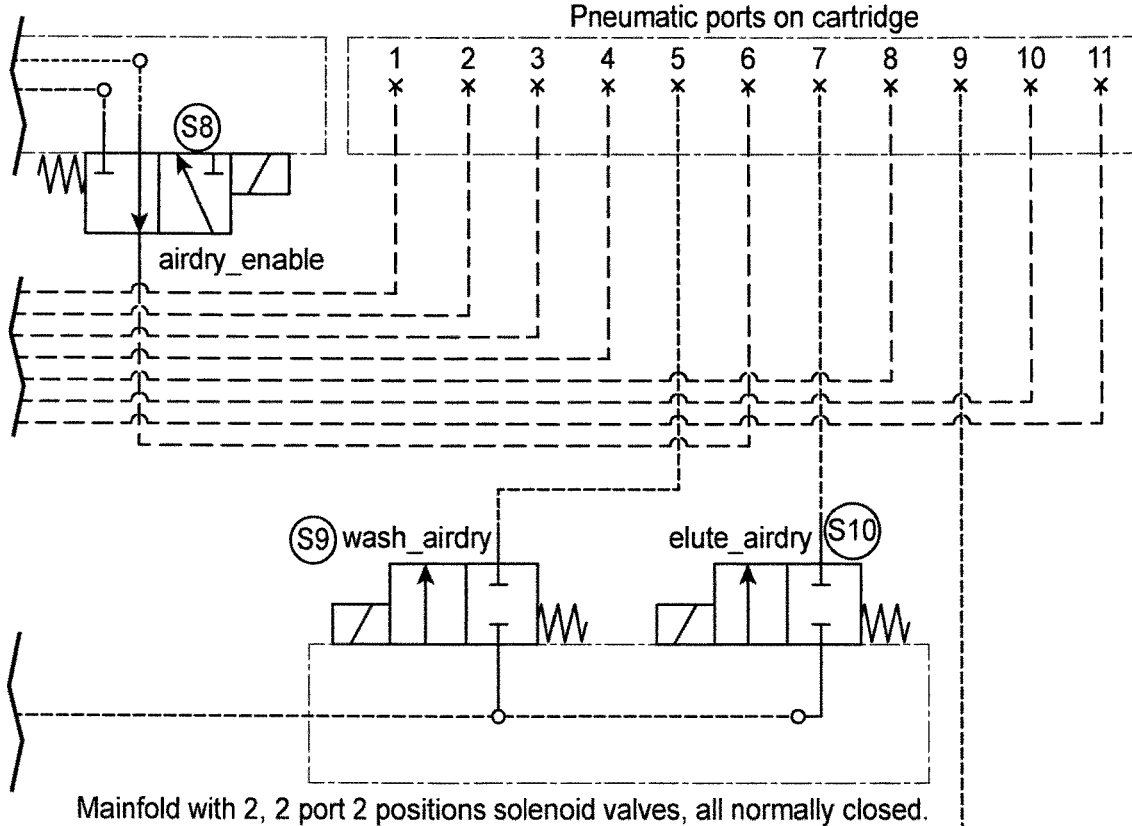
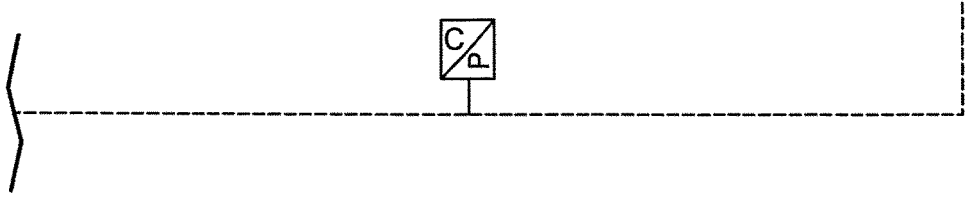
FIG. 38(iii)

INSTRUMENT FOR PERFORMING A DIAGNOSTIC TEST ON A FLUIDIC CARTRIDGE

CROSS-REFERENCE TO RELATED APPLICATIONS

This application is a national stage application, filed under 35 U.S.C. § 371, of PCT International Patent Application No. PCT/GB2016/050234, filed on Feb. 2, 2016, and claims benefit of priority to British Patent Application No. 1501705.6, filed on Feb. 2, 2015, both of which, including their contents, are incorporated herein by reference in their entireties.

FIELD

The present invention relates to a cartridge reader for carrying out a diagnostic test on a fluid sample contained in a fluidic cartridge, and reading a result therefrom.

BACKGROUND

Sample preparation and analysis presents many logistical problems. Conventionally, many medical samples (such as blood, saliva, urine and swab eluate) are provided to a doctor, for example a general practitioner doctor (GP) or a principle care physician (PCP), in a local surgery without the equipment necessary to analyse the sample. Hence, the sample must be sent to a laboratory where the sample is analysed. The test results must then be collated and returned to the GP to analyse the results and make a diagnosis. This approach is inadequate. Firstly, there is a significant risk that a sample is lost in transit or mismatched with the wrong patient. Moreover, whilst recent developments in technology have reduced the overall time taken to conduct the test, the delay involved in sending the sample to a laboratory is unsatisfactory.

Nevertheless, analytical systems of the kind found in laboratories are complex and it is often difficult to provide sufficient amounts of pure targets from source samples to reliably perform downstream analytical assays. This typically prohibits local GP surgeries from being able to carry out such tests on site.

However, in recent years efforts have been made to reduce the scale of the analytical systems to make tests faster and simpler to run, and require smaller quantities of sample. For instance, "laboratory on a chip" (LOC) devices (a subset of microfluidic devices) integrate almost all medical tests or diagnostic operations performed in a hospital on a single microfluidic chip. The channels forming such microfluidics devices handle small fluid volumes and are connected together so as to achieve a desired function such as mixing of a sample, moving the sample through the device, reacting the sample with different reagents, and so on. These chips may be inserted into machines to control the performance of a test and measure the results.

However, it has been found that handling a sample in a microfluidics device can be very difficult. In particular, it is difficult to interface to the small channels and other features that are required to move the sample from one site to another to perform different actions on the sample. There is also a limit to the complexity of a LOC device which operates purely using capillary action. Furthermore, owing to the small sample sizes of LOC's, the devices have reduced sensitivity and the probability of a target being present in the sample is thus reduced.

An alternative approach is to use a fluidic cartridge. The scale of the components of a fluidic cartridge is larger than for a microfluidic device, and so it becomes possible to move a sample through various different sites to perform different actions on it. This makes it possible to perform more complex tests than may be conducted using typical LOC devices, whilst still providing an analytical system of potential use in a local GP surgery.

Fluidic cartridges are generally inserted into a cartridge reader configured to initiate and control at least some of the steps of a test to be carried out. For example, cartridge reader may initiate a test by detecting the presence of a cartridge and moving a sample through the various channels in the cartridge. The reader may initiate the introduction of required reagents into the cartridge, and control variables such as sample temperature throughout the duration of the test. Finally, the reader may be configured to read and display a result to the user, once the required test has been carried out.

Increasingly, scientific assays useful in medical diagnostics have involved biochemical procedures, such as the polymerase chain reaction ("PCR"). The PCR assay has provided a particularly sensitive method of assaying for the presence of defined segments of nucleic acids. It is therefore desirable to perform a PCR assay on a fluidic cartridge, and to provide a cartridge reader, suitable for use in a local surgery of doctors' office capable of carrying out and/or controlling a PCR assay. The use of PCR requires rapid and reliable thermal control on the cartridge, Reducing PCR to the microchip level is important for portable detection technologies and high throughput analytical systems. The method can be used to assay body fluids for the presence of nucleic acid specific for particular pathogens, such as the *Chlamydia trachomatis* bacterium, HIV or any other pathogenic microbe.

The introduction of commercially available automated DNA amplification assays has allowed more laboratories to introduce these technologies for routine testing of specimens. However, there is a need to improve the cartridges and cartridge readers used for this purpose.

Electrochemical signaling may be used to indicate the presence of genetic or immuno-histochemistry targets in a sample. The sample is processed to form an electrolyte which, in practice, may be held in a cell comprising a set of detection electrodes. Upon application of a potential difference across electrodes in the cell, some compounds in an electrolyte will have a natural tendency to migrate to the electrodes and swap electrons, resulting in a tiny current. All combinations of soluble compounds have some electrochemical activity, and the rate at which this activity occurs enables measurement of the quantity of those compounds. Thus, the presence of different compounds in the sample may be measured by searching for characteristic features of their redox electrochemistry. In particular, the sample may be processed to include labels: selected compounds that are present if and only if the sample contains target molecules.

A circuit used to measure electrochemical activity is a potentiostat, which has three electrodes—a working electrode, a counter electrode and a reference electrode. A potential difference is applied across the working and counter electrodes and, as a result, a label indicating the presence of target DNA oxidizes on the working electrode and a current flows from the working electrode to the counter electrode. This current is dependent of the galvanic activity (natural reactivity between electrode and electrolyte) at both electrodes, and in order that only the effect of the working electrode electrochemistry is measured, the potential difference applied is corrected for the galvanic activity of the counter electrode by an amount determined by the reference electrode which is chosen to be a 'standard electrode' relatively unchanged by local chemistry effect.

The current flowing at any given thus-corrected potential difference is measured and provides the signal that is indicative of the label compounds in the sample. Conventionally, the counter electrode is excessively large so that the reaction at this electrode does not limit the current flowing as a result of the reaction of the working electrode, which is the one of interest.

However, during development of a cartridge and a cartridge reader as described above, the inventors found that the signals generated by potentiostats of conventional design were unsatisfactory, and thus had a need for an improved arrangement that generated better signals.

SUMMARY OF INVENTION

In a first aspect, the present invention provides a cartridge reader for carrying out a diagnostic test on a sample contained in a fluidic cartridge comprising a mechanical valve for isolating the sample with the cartridge, the cartridge reader comprising a system for actuating the mechanical valve comprising:

an actuation member configured to move the mechanical valve from an open position to a closed position;

an armature connected to the actuation member, configured to engage an electromagnet, wherein the electromagnet can be switched between an active state in which it electromagnetically holds the armature and an inactive state in which it does not electromagnetically hold the armature;

first biasing means, disposed between the actuation member and a bearing surface, wherein the first biasing means is configured to bias the actuation member into a first position in which it actuates a mechanical valve in a fluidic cartridge inserted into the reader;

wherein the actuation member is held in a second position against the bias of the first biasing means by the electromagnet when the electromagnet is in its active state, and is moved into its first position by the first biasing means when the electromagnet is in its inactive state; and further comprising processing means for controlling operation of the cartridge reader and configured to determine when a diagnostic test carried out by the reader has been completed, and to switch the electromagnet to its inactive state at the end of the diagnostic test so as to move the mechanical valve from an open position to a closed position to isolate the sample within the cartridge.

This ensures that no sample can escape to contaminate other samples after the reader has completed its test and is no longer in control of the cartridge.

In the event of a fault or power failure, the electromagnet becomes inactive and the mechanical valve moves to its closed position to isolate the sample. This ensures that no sample can escape to contaminate other samples if the reader suffers power failure and is unable to complete a test.

In a preferred embodiment, the reader comprises an upper clamp having a fixed position relative to the reader and a lower clamp, movable relative to the upper clamp, wherein the upper clamp and the lower clamp are configured to receive the fluidic cartridge therebetween;

a gantry, fixedly connected to the lower clamp by at least one alignment shaft which passes through at least one aperture in the upper clamp such that at least a portion of the gantry extends above the upper clamp; and wherein the electromagnet is connected to the gantry and the bearing surface is comprised in the upper clamp.

The armature and the actuation member may be connected by a shaft which passes through an aperture in the upper clamp.

In certain embodiments, the reader is further configured to:

move the lower clamp from a first position in which the electromagnet mounted on the gantry is spaced apart from the armature when the armature is in its first position, to a second position in which the electromagnet contacts the armature;

activate the electromagnet when it reaches the second position, thereby engaging the electromagnet with the armature; and move the lower clamp from its second position to a third position, whilst magnetically holding the armature, thereby moving the actuation member to its second position.

Preferably, the reader further comprises second biasing means between the upper clamp and the gantry.

The first biasing means may comprise a first coil spring disposed around the at least one alignment shaft, between the actuation member and the upper housing.

Preferably, a force exerted by the at least one further biasing means exceeds the force exerted by the first biasing means.

In some embodiments, the central axes of the electromagnet, the shaft and the actuation member are offset from each other. In that case, the first biasing means comprises a coil spring, and wherein each of the axes is within a circumference of the first biasing means. This helps to prevent the components from jamming.

The present invention further provides a fluidic cartridge for carrying out a diagnostic test on a sample contained therein, the cartridge comprising a mechanical valve for isolating the sample with the cartridge and configured for use with a cartridge reader of any preceding claim, the mechanical valve configured to be moved from an open position to a closed position by the actuation member.

In a second aspect, the present invention provides a method of using a cartridge reader to actuate an isolation valve in a fluidic cartridge inserted into the reader, wherein the reader comprises a fixed upper clamp, and a lower clamp, movable relative to the upper clamp, defining a cartridge receiving region therebetween, a gantry, fixed relative to the lower clamp, by at least one alignment shaft passing through at least one aperture in the upper clamp, an electromagnet mounted on the gantry, and configured to align with selectively engage a armature of an actuation assembly comprised in the lower clamp, wherein the actuation assembly further comprises an actuation member, and a first biasing means disposed between the actuation member and a bearing surface in the upper clamp, wherein the first biasing means is configured to bias the actuation member into a first position in which it actuates a mechanical valve in a fluidic cartridge inserted into the reader, and wherein the method comprises the steps of:

a. moving the lower clamp from a first position in which the electromagnet is spaced apart from the armature, to a second position in which the electromagnet contacts the armature;

b. activating the electromagnet, thereby magnetically engaging the electromagnet with the armature;

c. moving the lower clamp from the second position to the first position, thereby compressing the first biasing means between the bearing surface and the actuation member;

d. inserting a cartridge having an isolation valve into a reader between the upper and lower clamps;

e. moving the lower clamp to a third position, thereby moving the cartridge from a first position in which it is spaced apart from the upper clamp, to a second position in which it engages the upper clamp;

f. deactivating the electromagnet, thereby releasing the actuation assembly and allowing the first biasing means to move the actuation member from a first position in which it does not actuate the isolation valve to a second position in which it actuates the isolation valve.

Preferably, the step of deactivating the electromagnet is carried out at the end of a test process or in the event of the reader losing power.

Preferably the method further comprising the steps of moving the lower clamp from its third position to its second position after the isolation valve has been actuated.

Preferably the reader further comprises a cartridge drawer, slidable within the upper clamp, and wherein the step of moving the lower clamp from its first position to its second position lifts the cartridge out of the cartridge drawer.

Preferably the reader further comprises second biasing means disposed between the gantry and the upper clamp, and wherein the step of moving the lower clamp from its first position to its second position, compresses the first and second biasing means.

Preferably the force exerted by the second biasing means exceeds the force exerted by the first biasing means.

BRIEF DESCRIPTION OF THE FIGURES

FIG. 6A is a top view of the pneumatic layer of the exemplary fluidic cartridge of FIG. 2.

FIG. 9 is a top view of the fluidic foil of the exemplary fluidic cartridge of FIG. 2.

DETAILED DESCRIPTION

Figure 1:
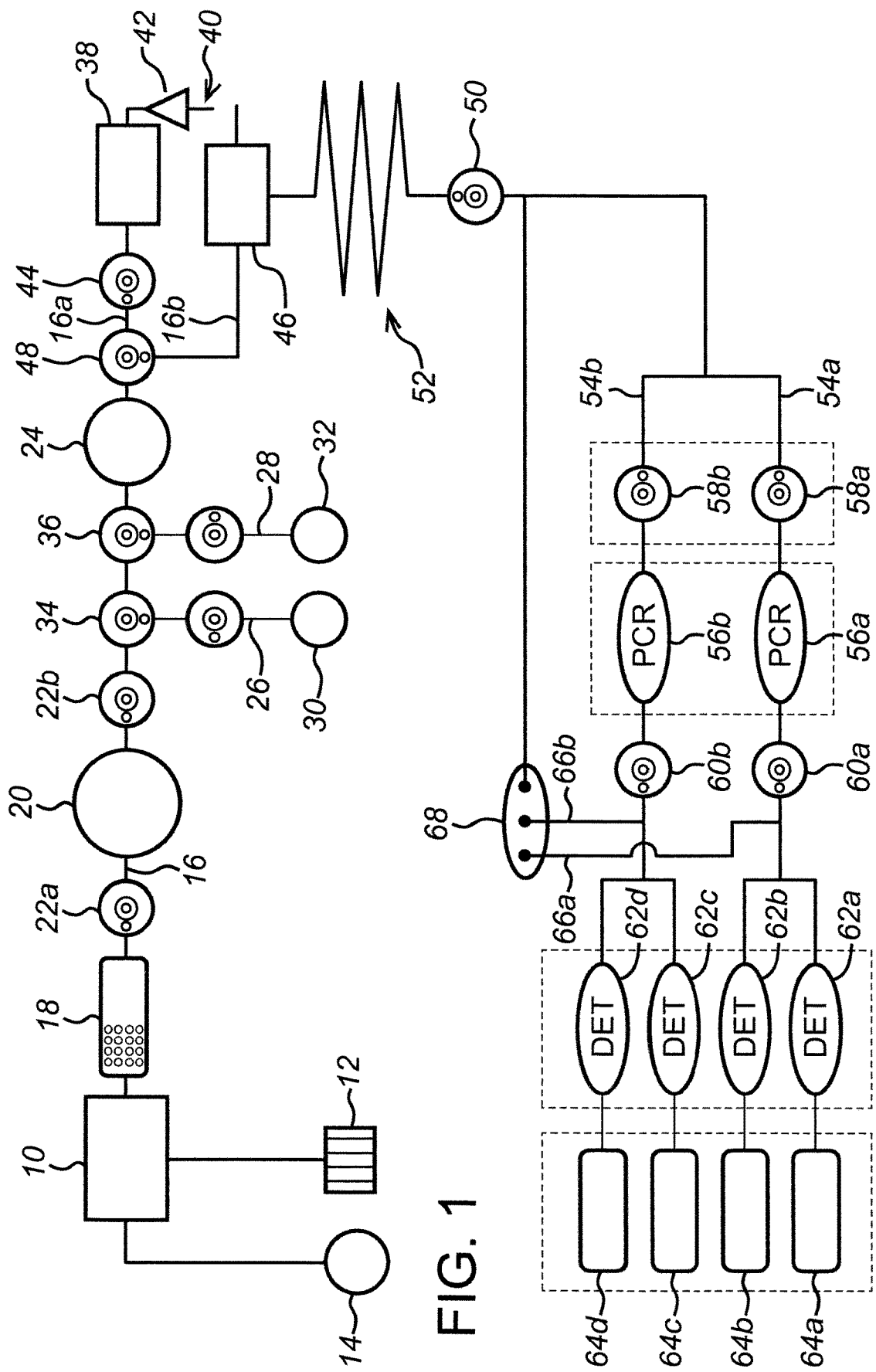
FIG. 1 is a schematic diagram of an exemplary fluidic cartridge in which the invention may be provided.

Embodiments of the invention will now be described in the context of an exemplary cartridge reader for reading an exemplary cartridge. Whilst not necessary to understand the present invention, it is beneficial to provide a general description of the principles of the structure, manufacture, function and use of the cartridge and associated methods of performing a test.

The exemplary cartridge and cartridge reader and associated methods chosen to illustrate the present invention are for the detection of a pathogenic bacterium using a nucleic acid extraction process, followed by PCR amplification and electrochemical detection. However, the skilled person would understand that the invention is not limited to the exemplary reader and associated methods, and is suitable for use in a wide variety of sample analysis techniques or biological assays; for example, assays of any target nucleic acid sequences in a liquid sample.

Those skilled in the art will understand that the devices and methods of the invention described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are included within the scope of the present disclosure.

The exemplary cartridge reader is intended for use with an exemplary fluidic cartridge, which comprises: a fluidic portion through which the sample flows and in which nucleic acid extraction, amplification and detection take place; a pneumatic portion which controls flow through the fluidic portion; a sample processing region for performing nucleic acid on the sample, PCR and at least two electrodes which provide a potential difference for the detection of an amplified nucleic acid of interest. The fluidic portion and pneumatic portion may be constructed of a fluidic layer, a fluidic foil, a pneumatic layer and a pneumatic foil such as those described in relation to the exemplary cartridge below. However, the fluidic portion does not necessarily consist only of a fluidic layer and a fluidic foil and the pneumatic portion does not necessarily consist only of a pneumatic layer and a pneumatic foil. Rather, the layers may interact to produce the fluidic portion and the pneumatic portion such that parts of all or some of the layers make up each portion. Rather than referring to the particular layers of the cartridge, the fluidic portion refers to the particular areas of the cartridge which provide the function of allowing controlled sample flow, and the pneumatic portion refers to the particular areas of the cartridge which provide the function of controlling the flow through the fluidic portion.

The housing, fluidic portion and pneumatic portion are made of plastic. By plastic is meant a synthetic or natural organic material that may be shaped when soft and then hardened, including resins, resinoids, polymers, cellulose derivatives, casein materials, and protein plastics. Examples of plastics from which the cartridge may be constructed include, but are not limited to thermoplastics, for example polycarbonate, polyethylene terephthalate, cyclic olefin copolymers such as Topaz, acrylonitrile butadiene styrene, and thermoplastic elastomers, for example polypropylene. Plastic housings, fluidic portions and pneumatic portions can include components which are not made of plastic (e.g. blisters made from metal foil, metallic inserts at the sample inlet), but they are formed primarily from plastic. The use of plastic materials facilitates economical manufacture of the cartridges.

Whilst the pneumatic and fluidic foils may be made from a metal foil, the preferred materials are plastic including those mentioned above. In particular, it is preferred that foils are a polyethylene terephthalate/polypropylene composite, with the polypropylene in contact with the fluidic sample The target nucleic acid sequence is any nucleic acid to be detected in a sample. The target nucleic acid(s) to be amplified and detected in the cartridge will usually be DNA, but it is also possible to amplify and detect RNA. In some embodiments a cartridge may permit amplification and/or detection of both DNA and RNA targets.

The liquid sample is the composition which is introduced into the cartridge in order to determine whether the target nucleic acid(s) of interest is/are present. The sample may be a composition in which the nucleic acid to be detected is suspected to be present (e.g. for clinical diagnosis), or may be a composition in which the nucleic acid to be detected is potentially present (e.g. for contamination testing).

The liquid sample can have various sources. For instance, it can be material obtained from an animal or plant (e.g. for diagnosis of infections or for genotyping). Such samples may be obtained with minimal invasiveness or non-invasively, e.g., the sample may be obtained from an animal using a swab, or may be a bodily fluid. As an alternative, the sample may be material obtained from food or water (e.g. for contamination testing). The sample will usually include cells, and the target nucleic acid (if present) can be extracted from these cells within the cartridge. One skilled in the art will appreciate that samples can be diluted or otherwise treated prior to being introduced into the cartridge, but it is preferred that the cartridge can handle material which has not been pre-treated in this way.

An animal from whom the sample is obtained may be a vertebrate or non-vertebrate animal. Vertebrate animals may be mammals. Examples of mammals include but are not limited to mouse, rat, pig, dog, cat, rabbit, primates or the like. The animal may be a primate, and is preferably a human. Thus the cartridge can be used for clinical diagnosis of human samples.

In addition to analysing a sample, the cartridge can analyse a positive and/or negative control to provide confirmation that the cartridge is functioning as expected. The control(s) can be introduced into the cartridge by a user, or can be included within a cartridge before use.

The inclusion of a positive internal control nucleic acid allows a user to identify whether a negative result for the sample has been obtained because the nucleic acid amplification has been unsuccessful (invalid result). If the positive control nucleic acid fails to be detected in the detection chamber, despite its presence in an amplification chamber, the user will be able to identify the test as an invalid result, and can perform another test.

A positive control nucleic acid may be any nucleic acid that will not be found in a sample used in the cartridge. The internal control DNA may be taken from a bacterium that is not pathogenic to animals and which contains a nucleic acid that is highly specific to the bacterium. One example of a possible bacterium from which the control nucleic acid may be taken for an animal sample is *Pectobacterium atrosepticum*, although any control nucleic acid may be used that will not be present in a sample.

The fluidic portion of the cartridge comprises channels and chambers through which sample flows. The flow of sample through the cartridge is controlled in two ways. Firstly, the fluidic portion has a gas inlet. The gas inlet is connected to a gas supply, and injection of gas into the fluidic portion via this inlet allows the sample to be pushed downstream through the cartridge, towards the detection chamber. The gas supply may be provided by the reader. As an alternative, the gas supply may be an on-board gas supply. Preferably, the gas supply is provided by an external source and the gas inlet is connected to a pneumatic circuit such that the gas supply is provided via a pneumatic inlet on the cartridge. Secondly, at least one pneumatically controlled valve controls local movement of the sample through the fluidic portion. The pneumatically controlled valve(s) may be controlled independently of other pneumatically controlled valves and may be controlled independently of the gas supply that generally causes downstream movement of the sample via the gas inlet. The gas inlet and the pneumatically controlled valve(s) also permit sample to be flushed through the fluidic portion e.g. to exclude excess volumes of material. The fluidic portion also has an exhaust which allows air and waste material to exit the channels and chambers of the fluidic portion without a build-up of pressure occurring in the cartridge. Preferably, the exhaust comprises a waste chamber and/or a waste vent.

The fluidic portion of the cartridge includes reagents and/or physical components for cell lysis and nucleic acid separation. These may be any reagents or physical components that are capable of lysing cells and separating nucleic acids from cell debris and other cellular components. For instance, they may comprise (i) a lysis buffer which is capable of causing lysis of target cells which may be present in the sample e.g. buffers including a detergent such as nonyl phenoxypolyethoxylethanol (available as NP-40) or t-octylphenoxypolyethoxyethanol, (available as Triton X 100), or including guanidine thiocyanate, and/or (ii) a capture support or column which specifically binds nucleic acids but does not bind other undesired cellular components (e.g. proteins and lipids). The capture column comprises a capture filter and may additionally comprise a depth filter. The filters may be made of glass fibres (available as Whatman filters), or may be made of silica, although any column or support which is capable of separating nucleic acids from other cellular components may be used. Elution using a wash buffer to remove cell debris and other cellular components, followed by elution using an elution buffer to elute the separated nucleic acids from the capture support or column can be undertaken such that the capture column can separate nucleic acids from cell debris and other cellular components.

A channel through which the sample flows fluidly connects the sample inlet to at least one amplification chamber where nucleic acid amplification can take place. The purpose of the amplification chamber(s) is to permit amplification of any target nucleic acid of interest that is present in the sample (and, where present, any positive control nucleic acid). Any nucleic acid amplification method may be used and these are described in more detail below in relation to an exemplary cartridge. The different nucleic acid amplification reagents that are required for different nucleic acid amplification methods are well known in the art. These reagents are provided in or upstream of the amplification chamber(s) such that the sample (and any positive control) includes all necessary reagents for nucleic acid amplification once it reaches the amplification chamber. Adaptation of a nucleic acid amplification method according to the target nucleic acid to be detected is also well known in the art (e.g. design of primers). The skilled person would therefore be able to adapt the reagents for nucleic acid amplification accordingly. The term "chamber" does not denote any particular size or geometry, but instead it means a region within the fluidic portion which is designed to permit nucleic acid amplification to occur. Thus, for instance, it could be a region in which the sample can be fluidically isolated (e.g. via the use of pneumatically controlled valves) while the steps required for nucleic acid amplification (e.g. thermocycling, etc.) occur, and it can be located within the cartridge so that it is in the proximity of any external resources that are needed (e.g. next to a heat source within a cartridge reader, thereby permitting thermal cycling to occur).

Multiple test amplification channels and/or chambers may be included in the cartridge. The different test amplification channels and/or chambers may include reagents required to amplify different nucleic acids of interest. Therefore using multiple amplification test channels and/or chambers allows multiple tests to be performed on a single cartridge, simultaneously (including any controls). As an alternative, reagents for amplification of multiple different nucleic acids may be present in a single amplification chamber, and the different nucleic acids (whether multiple target nucleic acids, or a target nucleic acid and a control nucleic acid) may be amplified simultaneously in the same amplification chamber.

A further channel through which the sample flows after nucleic acid amplification fluidly connects the at least one amplification chamber to at least one detection chamber where the results of nucleic acid amplification can be detected. In or upstream of the detection chamber are reagents for nucleic acid detection such that the sample includes all necessary reagents for the detection once it reaches the detection chamber. The reagents for nucleic acid detection may be specific for the particular target nucleic acid, i.e. they may allow for detection of the presence of the specific nucleic acid sequence. As an alternative, the reagents for nucleic acid detection may be generic reagents to detect the presence of any nucleic acids. Such generic reagents may be used if all nucleic acids other than the target nucleic acid are removed prior to detection. For example, this may be achieved by providing a nuclease that is capable of hydrolysing all nucleic acids present in the sample other than the target nucleic. The amplified target nucleic acid can be protected from hydrolysis, for example by inclusion of chemical modifications in the primers which are incorporated into the amplified product and which cannot be hydrolysed. Reagents for nucleic acid detection are described below in relation to an exemplary cartridge but usually comprise a probe including an electrochemical label. The probe is capable of hybridising to the amplified nucleic acid which has been amplified in the amplification chamber(s). Following hybridisation of the probe to the amplified nucleic acid, the detection of the nucleic acid may occur via a detectable change in the signal from the label. In practice, this involves three stages: binding of a probe to the target DNA, cleaving of the label from the probe by T7, followed by detection of the signal from the label. In some embodiments the change may be caused by hydrolysis of the probe. Where the probe is hydrolysed, hydrolysis is usually achieved using a double strand specific nuclease, which can be an exonuclease or an endonuclease. Preferably, the nuclease is T7 endonuclease. The signal from the label is capable of undergoing a change following hydrolysis of the probe. This is due to a change in the environment of the label when it moves from being bound to the rest of the probe to being free from the rest of the probe or bound to a single nucleotide or a short part of the probe. Further details of the types of probes and detection methods that may be used can be found in Hillier et al. Bioelectrochemistry, 63 (2004), 307-310. As an alternative, methods for causing a detectable change in the signal from the label which do not rely on hydrolysis of the probe may be used e.g. see Ihara et al. Nucleic Acids Research, 1996, Vol. 24, No. 21 4273-4280. This change in environment of the label leads to a change in the signal from the label. The change in signal from the label can be detected in order to detect the presence of the nucleic acid of interest.

Where a positive control nucleic acid is used, the reagents for nucleic acid detection will additionally include a positive control probe including a label. The positive control probe is capable of hybridising to the amplified control nucleic acid. The signal provided by the labels of the positive control and target probes may be the same, but present in separate detection chambers such that the signals corresponding to the control and test nucleic acids can be distinguished. As an alternative, the signal provided by the labels of the control and target probes may oxidise at different voltages, such that the signals are distinguishable from one another, even if the probes are present in the same detection chamber.

Multiple test detection channels and/or chambers may be included in the cartridge. The different test detection channels and/or chambers may include reagents required to detect different nucleic acids of interest. Therefore using multiple detection test channels and/or chambers allows multiple tests to be performed on a single cartridge, simultaneously. As an alternative, reagents for detection of multiple different nucleic acids may be present in a single detection chamber, and the different nucleic acids (whether multiple target nucleic acids or a target nucleic acid and a control nucleic acid) may be detected simultaneously in the same detection chamber.

The label is detectable by use of the cartridge's electrodes, and so the label will usually be an electrochemical label, such as a ferrocene. Examples of labels which may be used can be found in WO03/074731, WO2012/085591 and PCT/GB2013/051643. Signal emitted by the label can be detected by a cartridge reader.

The pneumatic portion of the cartridge comprises at least one pneumatic circuit which each control at least one pneumatically controlled valve. The pneumatic portion controls sample flow through the cartridge by the opening and closing of pneumatically controlled valves. The opening and closing of the valves is controlled by changes in pneumatic pressure in the pneumatic circuit that is applied through a pneumatic pressure inlet. Usually, the cartridge contains many pneumatically controlled valves. The pneumatically controlled valves may be controlled by separate pneumatic pressure inlets. These valves can be used to prevent downstream movement of sample through the fluidic portion until necessary steps have been performed and/or to prevent unwanted reverse movement of sample upstream. For example, a valve may be provided upstream of the at least one amplification chamber in order to prevent downstream movement into the at least one amplification chamber until cell lysis and nucleic acid separation has taken place. Following cell lysis and nucleic acid separation the valve upstream of the at least one amplification chamber may be opened in order to allow downstream flow. It can then be closed again, to prevent backflow out of the chamber back towards the sample inlet.

The cartridge comprises at least two electrodes which can provide a potential difference across the at least one detection chamber. The potential difference causes current to flow through the at least one detection chamber, thereby permitting the detection of signal from electrochemically active labels.

The cartridge reader generally comprises a cartridge receiving region into which a cartridge containing a sample may be inserted; first and second clamps, between which the cartridge is held during a test cycle; a pneumatics assembly, for coupling to pneumatic ports on the exemplary cartridge and actuating one or more pneumatic valves comprised within the exemplar cartridge; a thermal module, which comprises one or more thermal stacks for heating various sample handling zones in the fluidic cartridge, an electronics interface, configured to couple to the at least two electrodes and receive an electrical signal therefrom; and a control unit comprising the processing means required for controlling the test and reading a result therefrom. The exemplary cartridge reader may also comprise: one or more mechanical actuators for actuating one or more collapsible blisters provided on the fluidic cartridge and configured to eject a fluid contained therein into the network of channels in the fluidic device; a mechanical valve actuator for actuating a mechanical valve comprised within the cartridge; an isolation actuator, configured to actuate an isolation valve comprised on the fluidic cartridge in the event of a fault, power loss or at the end of a test. The cartridge reader may also comprise means for identifying a cartridge inserted into the reader, such as, for example, a bar code reader for reading information from a bar code label affixed to the cartridge.

1. The Exemplary Cartridge 1.1 Overview

The exemplary cartridge described below is intended to be a single-use, disposable cartridge for performing a test on a sample introduced into the cartridge. The exemplary cartridge is a fluidic cartridge with channels of an appropriate scale (as detailed hereafter). However, the invention may be performed on a microfluidic device, or an LOC. Once the test has been run, it is preferred that the cartridge is disposed of. However, if desired, the cartridge may be sent for re-processing to enable it to be used again.

It is preferred that the cartridge comprises all of the biological agents necessary for conducting the test of choice. For example, the exemplary cartridge is used for detecting the presence, absence or amount of a pathogen of interest. Any pathogen may be detected. Examples of pathogens which may be detected by the cartridge are *Chlamydia trachomatis, Trichomonas vaginalis, Neisseria gonorrhoea, Mycoplasma genitalium* and methicillin resistant *Staphylococcus aureus*. To that end the cartridge comprises buffers for lysis the bacteria, washing the debris to waste and a clean buffer for re-suspending the target DNA. The cartridge also comprises dry reagents for nucleic acid amplification. Nucleic acid amplification may be performed using any nucleic acid amplification method. The nucleic acid amplification method may be a thermocycling method in which the temperature at which the method is performed is varied such that different steps of the amplification are able to take place at different temperatures within the cycle. For example melting, annealing of primers and extension may each be performed at different temperatures. By cycling through the temperatures, the timing of each of the steps of the method can be controlled. As an alternative, the nucleic acid amplification may be an isothermal method in which the temperature is kept constant. In both the thermocycling and the isothermal nucleic acid amplification methods, the temperature is controlled during nucleic acid amplification.

Examples of nucleic acid amplification methods are the polymerase chain reaction (PCR), the ligase chain reaction (LCR), strand displacement amplification (SDA), transcription mediated amplification, nucleic acid sequence-based amplification (NASBA), helicase-dependent amplification and loop-mediated isothermal amplification. The reagents for nucleic acid amplification will vary depending of the nucleic acid amplification method used but include a polymerase and nucleotide triphosphates.

As explained below, the cartridge also comprises detection reagents which are capable of detecting the presence or absence of amplified nucleic acids which are the product of the nucleic acid amplification method. The reagents for nucleic acid detection comprise a probe which is capable of hybridising to the amplified nucleic acid. The probe includes a ferrocene label. Following hybridisation of the probe to the amplified nucleic acid, the detection of the nucleic acid occurs via a detectable change in the signal from the label. The change is caused by hydrolysis of the probe, which is achieved using a double strand specific nuclease. The nuclease is a T7 endonuclease. The ferrocene gives different electrochemical signals when it is part of a probe or when it is attached only to a single nucleotide, and so hydrolysis is easily detected. Thus, the change in signal from the label permits detection of the presence of the nucleic acid of interest.

The electrodes allow the detectable change in the signal from the label, which occurs in the presence of the target nucleic acid, to be detected.

The cartridge is configured for use with a cartridge reader (not shown). The cartridge comprises a number of pneumatic, mechanical, thermal and electrical interfaces (described in more detail below) through which the reader interacts with the cartridge to perform the test. Hence, in use, the cartridge would be inserted into the reader, and the reader would be activated to begin interacting with the cartridge via the interfaces to perform the test. For the purposes of understanding the present invention, it is not necessary to describe exactly how the cartridge interacts with the reader to conduct a particular test and provide the test results, but an overview of an exemplary operation of a cartridge is provided hereafter.

1.2 Schematic Diagram of the Exemplary Cartridge

Before explaining the structure and arrangement of the components of an exemplary fluid cartridge in detail, it is helpful to describe the layout of the exemplary cartridge at a high level with reference to the schematic shown in FIG. 1.

It is convenient to consider the overall layout of the cartridge in terms of the flow of liquids, including the liquid sample, through the cartridge. Unless otherwise specified hereafter, the passage of liquids including the liquid sample and the liquid buffers is referred to as the 'fluid pathway' which has an upstream end and a downstream end. Unless otherwise specified hereafter, 'downstream' generally refers to the direction of flow of the liquids and 'upstream' refers to the direction opposite the direction of flow. The fluid pathway in the exemplary cartridge may have different branches (and thus form different fluid pathways), but all pathways have a recognisable direction of flow which permit a skilled person to identify the upstream and downstream directions. However, there is an exception to this general definition, which is when the liquid sample is pumped between the mixing chamber 10 and the bellows 20. In this case, fluid is intermittently pumped back upstream in the opposite direction to its general direction of fluid flow, which is downstream. This mixing serves to mix the lysis and sample and to rehydrate the internal control.

The liquid sample is introduced into the cartridge at a sample mixing chamber 10 through an entry port. A particular arrangement of a preferred entry port may itself form an isolated inventive aspect of the cartridge, as described further in section 3, below. A sample indicator 12 is fluidly coupled to the sample mixing chamber 10 such that a sample introduced into the sample mixing chamber 10 is visible in the sample indicator 12. Also connected to the sample mixing chamber 10 is a blister 14 containing a lysis buffer. The lysis buffer comprises guanidine thiocyanate. Once the sample has been introduced into the sample mixing chamber 10, and a test is started, the lysis blister 14 is collapsed so as to expel the lysis buffer into the sample mixing chamber 10 where it mixes with the liquid sample introduced therein.

Downstream of the sample mixing chamber 10, along a main channel 16, is a coarse filter 18. The coarse filter 18 filters out any large debris in the liquid sample, such as skin or bodily hair, as the liquid sample passes through main channel 16.

Downstream of the coarse filter 18, along the main channel 16, is a bellows 20 having an upstream bellows valve 22a and a downstream bellows valve 22b. As described in more detail below, the bellows 20, together with its upstream and downstream valves 22a-b, is capable of pumping the liquid sample from the upstream end of the fluid pathway (i.e. from the sample mixing chamber 10) to the downstream end. In summary, this is achieved by virtue of flexible membranes within the bellows 20 and the upstream and downstream bellows valves 22a-b which actuate to create local pressure differentials to, on the one hand, draw in the liquid sample from the sample mixing chamber 10 into the bellows 20 and, on the other hand, from the bellows 20 further downstream through the main channel 16. This is achieved by carefully choreographed pneumatic actuation of the flexible membranes in the valves. Particular arrangements of a preferred valve may themselves form isolated inventive aspects of the cartridge, as described further in section 3, below.

Downstream of the bellows along the main channel 16 is a capture column 24. The purpose of the capture column 24 is to separate nucleic acids from cell debris and other cellular components. The capture column comprises a capture filter and a depth filter both made of glass fibres. A particular arrangement of a preferred capture column may itself form an isolated inventive aspect of the cartridge, as described further in section 3, below.

Two branch channels 26, 28 join the main channel 16 between the downstream bellows valve 22b and the capture column 24. The purpose of the branch channels is to introduce liquid buffers necessary for performing the desired test. For example, with the test conducted by the exemplary cartridge, it is necessary to introduce an elution buffer and a wash buffer into the main channel once the sample has passed through. The wash buffer is contained in a wash buffer blister 30 and the elution buffer is contained in an elution buffer blister 32. The introduction of the wash buffer and elution buffer into the main channel 16 is controlled by wash buffer valve 34 and elution buffer valve 36, respectively. At the appropriate point in the test, the wash and elution buffer blisters 30, 32 are collapsed so as to expel the wash and elution buffers into the branch channels 26, 28 and thence into the main channel 16 through the wash and elution buffer valves 34, 36.

Downstream of the capture column 24, along a waste branch 16a of the main channel 16, is a waste chamber 38. A particular arrangement of a preferred waste chamber may itself form an isolated inventive aspect of the cartridge, as described further in section 3, below. The purpose of the waste chamber 38 is to collect the cell debris and cellular components other than nucleic acids and contain them, thereby preventing them from entering the test channel 54a or the control channel 54b. The waste chamber 38 is vented to atmosphere through a waste vent 40, and an aerosol impactor 42 is provided between the waste chamber 38 and the waste vent 40 to prevent particulate matter from escaping from the waste chamber 38 into the atmosphere. A waste chamber valve 44 in the main channel waste branch 16a of the main channel 16 permits and prevents fluids passing into the waste chamber 38 at appropriate points during the test.

Downstream of the capture column 24, along an elution branch 16b of the main channel 16, is an elution chamber 46. The purpose of the elution chamber 46 is to allow the sample preparation to settle and for bubbles to disperse before the sample enters the amplification chambers. An elution chamber valve 48 in the elution branch 16b of the main channel 16 permits and prevents fluids passing into the elution chamber 46 at appropriate points during the test.

Downstream of the elution chamber 46 is a convoluted mixing channel 52. Here the prepared sample is mixed prior to passing through the isolation valve 50.

In the present application, the components upstream of the isolation valve 50 are referred to as being comprised in the 'front end' of the cartridge, whilst the components downstream of the isolation valve 50 are referred to as being comprised in the 'back end' of the cartridge. Broadly speaking, the liquid sample is prepared for analysing in the front end of the cartridge, and the analysis is carried out on the sample in the back end of the cartridge.

The isolation valve 50 is open to permit the prepared liquid sample to pass from the front end to the back end of the cartridge. At an appropriate point in the test, after the liquid sample has been prepared and is within the back end of the cartridge for analysis, the isolation valve 50 is closed to prevent any of the sample from re-entering the front end. Once the isolation valve 50 is closed, it cannot be opened again. The isolation valve 50 also acts as a safeguard in case of a power failure, wherein the reader closes the isolation valve 50 to prevent leakage.

Downstream of the isolation valve 50, the fluid pathway splits into an amplification test channel 54a and an amplification control channel 54b. Each of the amplification channels 54a-b comprises an amplification chamber 56a-b having an amplification chamber inlet valve 58a-b and an amplification chamber outlet valve 60a-b. Any nucleic acid amplification method may be performed in the nucleic acid amplification chamber. If PCR is used, the nucleic acid amplification chambers contain a thermostable DNA polymerase, dNTPs, a pair of primers which are capable of hybridising to the nucleic acid to be amplified. Optionally, the nucleic acid amplification chambers may additionally contain buffer salts, $MgCl_2$, passivation agents, uracil N-glycosylase and dUTP. An example of a thermostable DNA polymerase that may be used is Taq polymerase from *Thermus aquaticus*.

Each of the nucleic acid amplification chambers in the exemplary cartridge comprises reagent containment features in the form of first and second shallow wells formed in the fluidic layer. The reagents to be used in the cartridge are spotted in the wells. In the exemplary cartridge, the test-specific reagents and the generic reagents are isolated from each other by spotting each in a different well. Hence, the test-specific reagents are spotted in a first well in the chamber and the generic reagents are spotted in a second well in the chamber. By spotting the reagents separately, it is easier to swap the test-specific reagents during manufacture for a different set of test-specific reagents, so as to perform a different test, whilst keeping the generic reagents as they are.

In the exemplary cartridge, the ratio of nucleic acid amplification chambers to detection chambers is 1:2. The prepared sample enters the back end of the cartridge at the isolation valve 50 and is split into two nucleic acid amplification chambers. After processing, the each of the two processed measures of sample from the nucleic acid amplification chamber is split into two detection chambers. Therefore, for each sample introduced into the exemplary cartridge, four detection chambers may be filled from two nucleic acid amplification chambers, thus facilitating duplex amplification and 4-plex detection.

However, it will be appreciated that one or three or more nucleic acid amplification chambers may be provided to provide any level of multiplexing desired, and that the number of the detection chambers provided may be adjusted accordingly to maintain a 1:2 ratio of nucleic acid amplification chambers to detection chambers.

The ratio 1:2 is preferred for the exemplary cartridge because such a ratio allows twice the number of target nucleic acids to be assayed compared to the number of different labels required for detection in the detection chambers. However, it will be appreciated that the ratio may be changed depending on the number of labels and PCR targets for the liquid sample. For instance, the ratio may be 1:1, 1:3 or 1:n such that there are n detection chambers branching from the main channel of each fluid pathway when there are n times as many multiplexed PCR targets for the number of labels.

PCR primers specific for *Chlamydia trachomatis* are dried down in the amplification chamber in the amplification test channel together with the other reagents required for nucleic acid amplification. PCR primers specific for a positive control nucleic acid are dried down in the amplification chamber in the amplification control channel together with the other reagents required for nucleic acid amplification. A positive control nucleic acid is also provided in the amplification chamber in the amplification control channel, taken from *Pectobacterium atrosepticum*. The dried down reagents are reconstituted when the liquid sample reaches them.

Downstream of the amplification chamber outlet valves 60a-b each of the amplification channels 54a-b splits into two further detection channels, leading to two detection chambers for each amplification chamber, giving a total of four detection chambers 62a-d in total. The reagents for nucleic acid detection, including the target probe, are dried down in the detection chambers 62a-d downstream of the test amplification chamber 56a or 56b. The reagents for nucleic acid detection including the control probe are dried down in the detection chambers downstream of the control amplification chamber 56a or 56b (whichever is not the test chamber mentioned above). Each detection chamber 62a-d is provided with its own gas spring 64a-d which forms a dead end at the downstream end of the fluid pathway.

Reagents for nucleic acid detection are provided in detection chambers. The reagents for nucleic acid detection include probes having a ferrocene label. These probes are capable of hybridising to the amplified nucleic acids. Following hybridisation of the probes to the amplified nucleic acids, the probes are hydrolysed by a double strand specific nuclease[1] which causes the label to be freed from the rest of the probe. As explained above, freeing of the label from the rest of the probe causes a detectable change in the signal from the label. The control probe is provided in separate detection chambers to the target probe and detection of the target nucleic acid and the control nucleic acid take place in different detection chambers, such that the signals are distinguishable from one another.

Downstream of the amplification outlet valves 60a-b, but upstream of the forks creating the four detection channels, two bypass channels 66a-b respectively join the two amplification channels 54a-b. The purpose of the bypass channels 66a-b is to remove excess liquid sample within the amplification channels 54a-b before the liquid sample enters the detection chambers 62a-d. The bypass channels 66a-b connect to a bypass valve 68, which is also fluidly coupled to the elution chamber branch 16b of the main channel 16, downstream of the isolation valve 50, before the channel splits into amplification channels 54a and 54b.

A particular arrangement of a preferred chamber in the cartridge, such as the first and second amplification chambers or the first to fourth detection chambers, may itself form an isolated inventive aspect of the cartridge, as described further in section 3, below.

It will be appreciated that the number of amplification chambers, and the number of detection chambers in the exemplary cartridge may vary depending on the preferred implementation. Moreover, other configurations of channels, chambers, valves and so on are possible without departing from the scope of the invention, as defined by the claims.

The physical structure and operation of the various components of the exemplary cartridge introduced above will now be explained with reference to FIGS. 2 to 10.

Figure 2:
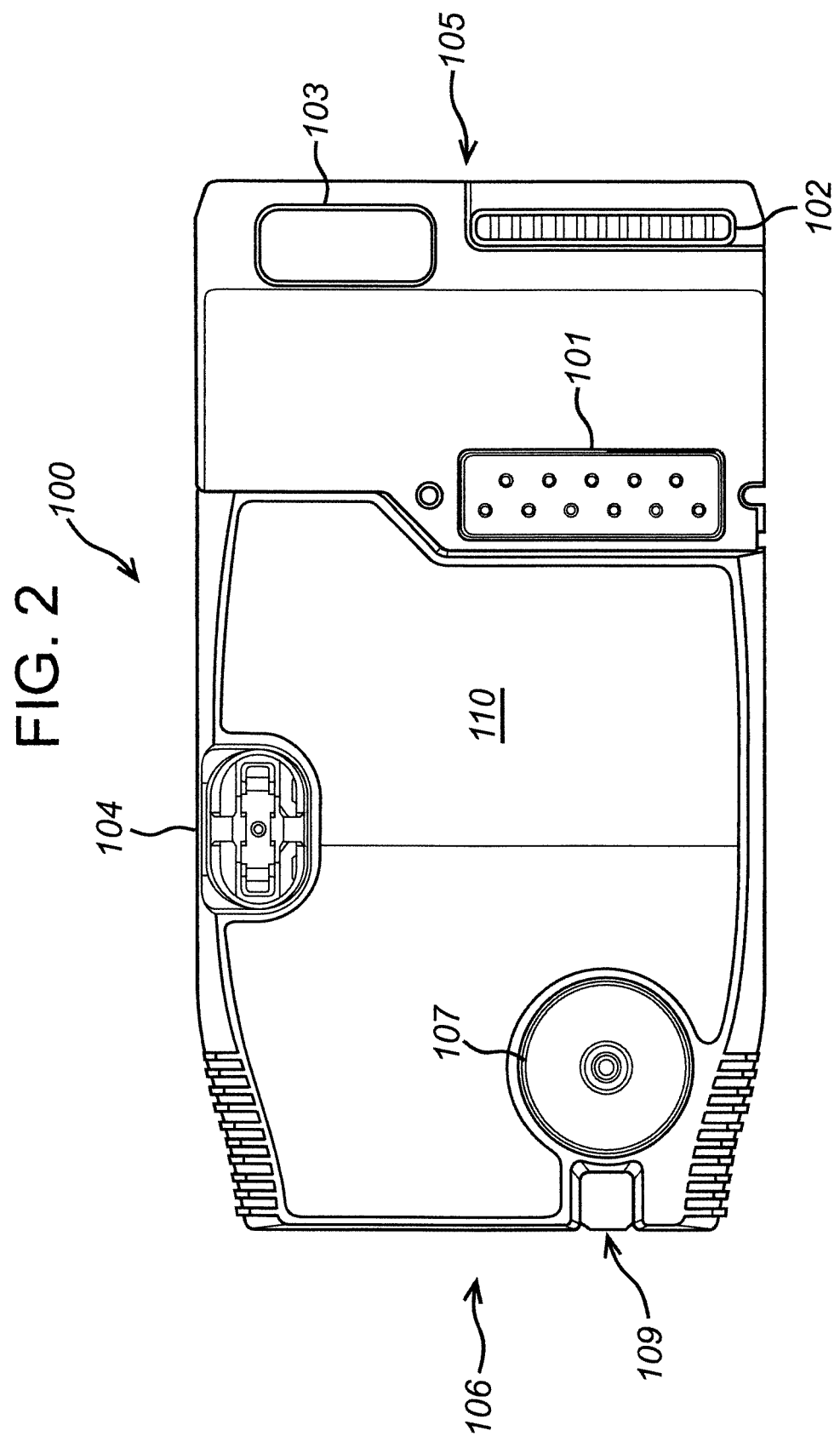
FIG. 2 is a top view of an exemplary fluidic cartridge in which the invention may be provided.

1.3 Physical Structure of an Exemplary Cartridge 1.3.1 Overview and External Features of the Exemplary Cartridge An exemplary cartridge is shown in FIG. 2. As described above, the reader interacts with the cartridge through a plurality of interfaces. The interfaces shown in the exemplary cartridge 100 are: a pneumatic interface 101; an electrical interface 102; a bypass valve interface 103; and an isolation valve interface 104. Each of these interfaces is described in more detail below. It will be appreciated that more or fewer interfaces could be provided, depending on the preferred implementation.

Also provided in the cartridge, but not shown, is a thermal interface. The thermal interface allows the temperature of the amplification chambers to be regulated to allow nucleic acid amplification to take place.

The exemplary cartridge 100 shown in FIG. 2 comprises an insertion end 105 for insertion into the reader, and a non-insertion end 106. Proximate the non-insertion end 106 is a sample inlet 107 for introducing a sample into the sample mixing chamber 10. In the exemplary cartridge, the sample will usually include cells, and the target nucleic acid (if present) can be extracted from these cells, but other fluid samples such as swab eluate, urine, semen, blood, saliva, stool sweat and tears could be used in other implementations. The sample may be introduced into the sample mixing chamber 10 through the sample inlet 107 using a pipette, for example.

The exemplary cartridge 100 and reader are configured such that when the cartridge is inserted into the reader, all of the aforementioned interfaces are actuatable by the reader. On the other hand, the sample inlet 107 remains external to the reader such that a sample may be introduced into the sample mixing chamber 10 whilst the cartridge is inserted into the reader.

The exemplary cartridge 100 shown in FIG. 2 further comprises a sample indicator window 109, through which the sample indicator 12 is visible to determine whether a sample has been introduced into the sample mixing chamber 10.

All of the pneumatic, mechanical and electrical interfaces in the exemplary cartridge 100 are located on the same face of the cartridge, in this case the top face 110. The thermal interface (not shown) is provided on the bottom face of the cartridge. This simplifies the design of the reader, which may this provide the associated pneumatic, mechanical and electrical parts which interact with those interfaces in the same region of the reader, thereby making best use of space. It also enables the thermal part of the reader to be provided away from the pneumatic, mechanical and electrical parts.

1.3.2 Internal Components of Cartridge

Figure 3:
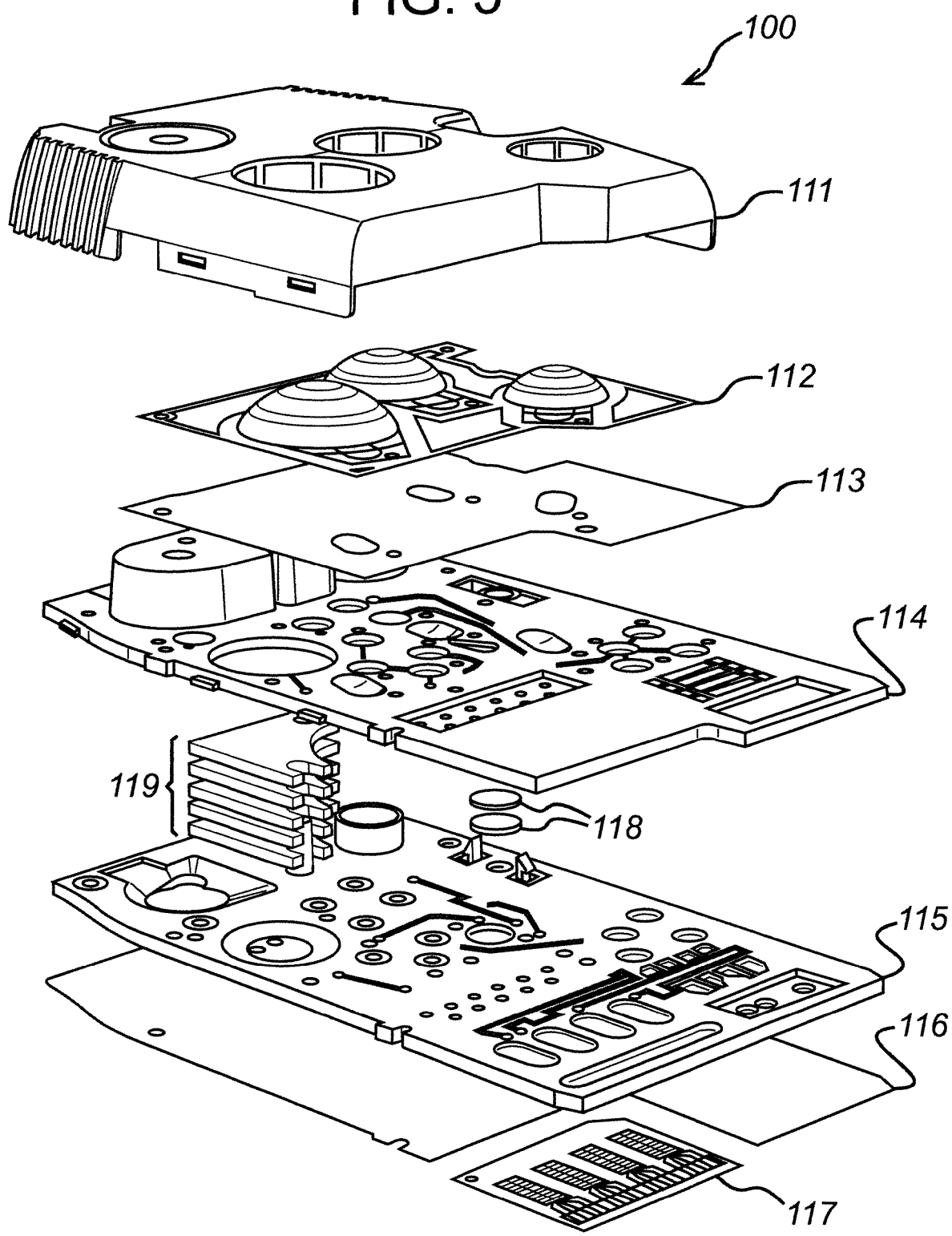
FIG. 3 is an exploded view of the exemplary fluidic cartridge of FIG. 2.

The exemplary cartridge 100 shown in FIG. 2 is formed from various components which shall now be described. FIG. 3 shows an exploded view of the exemplary cartridge 100 of FIG. 2. The cartridge 100 comprises, from top to bottom, a housing 111, a blister sub-assembly 112, a pneumatic foil 113, a pneumatic layer 114, a fluid layer 115 and a fluidic foil 116. Also shown in FIG. 3 is an electrode layer 117, two filters 118 and a plurality of absorbent pads 119, which will be described in more detail below.

The housing 111 is manufactured from acrylonitrile butadiene styrene. The pneumatic and fluidic foils 113, 116 are manufactured from a polyethylene terephthalate/polypropylene composite. The pneumatic and fluidic layers 114, 115 are manufacture from polypropylene.

With the exception of the housing 111, filters 118 and pads 119, each of the components mentioned in the previous paragraph is adhered to its adjacent component or components. Hence, the blister sub-assembly 112 is adhered to the pneumatic foil 113, which is adhered to the pneumatic layer 114, which is adhered to the fluidic layer 115, which is adhered to the fluidic foil 116. The electrode layer 117 is adhered to fluidic layer 115 also.

The adhesion of the layers to each other provides a series of fluid-tight channels in the cartridge, together with associated chambers, valves, pumps, bellows and other components. The channels passing a liquid sample therethrough are liquid-tight and the channels passing a gas therethrough are gas-tight. Optionally, all components are both liquid tight and gas-tight. For example, recesses and openings formed in one or both sides of the pneumatic and fluidic layers create, when sandwiched together and adhered to the pneumatic and fluidic foils, respectively, the shapes necessary to provide the aforesaid channels, chambers, valves, pumps, bellows and other components.

Each of the components referred to above in FIG. 3 will now be described in more detail.

1.3.3 Housing 111

Figure 4:
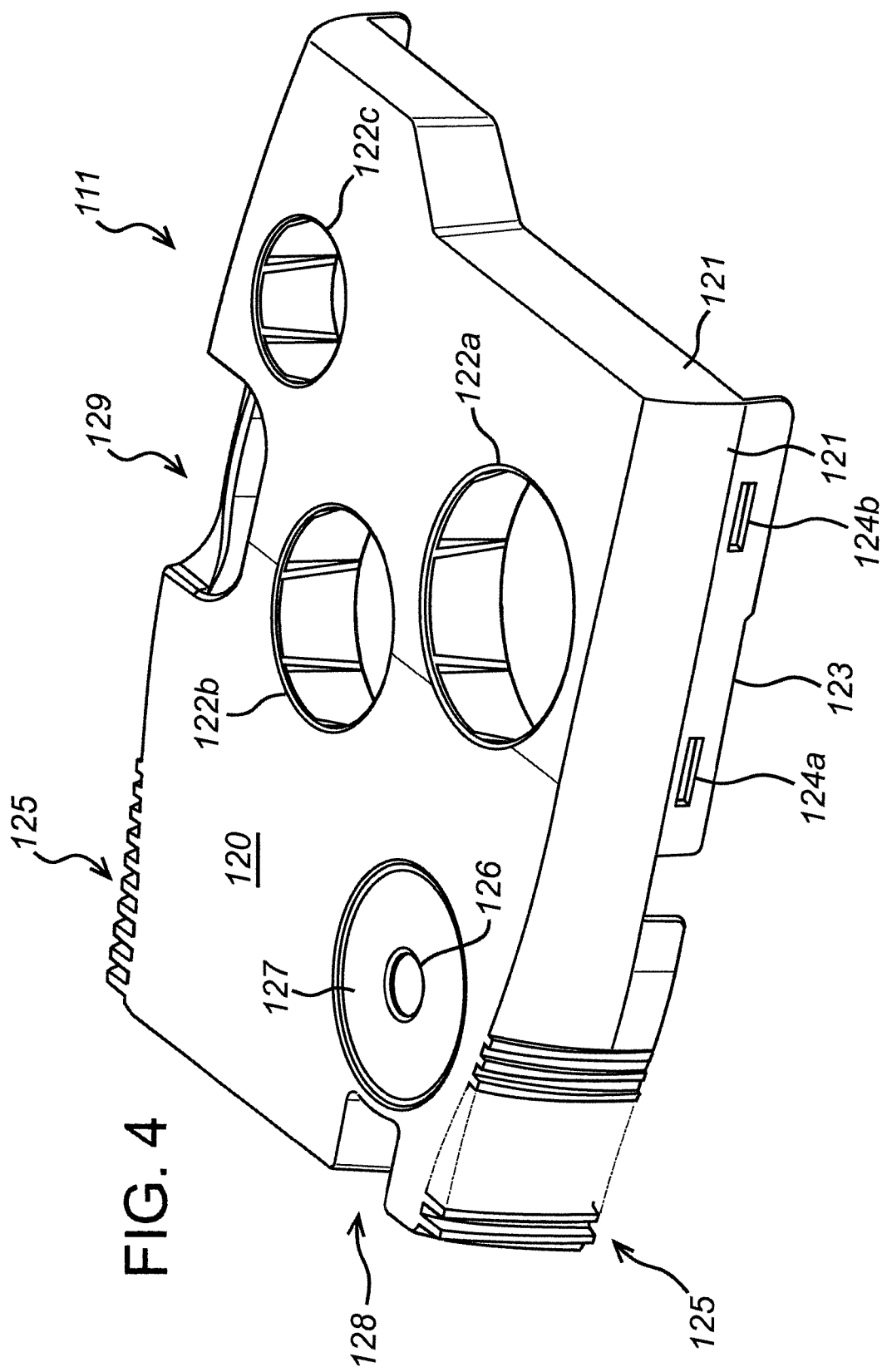
FIG. 4 is a perspective view of the housing of the exemplary fluidic cartridge of FIG. 2.

FIG. 4 shows housing 111 in more detail. As shown, housing 111 comprises a generally rectangular upper surface 120 and walls 121 depending therefrom on all four sides (two of which are visible in FIG. 4). A principal purpose of the housing 111 is to protect certain components of the cartridge, most notably the blister sub-assembly 112 and the isolation valve interface 104. It will therefore be noted that the housing 111 is shorter than the pneumatic and fluidic layers 114, 115 such that it overlies only a portion of those layers when the cartridge 100 is assembled. In the exemplary cartridge 100, the pneumatic interface 101, electronic interface 102, and bypass valve interface 103 are not covered by the housing 111 to provide ease of access by the reader.

The upper surface 120 of the housing 111 has three apertures 122a-c therein, each having walls depending from the peripheries of the apertures to form, when the cartridge is assembled, three recesses. The purpose of the recesses is to house the blisters of the blister sub-assembly 112 such that the blisters may be accessed and pressed by the reader, but are otherwise protected from accidental impact. Naturally, since the exemplary cartridge comprises three blisters, the housing 111 comprises three corresponding apertures 122a-c forming three corresponding recesses. It will be appreciated that more or fewer blisters, apertures and recesses may be provided, depending on the preferred implementation. Alternatively, the housing 111 could comprise a single aperture forming a single recess housing all available blisters.

The side walls 121 of the housing 111 which run along the length of the housing 111 between the insertion end 105 and the non-insertion end 106 of the cartridge 100 comprise flanges 123 along at least a portion of their lower edges. The purpose of the flanges 123 is two-fold. Firstly, they comprise one or more windows 124a-b for receiving a corresponding number of tabs formed in the pneumatic layer 114 to hold the cartridge 100 together. Secondly, the flanges 123 are dimensioned so as to protrude beyond the lower surface of the fluidic foil 116 when the cartridge is assembled, such that the fluidic foil 116 is suspended above a flat surface on which the cartridge 100 is placed. This prevents accidental damage to the fluidic foil 116 which could otherwise result.

Although in the exemplary cartridge depicted in FIG. 4 flanges 123 are provided along substantially the length of two opposing sides of the cartridge, it will be appreciated that flanges may be provided along three or four edges of the cartridge and still suspend the foil above a flat surface on which the cartridge is placed. Similarly, although the cartridge depicted in FIG. 4 shows flanges 123 extending along substantially the entire length of the edge, a flange which extends only partially along an edge may be provided, or multiple flanges may be provided along each edge.

The housing 111 further comprises, at the non-insertion end 106, a grip 125 to facilitate insertion of the cartridge into and removal of the cartridge 100 from the reader by hand. The grip 125 comprises a series of ridges and grooves formed in the housing 111, but alternative structures to increase friction, such as knurls, are also possible.

The housing 111 further comprises a sample inlet aperture 126 through which a sample may be introduced into the sample mixing chamber 10 of the cartridge 100 using a pipette, for example. Surrounding the inlet aperture 126 for a given diameter is a basin 127 recessed into the upper surface 120 of the housing 111 to accommodate a certain amount of spillage of the liquid sample. Whilst the basin 127 of the exemplary embodiment is substantially flat, it may be sloped toward the inlet aperture 126, such that any spillage drains through the inlet aperture 126.

The exemplary housing 111 further comprises a plurality of cut-outs: a first cut-out 128 forming the sample window 109, and a second cut-out 129 to provide access to the isolation valve interface 104. As with the recesses which protect the blisters, by providing access to the isolation valve interface 104 only through a cut-out 129 in the housing 111, the isolation valve interface 104 is protected to some extent from accidental impact, which could actuate the isolation valve and render the cartridge inoperable.

1.3.4 Blister Sub-Assembly 112

Figure 5:
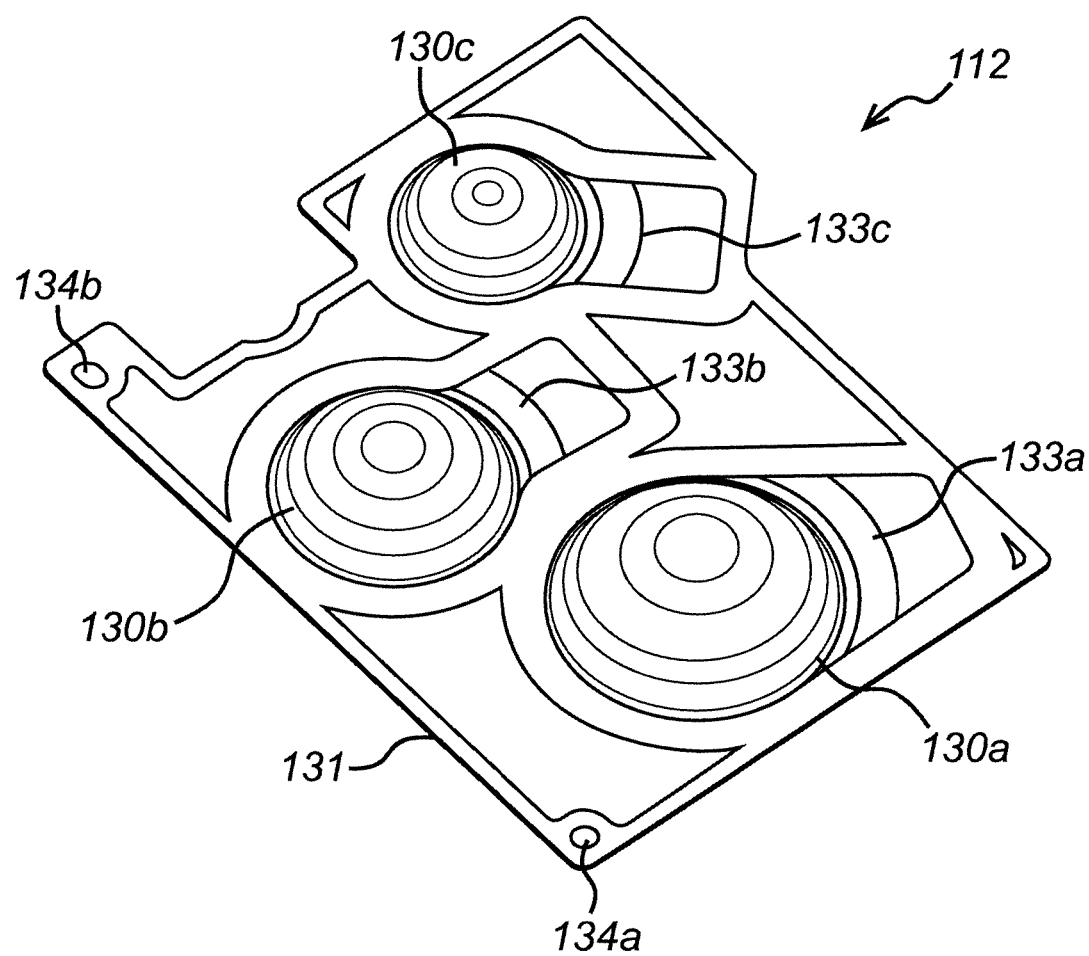
FIG. 5 is a perspective view of the blister sub-assembly of the exemplary fluidic cartridge of FIG. 2.

FIG. 5 shows the blister sub-assembly 112 in more detail. The blister sub-assembly 112 may be manufactured separately, during which the blisters are pre-filled with the liquid reagents necessary for conducting the preferred test, and subsequently adhered to the pneumatic foil 113.

Blister sub-assemblies (or 'blister packs') are familiar to a skilled person. A blister is a collapsible chamber for containing a liquid, which may be expelled from the blister by pressing on the blister and thereby collapsing it. In typical blister packs, the chamber of a blister is sealed by a foil or other frangible layer which ruptures once the pressure inside the chamber reaches a particular magnitude as the blister is collapsed.

In the exemplary cartridge, the blister sub-assembly 112 comprises three blisters 130a-c. These contain, respectively, the lysis buffer which comprises reagents capable of performing cell lysis, the wash buffer and the elution buffer.

The exemplary blister sub-assembly 112 comprises a substrate 131 onto which the aforementioned blisters 130a-c are formed by a deformable polymeric layer which is shaped to provide the chambers. Three apertures 132a-c, corresponding to the three blisters 130a-c, pass through the substrate 132. Each of the apertures is covered by the deformable polymeric layer forming the chamber, which thereby connects the aperture to the chamber but for a seal 133a-c between the respective apertures 132a-c and chambers. Upon application of a suitable pressure on the blister 130a-c, the seal 133a-c breaks, thereby causing the liquid contents of the blister to be ejected from the blister and to flow through the aperture 132a-c in the substrate 131 out of the blister sub-assembly.

As shown, the seals 133a-c at least partially surround the periphery of the chambers, where they meet the substrate 131. At the point in each seal 133a-c which is designed to break (thereby forming the liquid passageway between the aperture 132a-c and chamber), the seal 133a-c may be weaker than the rest of the periphery. This ensures that the correct part of the seal 133a-c breaks when the suitable pressure is applied.

The blisters may be collapsed by the reader when the cartridge is inserted therein. One or more mechanical actuators (such as a foot) may be applied by the reader into the recess so as to collapse the blister.

The blister sub-assembly 112 further comprises two reference holes 134a-b configured to permit an assembly fixture to provide a reference to facilitate positioning of the assembly during manufacture.

1.3.5 Pneumatic Layer 114

Figure 6B:
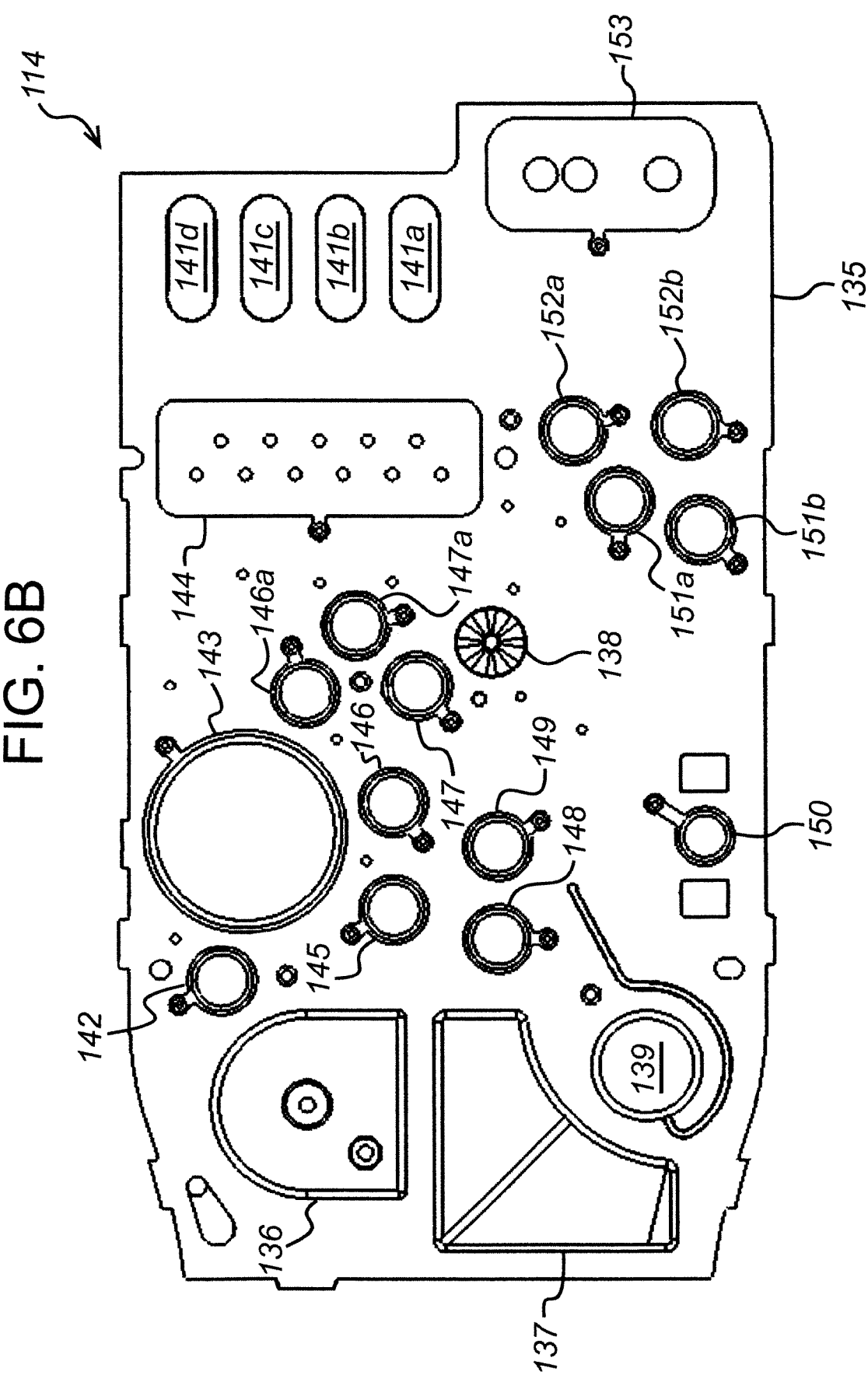
FIG. 6B is a bottom view of the pneumatic layer of the exemplary fluidic cartridge of FIG. 2.

FIGS. 6A and 6B show the pneumatic layer 114 in more detail. FIG. 6A is a top view of the pneumatic layer and FIG. 6B is a bottom view. The pneumatic layer 114 is comprised of a rigid plastic layer 135 which, in certain places, is overmoulded with a plurality of flexible membranes to form certain components when the cartridge is assembled. The flexible membranes are manufactured from a thermoplastic elastomer.

The rigid plastic layer 135 has a plurality of differently-shaped recesses therein and apertures therethrough. In combination with the fluidic layer 115, certain recesses within, and/or apertures through, the rigid plastic layer 135 form a number of components, including: the sample mixing chamber 136; the waste chamber 137; the capture column 138; the elution chamber 139; the first and second amplification chambers 140a-b; and the first to fourth detection chambers 141a-d. An aperture 142 is also provided to give access to the electrode layer 117.

In combination with the overmoulded flexible membranes and the pneumatic foil 113, certain other apertures through the rigid plastic layer form a number of other components, including: the upstream bellows valve 142; the bellows 143; a pneumatic interface 144; the downstream bellows valve 145; the wash buffer inlet valve 146; the wash buffer air inlet valve 146a; the elution buffer inlet valve 147; the elution buffer air inlet valve 147a; the waste chamber valve 148; the elution chamber valve 149; the isolation valve 150; the first and second amplification chamber inlet valves 151a-b; and first and second amplification chamber outlet valves 152a-b. A further aperture, in combination with an overmoulded flexible membrane (but not the pneumatic foil) forms a bypass valve 153.

With the exception of the isolation valve 150 and the bypass valve 153, the valves formed in the pneumatic layer are pneumatically-operable valves. That is, each valve is operable to open and close a fluidic channel in which the valve is located, and this valve is actuated by applying a particular pressure to a pneumatic control line coupled to the valve. The pneumatic control lines are coupled to the pneumatic interface 144, to which the reader has access when the cartridge 100 is inserted therein. Hence, to actuate a given pneumatic valve, the reader merely applies an appropriate pressure to the pneumatic control line associated with that valve to open or close the valve.

The isolation valve 150 and the bypass valve 153 are also actuated by the reader, but mechanically. Again, each valve is operable to open and close a fluidic channel in which the valve is located, but the valve is actuated by applying one or more mechanical actuators (such as a foot) to the valve.

The pneumatic layer further comprises two reference holes 154*a*-*b* configured to permit an assembly fixture to provide a reference to facilitate positioning of the layer during manufacture. When the cartridge is assembled, the reference holes 154*a*-*b* in the pneumatic layer align with the reference holes 134*a*-*b* in the blister sub-assembly.

The pneumatic layer further comprises apertures 155*a*-*c* which, when the cartridge is assembled, line up with apertures 132*a*-*c* passing through the substrate 131 of the blister sub-assembly (through the pneumatic foil, as described below).

1.3.6 Pneumatic Foil 113

Figure 7:
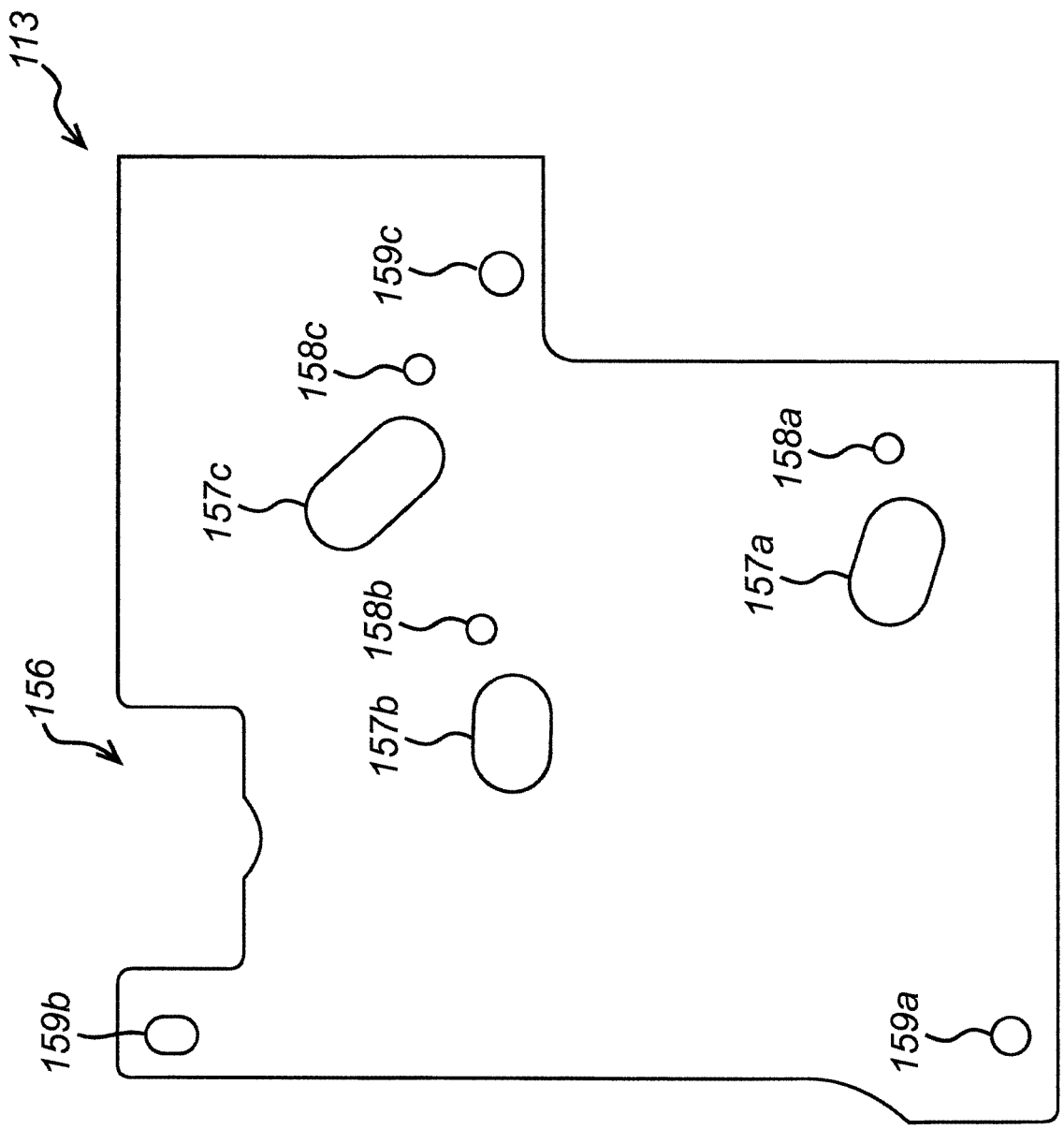
FIG. 7 is a top view of the pneumatic foil of the exemplary fluidic cartridge of FIG. 2.

FIG. 7 shows the pneumatic foil 113 in more detail. As explained above, the pneumatic foil 113 is adhered to the upper surface of the pneumatic layer 114, thereby fluidly sealing channels, chambers, valves, pumps, bellows and other components formed therein. Thus, for the most part, the pneumatic foil 113 is a generally rectangular and planar foil sheet so as to provide an effective seal. Beneficially, the pneumatic foil 113 is inert such that is does not react with the reagents which move through the pneumatic layer 114.

However, the pneumatic foil 113 does not overlie the entire pneumatic layer 114. In particular, the pneumatic foil 113 does not overlie the sample mixing chamber 136 or the waste chamber 137 at the non-insertion end 106 of the cartridge 100, or the bypass valve 153 at the insertion end 105. Moreover, the pneumatic foil 113 comprises cut-outs 156, 157, such that it does not overlie the isolation valve 150 or the pneumatic interface 144, respectively.

The pneumatic foil 113 further comprises three apertures 158*a*-*c* which, when the cartridge 100 is assembled, line up with apertures 132*a*-*c* passing through the substrate 131 of the blister sub-assembly and 155*a*-*c* passing through the pneumatic layer 114. The apertures 158*a*-*c* permit the liquid reagents within the blisters to pass to the pneumatic layer 114, and thence to the fluidic layer 115 through apertures 155*a*-*c*.

The pneumatic foil 113 comprises two reference holes 159*a*-*b* configured to permit an assembly fixture to provide a reference to facilitate positioning of the layer during manufacture. When the cartridge is assembled, the reference holes 159*a*-*b* in the pneumatic foil align with the reference holes in the other layers.

The pneumatic foil is a composite foil manufactured from a layer of polyethylene terephthalate, to provide strength, with a layer of polypropylene on top to provide an inert material for contacting the liquid sample and buffers, and also to enable the foil to be heat sealed to the pneumatic layer (also manufactured from polypropylene).

1.3.7 Fluidic Layer 115

Figure 8A:
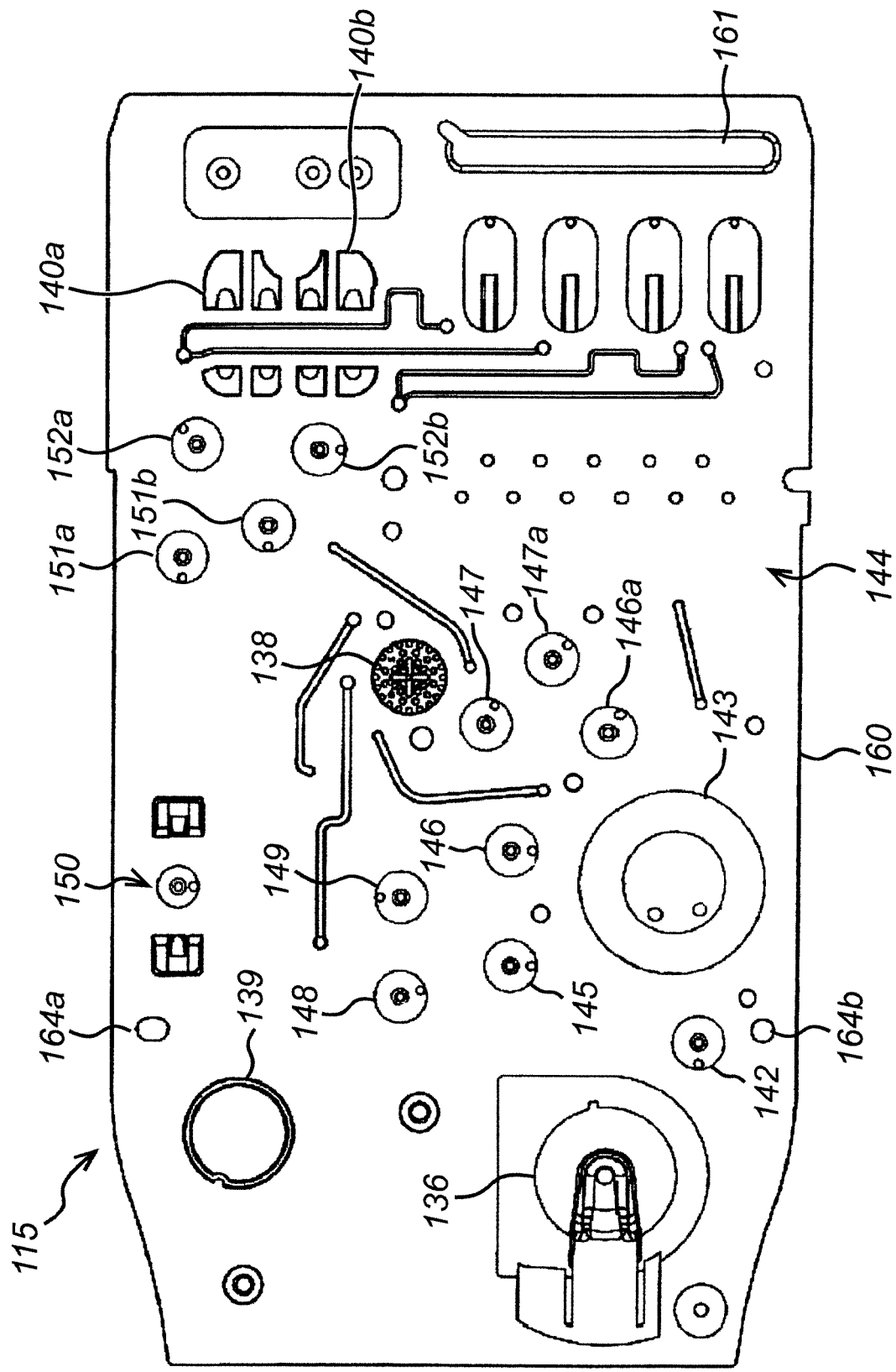
FIG. 8A is a top view of the fluidic layer of the exemplary fluidic cartridge of FIG. 2.
Figure 8B:
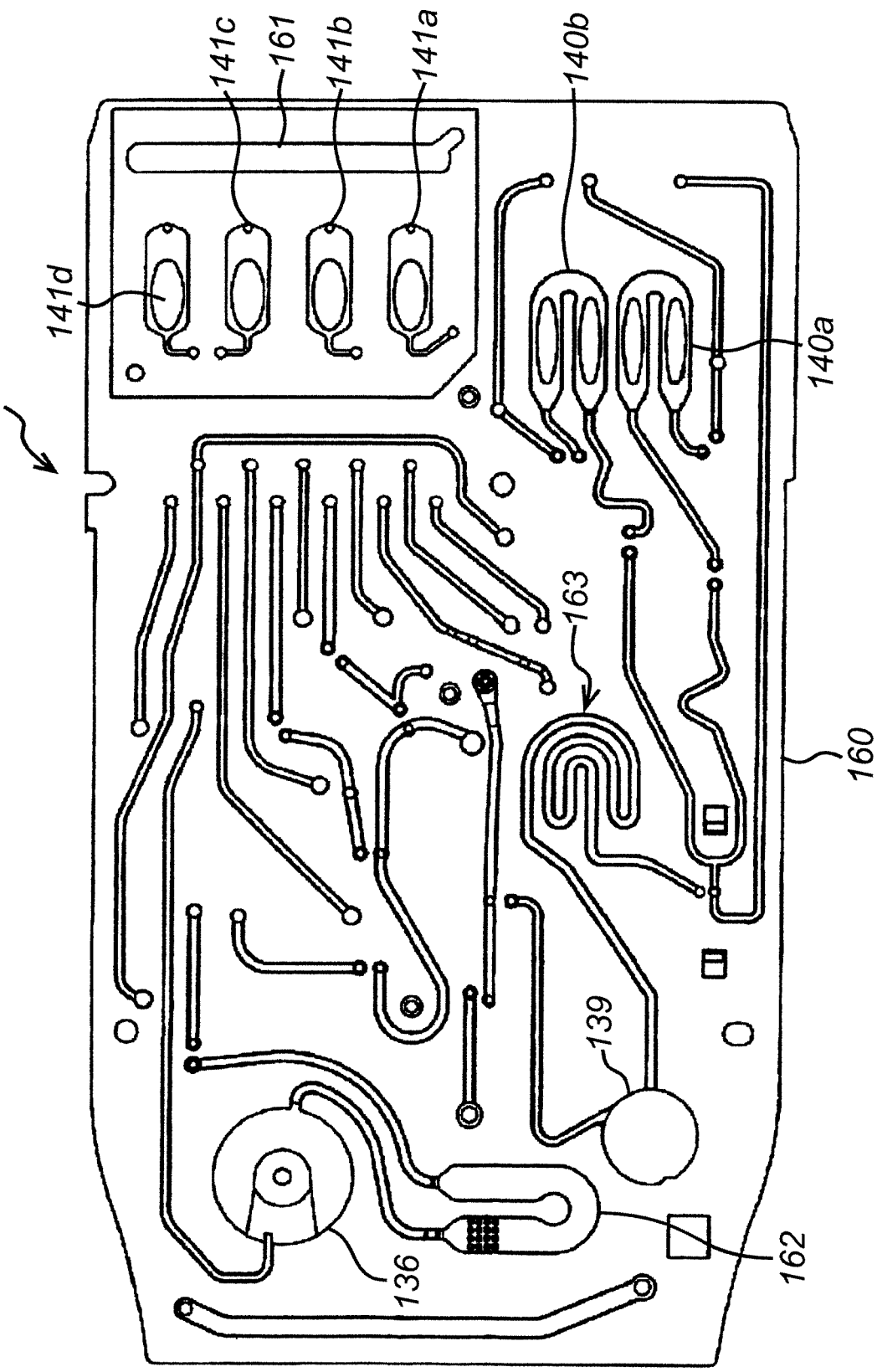
FIG. 8B is a bottom view of the fluidic layer of the exemplary fluidic cartridge of FIG. 2.

FIGS. 8A and 8B show the fluidic layer 115 in more detail. FIG. 8A is a top view of the pneumatic layer and FIG. 8B is a bottom view. The fluidic layer 115 is comprised of a rigid plastic layer 160. As explained previously, the top side of the fluidic layer 115 (not shown) is adhered to the bottom side of the pneumatic layer 113 (see FIG. 5B) such that the various channels, chambers, valves, pumps, bellows and other components formed by a combination of the pneumatic and fluidic layers are aligned.

As with the rigid plastic layer 135 of the pneumatic layer 113, the rigid plastic layer 160 of the fluidic layer 115 has a plurality of differently-shaped recesses therein and apertures therethrough. In combination with the pneumatic layer 113 and the fluidic foil 116, certain recesses within, and/or apertures through, the rigid plastic layer 160 forms certain components, including: the sample inlet chamber 136; the capture column 138; the elution chamber 139; the first and second amplification chambers 140*a*-*b*; and the first to fourth detection chambers 141*a*-*d*. The upstream bellows valve 142; the bellows 143; the pneumatic interface 144; the downstream bellows valve 145; the wash buffer inlet valve 146; the wash buffer air inlet valve 146*a*; the elution buffer inlet valve 147; the elution buffer air inlet valve 147*a*; the waste chamber valve 148; the elution chamber valve 149; the isolation valve 150; the first and second amplification chamber inlet valves 151*a*-*b*; and first and second amplification chamber outlet valves 152*a*-*b*. An aperture 161 is also provided to give access to the electrode layer 117.

Moreover, in combination with the fluidic foil 116 (but not the pneumatic layer 114), recesses in the fluidic layer 115 also provides the coarse filter 162, the convoluted mixing channel 163, and a plurality of channels which, when the cartridge is assembled, connect the aforementioned components together to enable passage of the liquid sample and liquid reagents through the cartridge, and facilitate pneumatic actuation of the valves, pumps, bellows and other components.

The fluidic layer comprises two reference holes 164*a*-*b* configured to permit an assembly fixture to provide a reference to facilitate positioning of the layer during manufacture. When the cartridge is assembled, the reference holes 164*a*-*b* in the fluidic layer align with the reference holes in the other layers.

As mentioned above, channels are formed between the pneumatic interface and the various valve and bellows described above. In the exemplary cartridge, the pneumatic interface comprises 11 ports which are connected to the various components as follows.

Port 1: bellows
Port 2: upstream bellows valve
  first and second amplification chamber inlet valves
  first and second amplification chamber outlet valves
Port 3: downstream bellows valve
Port 4: wash buffer inlet valve
Port 5: wash buffer air inlet
Port 6: wash buffer air inlet valve
  elution buffer air inlet valve
Port 7: elution buffer air inlet
Port 8: elution buffer inlet valve
Port 9: reference pressure line
Port 10: elution chamber valve
Port 11: waste chamber valve It will be understood that whilst various inventive aspects of the exemplary cartridge may be implemented using specific ones of the connections listed above (in particular, the first and second amplification chamber inlet and outlet valves being connected to a single port; and the wash and elution buffer air inlets being connected to a single port); the precise configuration listed above is not essential.

1.3.8 Fluidic Foil

FIG. 9 shows the fluidic foil 116 in more detail. As explained above, the fluidic foil 116 is adhered to the lower surface of the fluidic layer 115, thereby fluidly sealing channels, chambers, valves, pumps, bellows and other components formed therein. Thus, for the most part, the fluidic foil 116 is a generally rectangular and planar foil sheet so as to provide an effective seal. Beneficially, the foil 116 is inert such that is does not react with the reagents which move in the pneumatic layer.

However, the fluidic foil 116 does not overlie the entire fluidic layer 115. In particular, the fluidic foil 116 does not overlie the detection chambers 141a-d at the insertion end 105.

The fluidic foil 116 comprises two reference holes 165a-b configured to permit an assembly fixture to provide a reference to facilitate positioning of the layer during manufacture. When the cartridge is assembled, the reference holes 165a-b in the fluidic foil aligns with the reference holes in the other layers.

The fluidic foil is a composite foil manufactured from a layer of polyethylene terephthalate, to provide strength, with a layer of polypropylene on top to provide an inert material for contacting the liquid sample and buffers, and also to enable the foil to be heat sealed to the fluidic layer (also manufactured from polypropylene.

1.3.9 Electrode Layer 117

Figure 10:
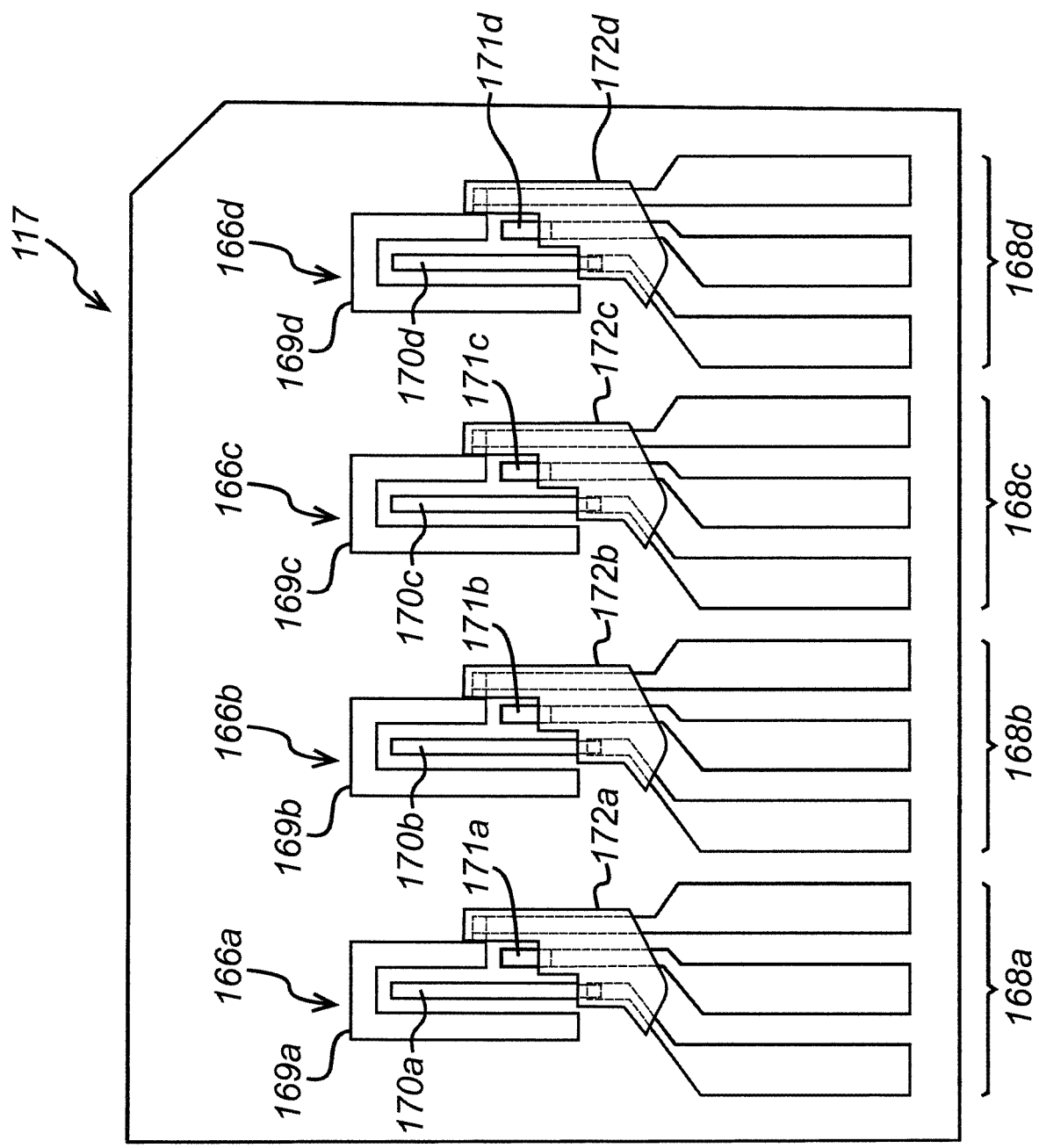
FIG. 10 is a top view of the electrode layer of the exemplary fluidic cartridge of FIG. 2.

Finally, FIG. 10 shows the electrode layer 117 in more detail. As explained above, the electrode layer 117 is adhered to the fluidic layer 115. The electrode layer 117 comprises four sets of detection electrodes 166a-d. Each set of detection electrodes 166a-d comprises first to third electrical contacts 168a-d which couple with corresponding electrical contacts in the reader when the cartridge is inserted therein. Preferably, the electrical contacts are made of silver to optimise the electrical connection. Preferably electrodes which are silver plated with silver chloride are used to ensure a the optimal galvanic behaviour.

Each set of detection electrodes 166a-d comprises a working electrode 169a-d; a counter electrode 170a-d and a reference electrode 171a-d. Each of the electrodes is coupled to a respective electrical contact. Each set of detection electrodes 166a-d also comprises a dielectric 172a-d covering the interface between the electrodes and the respective electrical contacts.

Electrochemical signaling may be used to indicate the presence of genetic or immunohistochemistry targets in a sample. The sample is processed to form an electrolyte which, in practice, may be held in a cell comprising a set of detection electrodes. Upon application of a potential difference across the work electrodes 169a-d and counter electrodes 170a-d in the cell, some compounds in an electrolyte will have a natural tendency to migrate to the electrodes and swap electrons, resulting in a tiny current. All combinations of soluble compounds have some electrochemical activity, and the rate at which this activity occurs enables measurement of the quantity of those compounds. Thus, the presence of different compounds in the sample may be measured by searching for characteristic features of their redox electrochemistry. In particular, the sample may be processed to include labels that are selected compounds that are present if and only if the sample contains target molecules.

In the exemplary cartridge, the electrodes 166a-d are arranged such that a liquid sample within the first to fourth detection chambers 141a-d comes into contact with the first to fourth sets of electrodes 166a-d.

A voltage sweep is applied between the working electrodes 169a-d and counter electrodes 170a-d by the reader.

The current flowing at any given thus-corrected potential difference is measured and provides the signal that is indicative of the label compounds in the sample. Conventionally, the counter electrode is excessively large so that the reaction at this electrode does not limit the current flowing as a result of the reaction of the working electrode, which is the one of interest.

1.3.10 The Isolation Valve

The isolation valve may be implemented in the exemplary fluidic cartridge described above, specifically at the isolation valve 50. As described previously, this isolation valve seals the back end of the microfluidic cartridge and locks in a closed position to prevent any leakage of the sample from the cartridge. In particular, the isolation valve may be positioned downstream of the junction of the mixing channel and the bypass channel, as shown in FIG. 1. Providing an isolation valve which actuates and latches in this location has two key advantages. Firstly, when the valve is closed and locked, no processed material can escape the cartridge. This is particularly important since leakage of processed sample poses a much greater risk of contamination and may lead to false positives in subsequent test runs. Secondly, when the isolation valve is in its locked and closed position, the back end of the cartridge containing the processed sample is a closed system. Once the system is closed, the volume of the system may be increased and a slight negative pressure may be achieved within the back end of the cartridge. This negative pressure provides a further safeguard against leakage and reduces the risk of cross contamination.

Figure 43:
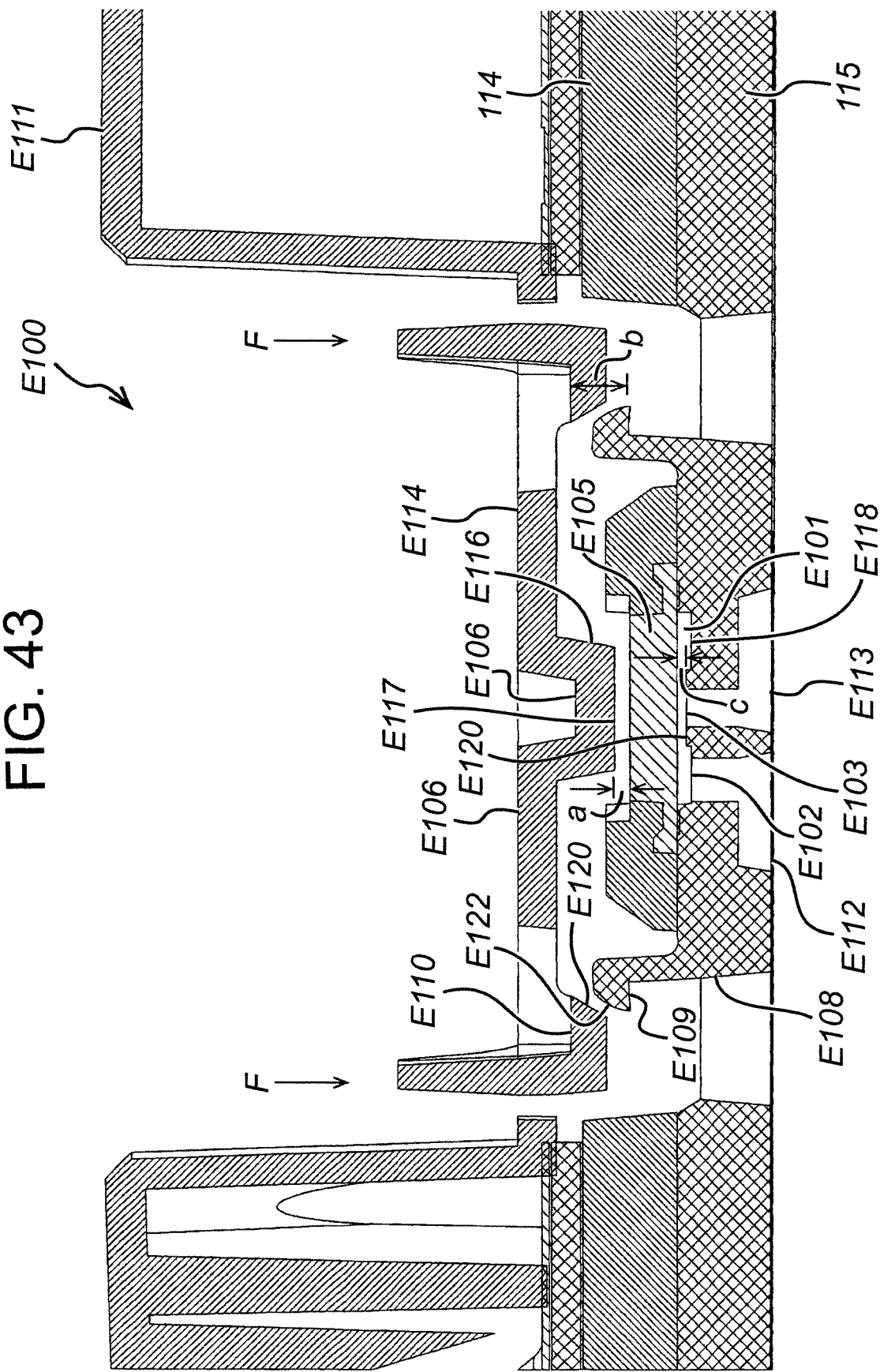
FIG. 43 is a section view of an isolation valve according to an embodiment of the present invention in an open position.
Figure 44:
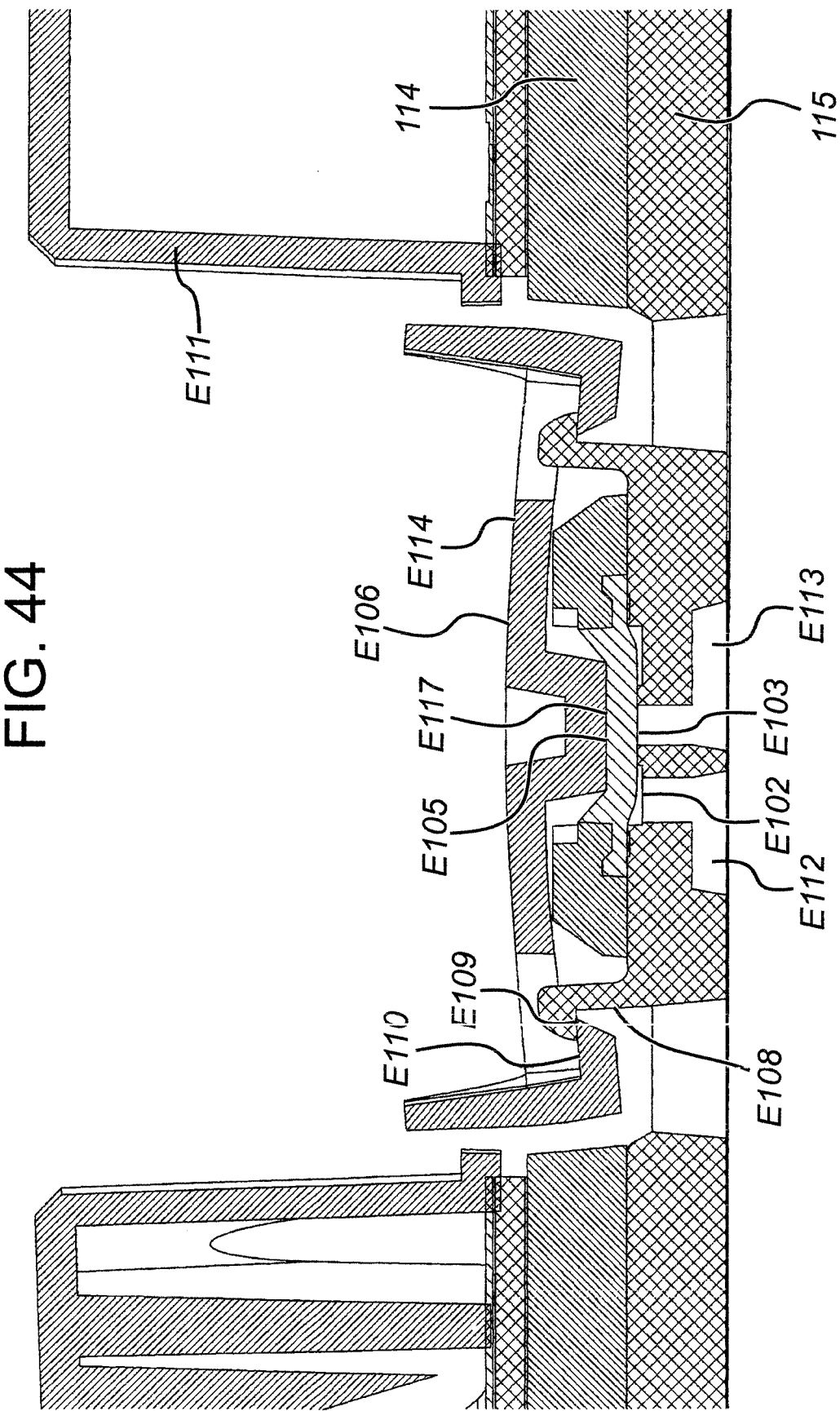
FIG. 44 is a section view of the isolation valve of FIG. 43 in a closed position.
Figure 45:
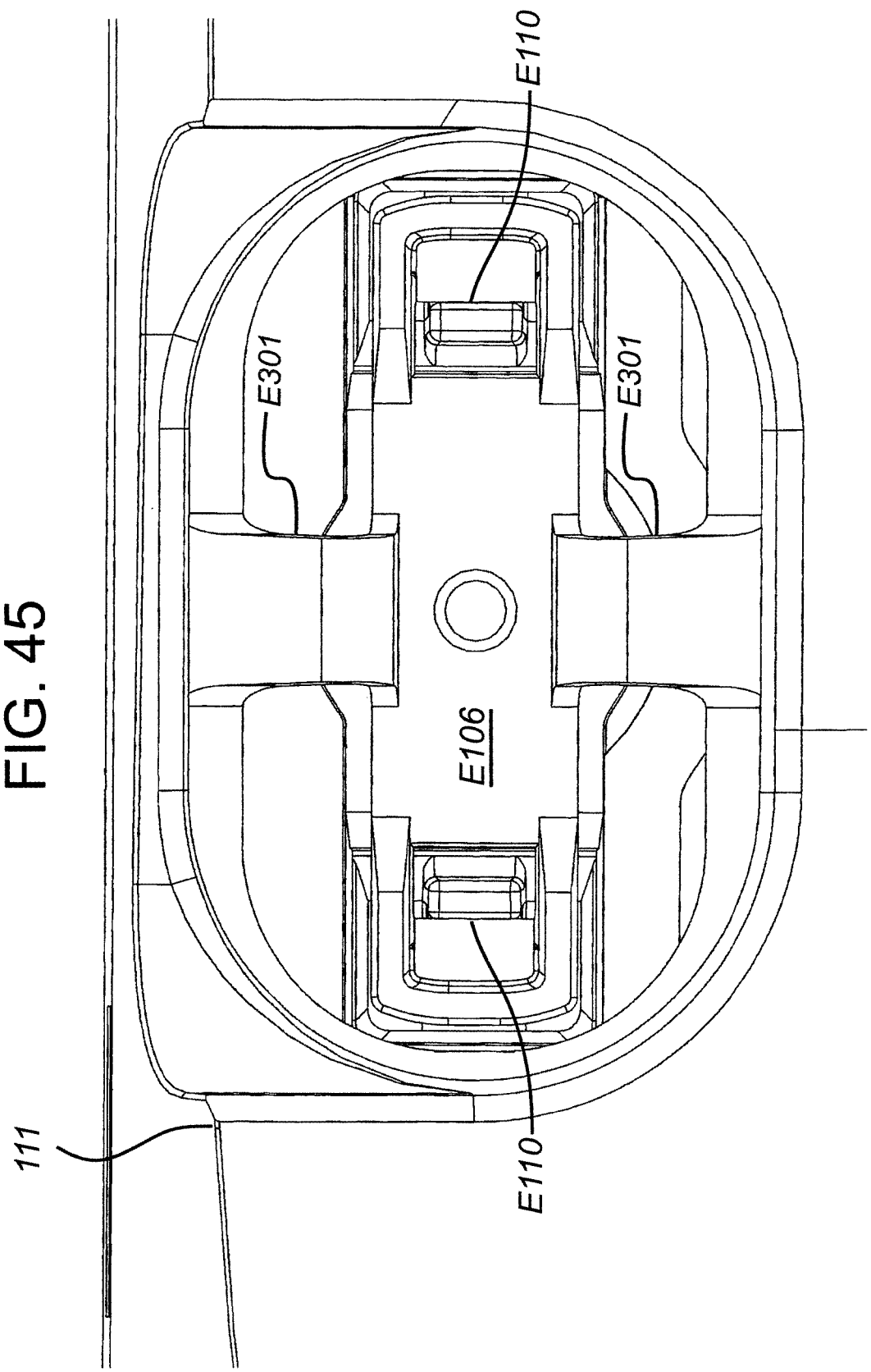
FIG. 45 is a plan view of the isolation valve of FIGS. 43 and 44.

Referring now to FIGS. 43 to 45, valve E100 includes a valve chamber E101, a flexible membrane E105 and an actuator E106. In the exemplary fluidic cartridge, the valve chamber E101 is formed by a recess E118 in the fluidic layer 115, in combination with the flexible membrane E105 which overlies the recess E118. The flexible membrane may be overmoulded onto the pneumatic layer 114, as described above. The actuator E106 is formed as part of the housing 111. However, this particular arrangement is merely preferred, and other implementations are possible.

The valve chamber has first and second openings E102, E103 therein, connected to first and second passageways E112, E113 which, in the exemplary fluidic cartridge, are formed through the fluidic layer 115. At least one of the openings E102, E103 is located on a raised portion E120 of valve chamber E101, which forms a valve seat as shown in FIG. 43 to provide for a better seal against the flexible membrane, although this is merely preferred. Although in the embodiment illustrated in the drawings two openings are shown, it is possible that one, three or more openings may be provided, depending on the particular implementation.

The valve membrane E105 overlies the valve chamber E101 and is movable from an open position, in which valve membrane E105 is spaced apart from the first and second openings E102, E103 and permits fluid to flow between the first and second passageways E112, E113, and a closed position, in which valve membrane E105 seals at least one of the first and second openings and prevents flow between the first and second passageways. When the valve membrane E105 is in its open position, the valve E101 is said to be open, and when the valve membrane E105 is in its closed position the valve E101 is said to be closed.

The valve membrane E105 may be formed of resiliently deformable polymer such that the valve membrane E105 is biased into its open position. In other words, absent the application of any external forces, the valve membrane E105 may occupy the open position illustrated in FIG. 43.

As will be appreciated, the valve membrane E105 is movable from its open position to its closed position by the actuator E106. The actuator is actuated by applying a force on the actuator in the direction of the flexible membrane. The force may be applied by a mechanical actuator in the reader. The actuator E106 includes a protrusion E116, which extends from a crossbeam E114 of the actuator E106 and is adapted to, upon actuation of the actuator, push the valve membrane E105 into the valve chamber E101 toward the first and second openings E102, E103.

The protrusion E116 of the actuator E106 is located in the middle of the crossbeam E114, and has a flat base E117, which engages the flexible membrane E105, with a substantially circular cross-section. This geometry ensures that an even pressure is exerted on the flexible membrane E105 and allows for a good seal to be maintained when the valve is closed, thereby minimising the risk of leakage. However, it will be appreciated that any protrusion geometry may suitable as long as it permits the valve membrane E105 to be moved from its open position to its closed position.

In the embodiment shown in FIGS. 43 and 44, openings E102, E103 are situated in the recess such that the flexible membrane E105 seals against one of the openings in its closed position. However, it is possible to arrange the openings E102, E103 such that they are both sealed by the membrane E105, since this will also prevent flow between the two passageways E112, E113.

Actuator E106 further comprises a latching mechanism which, when the actuator E106 is moved to a position in which the flexible membrane E105 is in the closed position, prevents the actuator E106 from moving back out of that position. By virtue of the latching mechanism, therefore, the flexible membrane E105 is retained in its closed position and cannot return to its open position. This ensures that the valve is closed, and locked in its closed position. Locking the valve such that the flexible membrane E105 is retained in its closed position ensures that leakage of sample from the back end of the cartridge 100 is minimised.

In the preferred embodiment of the isolation valve shown in the drawings, the latching mechanism includes two resiliently deformable latching arms E108 each having a latching projection E109. The latching arms E108 are formed in the fluidic layer of the exemplary cartridge; however the latching arms may be provided anywhere which is convenient for engaging the latching surface. Providing the latching arms in the fluidic layer is advantageous because, when the actuator E106 is latched, it exerts opposing forces against the same component; namely, the pneumatic layer 114 (and the flexible membrane E105 which forms part of the pneumatic layer 114). Thus, no undue stresses are introduced between different layers of the exemplary fluidic cartridge by the forces exerted by the latched actuator E106. However, the latching arms could instead be provided on the pneumatic layer 114, on the housing 111 or elsewhere, depending on the preferred implementation.

Although a pair of latching arms is shown, it will be appreciated that one, three or more latching arms may be used. The latching arms may be distributed evenly about the valve membrane E105 (e.g. two arms spaced apart by 180°; three arms spaced apart by 120°; four arms spaced apart by 90°; etc.). Alternatively, it is possible that one or more latching arms E108 may be distributed unevenly about the valve membrane E105, or even that no latching arms are provided and the body of the fluidic layer 115 itself comprises the latching mechanism. However, by providing two diametrically opposed latching arms E108 either side of the valve membrane E105, an equal pressure may be exerted across the valve membrane E105, and the valve may be securely locked in the closed position.

Latching projections E109 are configured to engage a latching surface E110 of actuator E106. This latching surface may be provided anywhere on the actuator which is convenient for engaging the latching projections E109 of the latching arms E108, or elsewhere on the housing.

In the exemplary embodiment, the latching surfaces E110 are provided at opposing ends of crossbeam E114. The component part providing the latching surface E110 also comprises a beveled surface E120 arranged so as to contact an opposing beveled surface E122 on the latching projection E109.

FIG. 43 shows the latching mechanism E107 in an unlatched position. In this position, the lower surfaces of the latching projections E109 are spaced apart from the corresponding latching surfaces E110 by distance b. Valve membrane E105 is spaced apart from openings E102, E103 by a distance c, and fluid may pass between passageways E112 and E113. In this position, the lower surface E117 of protrusion E116 of the actuator E106 is spaced apart from the upper surface of the valve membrane E105 by distance a. The distance b is larger than distance a+c, the significance of which will be explained below.

Alternatively, the protrusion E116 need not be spaced apart from the valve membrane when the valve is in the open position. It is possible that in the open position, protrusion E116 contacts valve membrane E105 but does not displace valve membrane sufficiently to seal the valve openings.

As explained above, actuator E106 is adapted to be actuated by a foot or feet controlled by the reader. The force applied to the actuator by the foot or feet is preferably applied in a downward direction at the ends of crossbeam E114 above the latching surfaces E110 as indicated by arrows F. Although it may be possible to operate the valve by applying a force to the central portion of the crossbeam, it is preferred to apply the force in line with the latching surface E110 so as to ensure the actuator is properly latched.

As explained above, the reader is preferably configured to actuate the actuator E106 after the device has been used, or during power loss to the reader.

FIG. 44 shows the valve membrane E105 in its closed position. As can be seen, protrusion E116 of the actuator E106 pushes down on the valve membrane E105 to seal at least one of the first and second openings E102, E103 such that fluid is prevented from moving between the two passageways E112, E113. In this position, the upper surfaces of the latch projections E109 engage the latching surface E110 such that the actuator cannot move back to permit the valve membrane E105 to return to its open position. The actuator is thus locked.

It will be appreciated that as actuator E106 is depressed and protrusion E116 of the actuator moves the flexible membrane E105 to its closed position, the beveled surface E122 of latching projection E109 comes into contact with the corresponding beveled surface E120 of the component on which the latching surface E110 is provided. This causes the resiliently deformable arms E108 to deflect inwardly. Once the upper surface of the latching surface E110 moves below the latching projection E109, the resiliently deformable latching arms E108 snap back into their original position such that the latching projections E109 move above the latching surfaces E110, thereby locking the actuator E106.

As shown in FIG. 44, when the actuator is latched, the crossbeam E114 is flexed. This is due to the specific distances a, b and c discussed above. As will be appreciated, upon actuation, the total distance which may be travelled by the protrusion before the valve membrane contacts the fluidic layer is a+c. The total distance which is travelled by the latching surfaces before the actuator becomes latched is b. Providing b>a+c, therefore, the latching surfaces may continue to move downwards (towards the fluidic layer) even after protrusion E116 has pressed valve membrane against openings E102, E103 and may travel no further. This causes the crossbeam E114 to flex elastically when actuator is latched as shown in FIG. 44. The flex in the crossbeam E114 causes the projection to apply a perpetual force against the membrane, thereby ensuring a good seal against the openings and minimising the risk of leakage at all times after the actuator is latched. As b becomes larger relative to a+c, the force which the projection exerts against the membrane increases.

Referring now to FIG. 45, the actuator E106 is held by two resiliently deformable supports E301. It will be appreciated that whilst two supports are preferred, one, or three or more supports may be provided instead. The supports may be shaped in any manner which allows them to be deformed sufficiently to move actuator E106 such that it moves the membrane from the open position to the closed position. For example, the supports may be substantially straight, S-Shaped or have a zig-zag configuration.

As with the crossbeam, the supports are formed in the housing 120. By injection moulding the actuator E106 as a single piece with the housing 120, an effective latch mechanism can be provided without significantly complicating the manufacturing process or increasing costs.

The method operation of the exemplary cartridge introduced above will now be briefly explained.

1.4 Method of Operation of the Exemplary Cartridge 1.4.1 The Front End

As described above, a fluid sample (such as a urine sample) is introduced into the sample mixing chamber 10 using a pipette. A portion of the sample passes to the sample indicator 12 to show that a sample is present in the sample mixing chamber.

Once the cartridge 100 with a sample in the mixing chamber 10 is inserted into a reader, and the reader is activated, the test may commence. Firstly, the reader will apply a mechanical actuator (such as a foot) to collapse the lysis buffer blister 14. In doing so, the lysis buffer will be expelled into the sample mixing chamber 10 where it will mix with the sample.

The bellows 20 and its valves 22a-b then moves the liquid sample and lysis buffer back and forth into the sample mixing chamber 10 so as to mix the lysis and sample and to rehydrate the internal control. Following the mixing step, incubation of the sample and lysis buffer occurs to allow cell lysis to take place.

The bellows 20 and its valves 22a-b will then commence operation to pump the sample from the sample mixing chamber 10, into the main channel 16, through the coarse filter 18 and toward the capture column 24. Within the capture column 24 nucleic acids are specifically bound to a filter in the capture column on the basis of their size and charge. The unwanted liquid sample passes through to the waste chamber 38.

Once the unwanted liquid sample has passed to the waste chamber 38, leaving the nucleic acids bound to the capture column 24, the reader applies a mechanical actuator (such as a foot) to collapse the wash buffer blister 30. In doing so, the wash buffer will be expelled into the first branch channel 26, and thence into the main channel 16. The wash buffer will be flushed into the waste chambers using air from the wash and/or elution buffer air inlets.

Once the wash sample has passed to the waste chamber 38, leaving only the bound and purified nucleic acids in the capture column 24, the reader applies a mechanical actuator (such as a foot) to collapse the elution buffer blister 32. In doing so, the elution buffer will be expelled into the second branch channel 28, and thence into the main channel 16, through the capture column 24 to elute the nucleic acids from the capture column, to the elution chamber 46.

The sample settles in the elution chamber 46 allowing bubbles to disperse before entering the amplification chambers.

1.4.2 The Back End

A controlled pressure is applied to transfer fluid from the elution chamber through the isolation valve 59 to the amplification chambers 56a-b. Any excess liquid sample may be removed from the fluid pathway through the bypass channels 68. In the nucleic acid amplification chambers 56a-d the nucleic acid or acids of interest, if present, is amplified such that it is present at a detectable level. The control nucleic acid is also amplified such that it is present at a detectable level. As mentioned above, any nucleic acid amplification method may be used. Where PCR is used, primers specifically hybridise to the nucleic acid of interest and are extended by a thermostable polymerase such as Taq polymerase via the addition of dNTPs to the 3' end of each of the primers. Before the PCR starts, the valves at the entry and exit to the PCR chambers are closed, isolating the sample, and the detection chambers are vented via the mechanical valve back to the elution chamber which is now vented to atmosphere.

A controlled pressure is applied to transfer the fluid from the amplification chambers to the detection chambers. In the detection chambers, the target probe specifically hybridises to the target amplified nucleic acid of interest and the control probe specifically hybridises to the amplified control nucleic acid. The nuclease hydrolyses the target and control probes following hybridisation of the probes to the amplified nucleic acid. The hydrolysis of the target and control probes frees the labels from the probes causing a detectable change in the signal from the labels to occur.

Once the liquid sample occupies the detection chambers, the reader applies a mechanical actuator to the isolation valve 50 to close the valve and isolate the liquid sample in the back end of the device.

The electrodes provide a potential difference across the at least one detection chamber. Depending on the state of the label (i.e. whether it is attached to the full length probe or the probe has been hydrolysed and it is free or attached to a single nucleotide or short part of the probe), the diffusion rate to the electrode will differ consequently the current that is able to flow through the detection chamber will differ. The electrodes therefore allow detection by the reader of the change in the signal from the label which results from hydrolysis of hybridised probe.

2. The Exemplary Cartridge Reader 2.1 Overview

The exemplary cartridge reader comprises a housing containing: a drawer for inserting a cartridge in to the reader; first and second clamps, adapted to receive and hold the exemplary cartridge therebetween; three blister actuators for actuating three collapsible blisters comprised in the exemplary cartridge; a pneumatics module, comprising a pneumatics interface for interfacing with the pneumatic ports on the exemplary cartridge and at least one pump for providing an appropriate pressure to the pneumatics interface; a thermal module, comprising three thermal stacks for controlling the temperature of three zones within the exemplary cartridge; an electrical interface for electrically connecting to the electrodes comprised in the exemplary cartridge; an isolation valve closing mechanism for actuating a latching isolation valve in the exemplary cartridge; and a mechanical valve actuator for actuating the bypass valve comprised in the exemplary cartridge.

2.2 General Arrangement and Thermal Zones

Figure 11A:
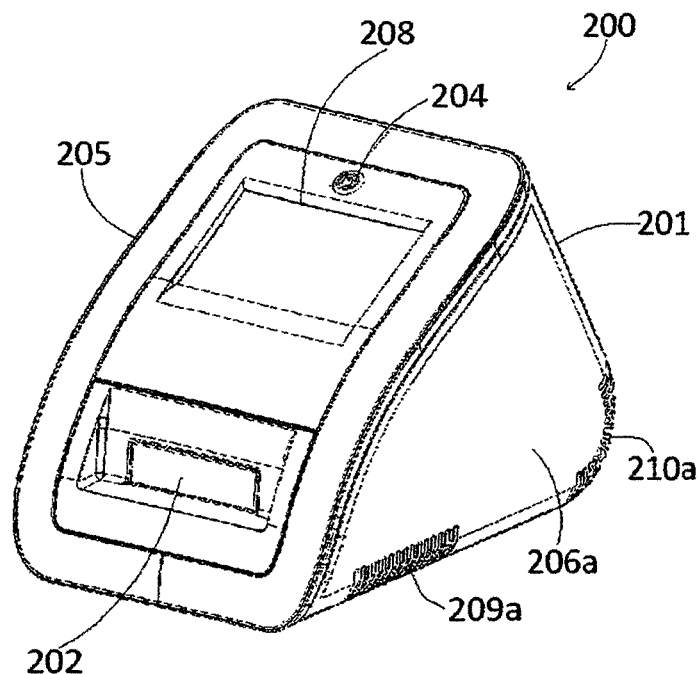
FIGS. 11a and 11b shows a front view of exemplary reader.
Figure 11B:
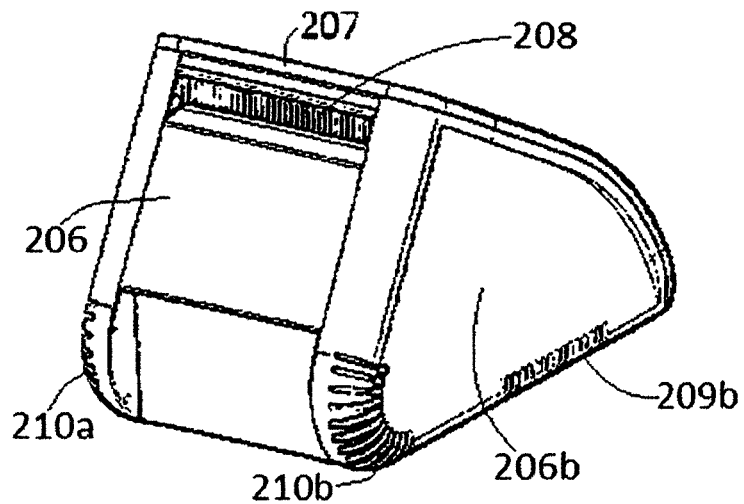

FIGS. 11a and 11b show an external view of a cartridge reader 200 in which the present invention may be implemented. The cartridge reader 200 comprises an outer housing 201, a cartridge drawer 202, a touchscreen display 203, and a power button 204.

The housing takes the form of a triangular prism having a front face 205; a rear face 206 and a base (not shown) flanked by first and second sides 206a, 206b. The front and rear faces of the housing meet at a top edge 207.

Vents are provided in the housing for dissipating heat, and include a first vent 208 in the rear face 206 proximate the top edge 207; second vents 209a, 209b in the base along bottom edges of the housing, more specifically between the base and sides (i.e. where the first and second sides 206a, 206b meet the base); and third vents 210a, 210b in the first and second sides 206a, 206b, more specifically between the first and second sides 206a, 206b and each of the rear face 206 and the base (i.e. where the first and second sides 206a, 206b meet the base and the rear face).

Figures 12A, 12B:
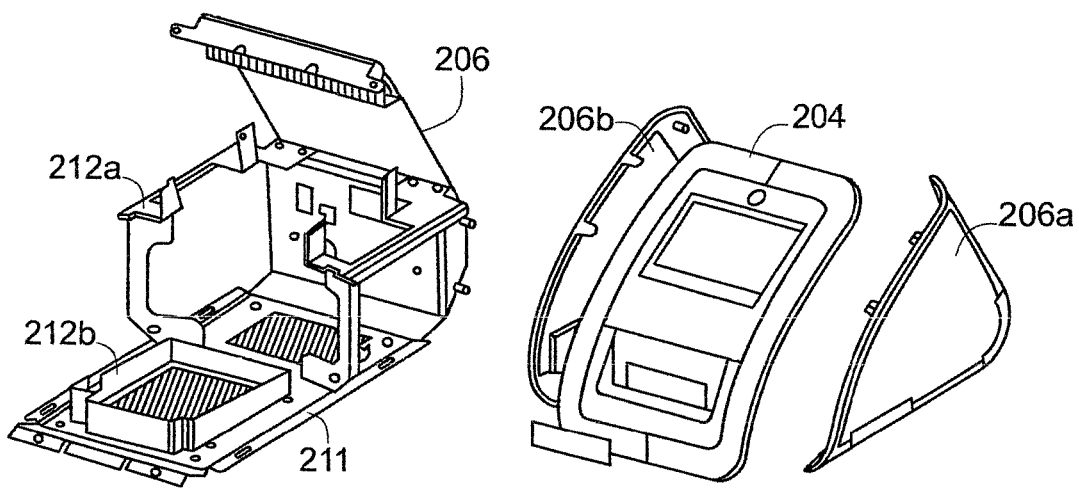
FIGS. 12a and 12b show an exploded view of the housing of the reader shown in FIGS. 11a and 11b.

FIGS. 12a and 12b are exploded diagrams of the housing of FIGS. 11a and 11b. FIG. 12a illustrates the parts of the housing which form the base 211 and rear face 206, which is an integral piece formed (for example) by injection moulding. As shown, within the housing are support structures 212a, 212b that provide support for internal components of the housing and also contribute to the thermal management within the housing, as described in more detail below.

FIG. 12b illustrates the parts of the housing which form the front face 204 and the first and second sides. Each of these parts is formed separately, and is mounted to the remaining components of the housing using suitable fixing means such as screws.

Figure 13:
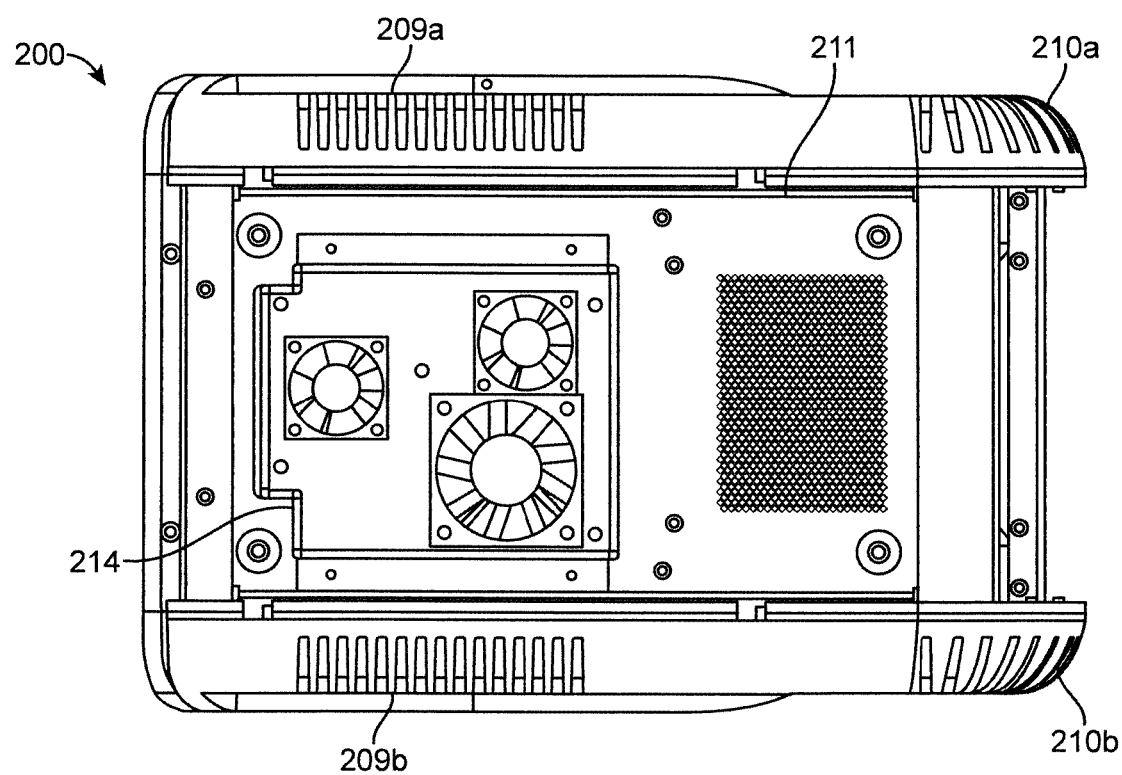
FIG. 13 shows a bottom view of a base of the reader shown in FIGS. 11a and 11b.

FIG. 13 shows the bottom of the base 211 of the housing; second and third vents 209a, 209b, 210a, 210b are clearly visible.

An access panel 214 is provided in the base of the reader 200. The access panel is fixed to the base 211 using suitable fixing means such as screws to allow easy access to the internal components of the reader 200, as described in more detail below.

Figure 14:
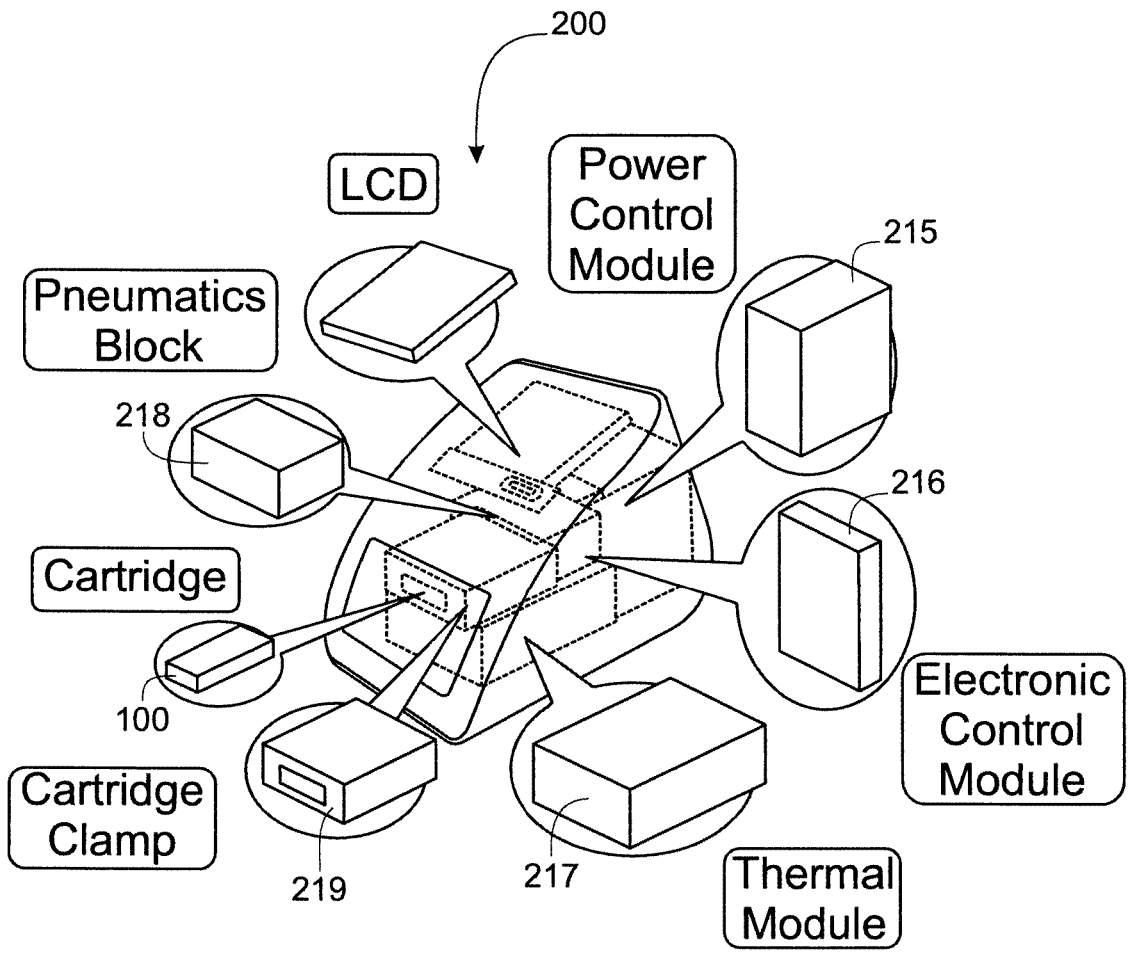
FIG. 14 shows a schematic view of the principal subsystems comprised in an exemplary reader.

FIG. 14 shows some of the principal subsystems of the reader 200. Specifically the reader comprises a power control module 215 for receiving power from an external power supply and distributing the power amongst the components of the reader; an electronics control module 216 for managing the electrochemical detection and analysis of a sample within a cartridge; a thermal module 217 for managing thermal energy supplied to a cartridge during a test; a pneumatics block 218 for managing the delivery of fluid pressure to a cartridge during a test; and a cartridge handling module 219 for receiving the cartridge and clamping it within the housing. Other components illustrated include the touchscreen and a cartridge 100. Other principal subsystems of the reader 200 that are not shown in the figure are the blister actuator system and the mechanical valves actuator system.

Figure 15:
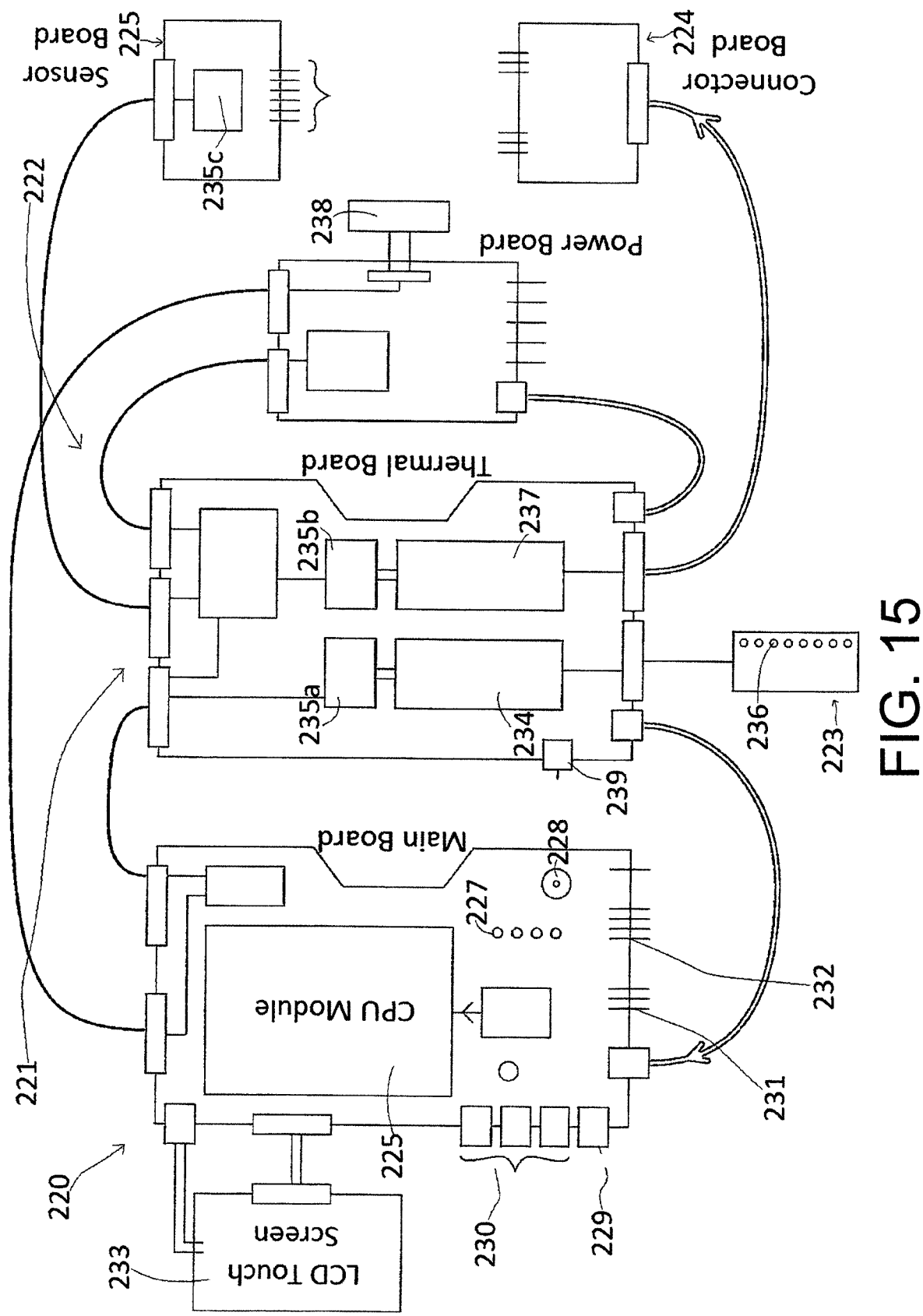
FIG. 15 shows a schematic view of the internal components of the exemplary reader organised onto six boards.

FIG. 15 shows the internal components of the reader organised onto six boards—a main board 220, a thermal board 221, a power board 222, a potentiostat pogo pin board 223, a connector board 224 and a sensor board 225.

The main board 220 provides overall control of the reader. It comprises a CPU module 225 for processing and generating instructions for controlling the remaining components of the reader. The main board 220 also comprises four signalling LEDs 227 and a buzzer 228 for indicating visually and aurally the status of the device; I/O ports including an Ethernet port 229 and three USB ports 230; sensors including three optical sensors 231 and four pressure sensors 232. The main board is also coupled to the LCD touch screen 233 which provides user input for the CPU.

The thermal board 221 comprises potentiostat circuits 234 for applying voltage and detecting current in a detection chamber in a cartridge. The potentiostat circuits 234 are coupled to the main board via an ADC 235a. The potentiostat circuits 234 are also coupled to the potentiostat pogo pin board 223, which comprises twelve pogo pins 236 for coupling to electrical contacts on the cartridge.

The thermal board also comprises peltier drivers 237 which drive the peltier devices on the connector board 224 for applying thermal energy to the cartridge. The peltier drivers 237 are coupled to the main board and to the sensor board via an ADC 235b.

The power board comprises connectors to 7 stepper motors, 18 valves, 2 pumps, 1 solenoid and 1 electromagnet. The power board is also coupled to the barcode engine 238.

The connector board comprises connectors to three peltier devices and three fans. The sensor board comprises six peltier temperature sensors connected to the thermal board via an ADC 235c.

DC power in 239 is provided on the thermal board 221, and it distributed from the thermal board across 24 v power lines 240a-c to the main board, power board, connector board and sensor board. Signal lines 241a, 241b interconnect the main board and the thermal and power boards, whilst signal lines 241c, 241d interconnect the main board and the thermal and power boards.

Figure 16:
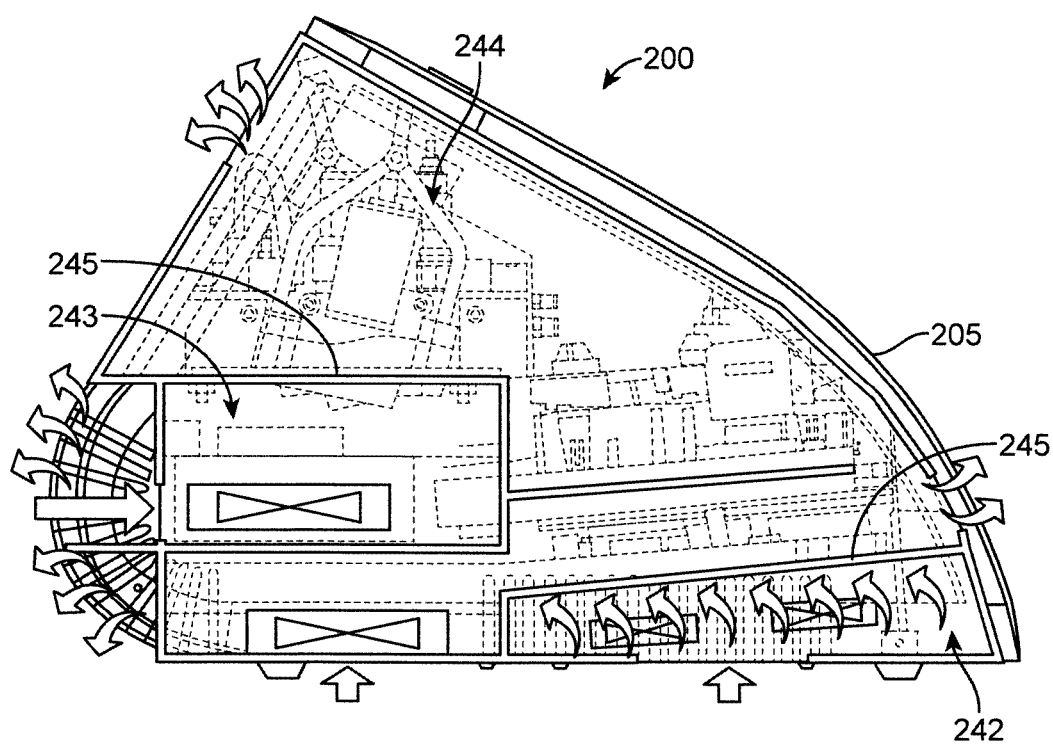
FIG. 16 shows a cross section of the reader of FIGS. 11a and 11b.

FIG. 16 shows a cross section of the reader 200. As can be seen, the reader is partitioned into three thermal zones by thermally insulating walls 245. A first zone 242 is provided at the base of the reader toward the front face 205. The first zone contains the thermal module 217, thereby preventing heat dissipated from the thermal module from entering the second or third zones. In particular, the first zone comprises the three peltiers, three fans and six peltier temperature sensors connected to the connector board.

A second zone 243 contains power control module 215, electronics control module 216, pneumatics block 218 and cartridge handling module 219, as well as the blister actuator system and the mechanical valves actuator system.

A third zone 244 is provided toward the rear face and elevated above the base but spaced apart from the top of the reader. The third zone, which is the coolest zone, comprises the main board.

Each of the first second and third zones comprises a fan for drawing air into the zone before it is expelled from a vent.

2.3 Cartridge Handling

Figure 17A:
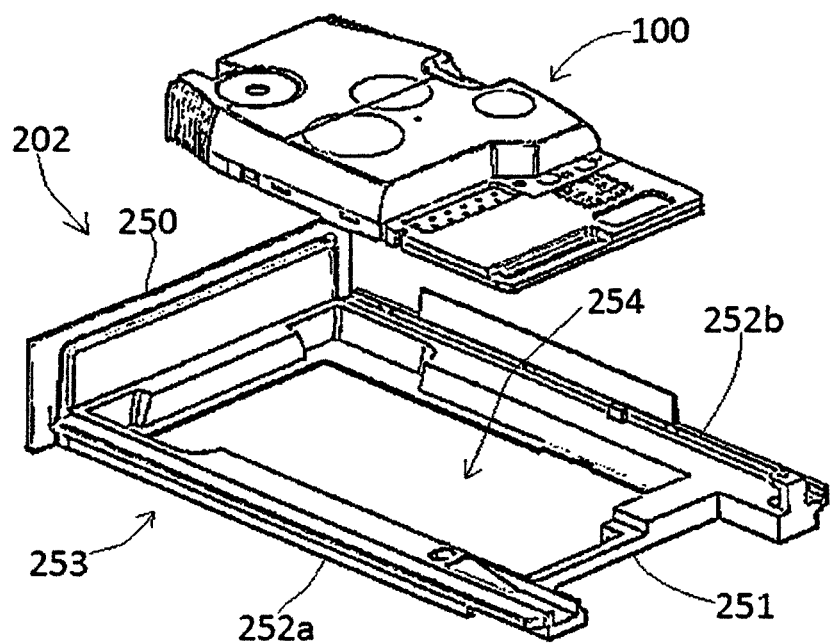
FIGS. 17a and 17b show a drawer of the exemplary reader.
Figure 17B:
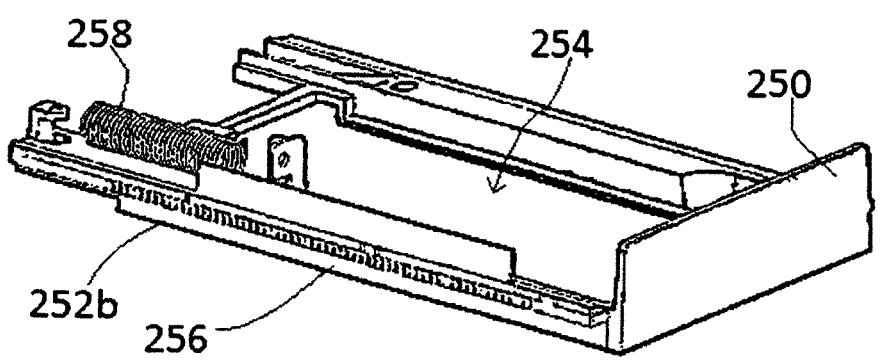

FIGS. 17a and 17b show the drawer 202 of the cartridge reader in more detail. As shown in FIGS. 17a and b, the drawer 202 comprises a front portion 250, a rear portion 251, and first and second side portions 252a, 252b. The first and second side portions connect the front and rear portions, thereby defining the periphery of a cartridge receiving tray 253. A cut-out 254 is provided in tray 253, such that a cartridge inserted into the tray is support around its periphery by the tray 253, whilst substantially all of a lower surface of the cartridge 100 is accessible through the cut-out 254. A vertical rib 256 runs along one of the first and second side portions 252a, 252b. A drawer spring 258, which biases the drawer into an open position relative to the upper clamp is provided above one of the first and second side portions 252a, 252b towards the rear of the drawer 202. As shown in FIG. 17a, the cartridge 100 and the cartridge receiving tray 253 comprise an asymmetrical design such that the cartridge 100 can only be placed in the drawer 202 in the orientation shown in FIG. 17a. In the case of the exemplary cartridge described above, this means that the sample inlet port is located at the front of the drawer 202, whilst the detection and sample processing chambers are located at the rear of the drawer 202.

Figure 18A:
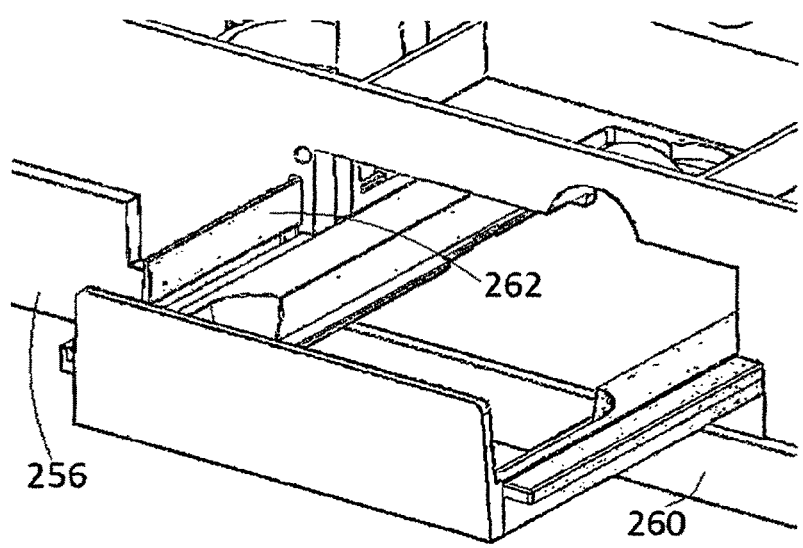
FIGS. 18a and 18b show the drawer of FIGS. 17a and 17b slidably mounted in an upper clamp of the reader.
Figure 18B:
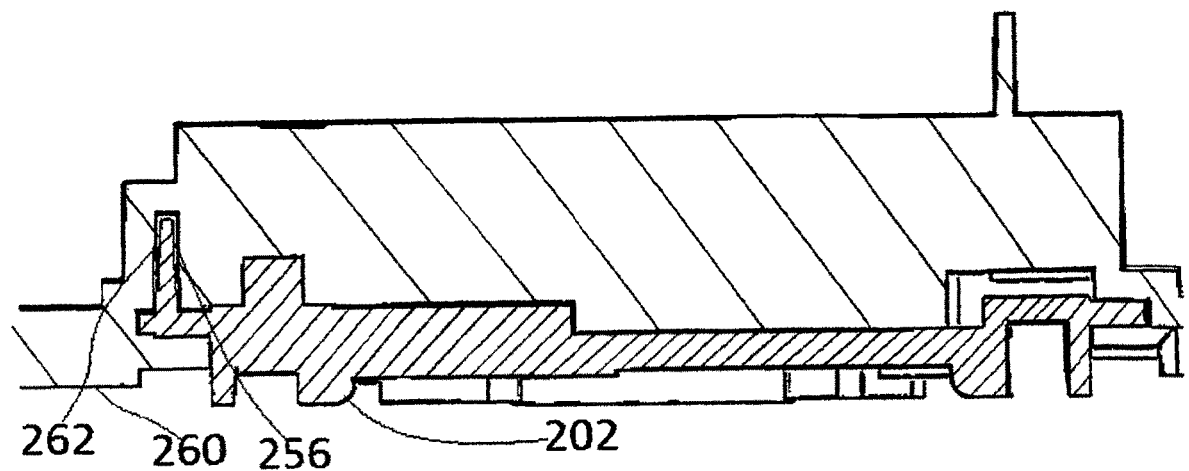

Referring now to FIGS. 18a and 18b, the drawer 202 is slidably mounted in the upper clamp 260. The vertical rib 256 engages a groove 262 provided in the upper clamp 260, thereby restraining movement of the drawer 202 in a first direction relative to the upper clamp 260. The groove 262 narrow towards the rear (for example in the last 20 mm of the drawer closure), thereby tightly aligning the drawer 202 within the upper clamp 260. Adjacent to the rib 256, the drawer 202 also includes a flag feature (not shown) that is viewed by two optical sensors (not shown) rigidly attached to the upper clamp 260. These provide signals that inform the reader's control system whether the drawer 202 is open or closed.

Figure 19:
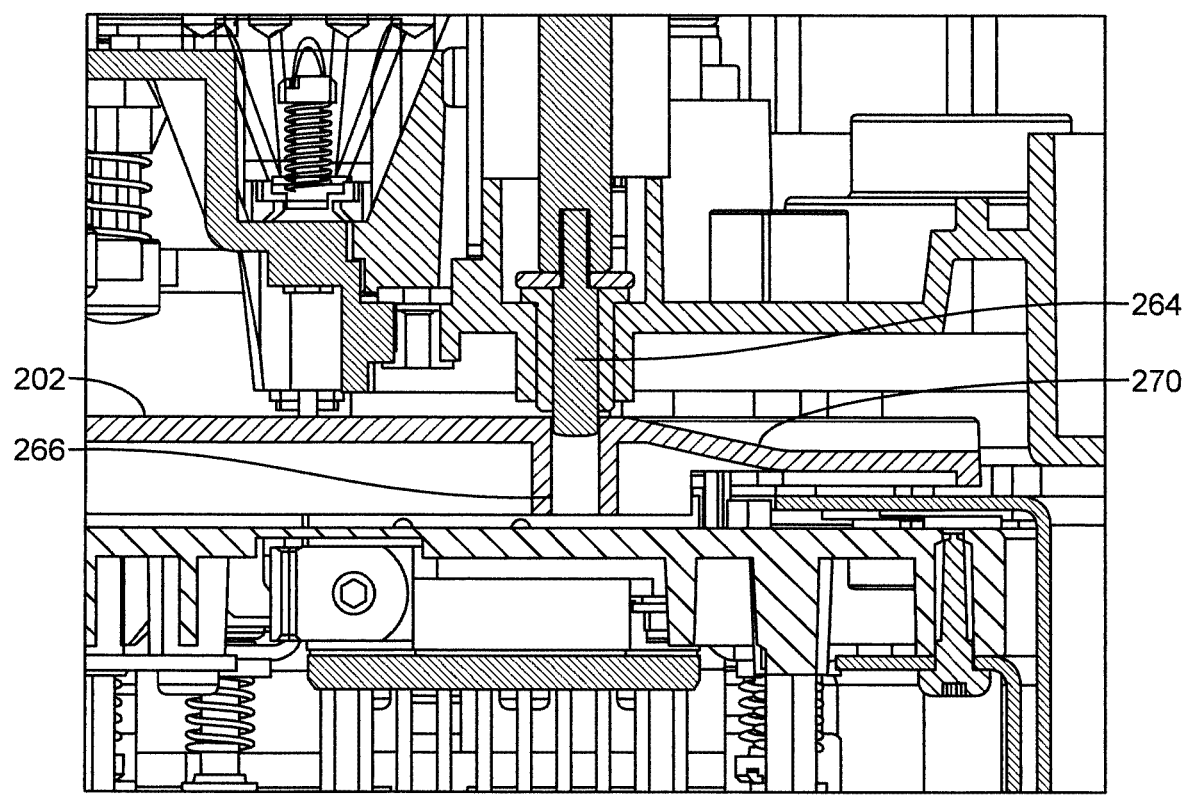
FIG. 19 shows a drawer latching mechanism of the reader.

A drawer latching mechanism is provided between the drawer 202 and the upper clamp 260. Turning to FIG. 19, the drawer latching mechanism comprises a latch pin 264, provided in the upper clamp 260, which aligns with a recess 266 provided in the drawer 202 when the drawer is closed. The latch pin 264 is biased by biasing means (not shown) into a position in which it engages the latch recess 266. A solenoid (not shown) is provided in the upper clamp 260, which can be selectively activated to engage the latch pin 264.

The latching mechanism shown in FIG. 19 holds the drawer 202 closed during a test carried out by the reader 200 and, additionally, whilst the reader is in its inactive state. At an appropriate point during the test cycle (i.e. when an exemplary cartridge 100 is to be inserted or removed), the reader 200 will momentarily active the solenoid, thereby retracting the latch pin 264 from the recess 266. Once latch pin 264 has been withdrawn from the recess 266, drawer 202 opens automatically under the influence of the drawer spring 258. A ramp 270 is provided at the rear of the drawer 202 adjacent to the recess 266. As a user pushes the drawer 202 closed, the latch pin 264 rides over the ramp 270 and reengages the recess 266, thereby resetting the drawer latch mechanism and latching the drawer in its closed position.

Figure 20:
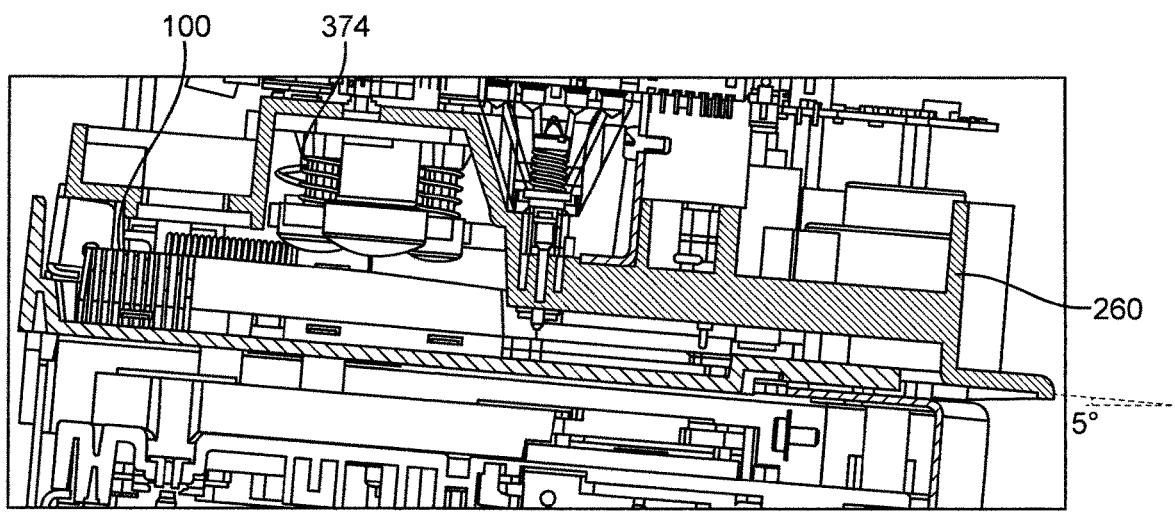
FIG. 20 shows a cross section of an exemplary cartridge inserted into the reader.

Turning now to FIG. 20, the drawer 202 and the upper clamp 250 are positioned at an angle of 5 degrees relative to a horizontal defined by a surface on which the reader is placed. In practice, this means that for an exemplary cartridge 100 inserted into the reader, the sample inlet is located above the detection and sample processing chambers.

Figure 21A:
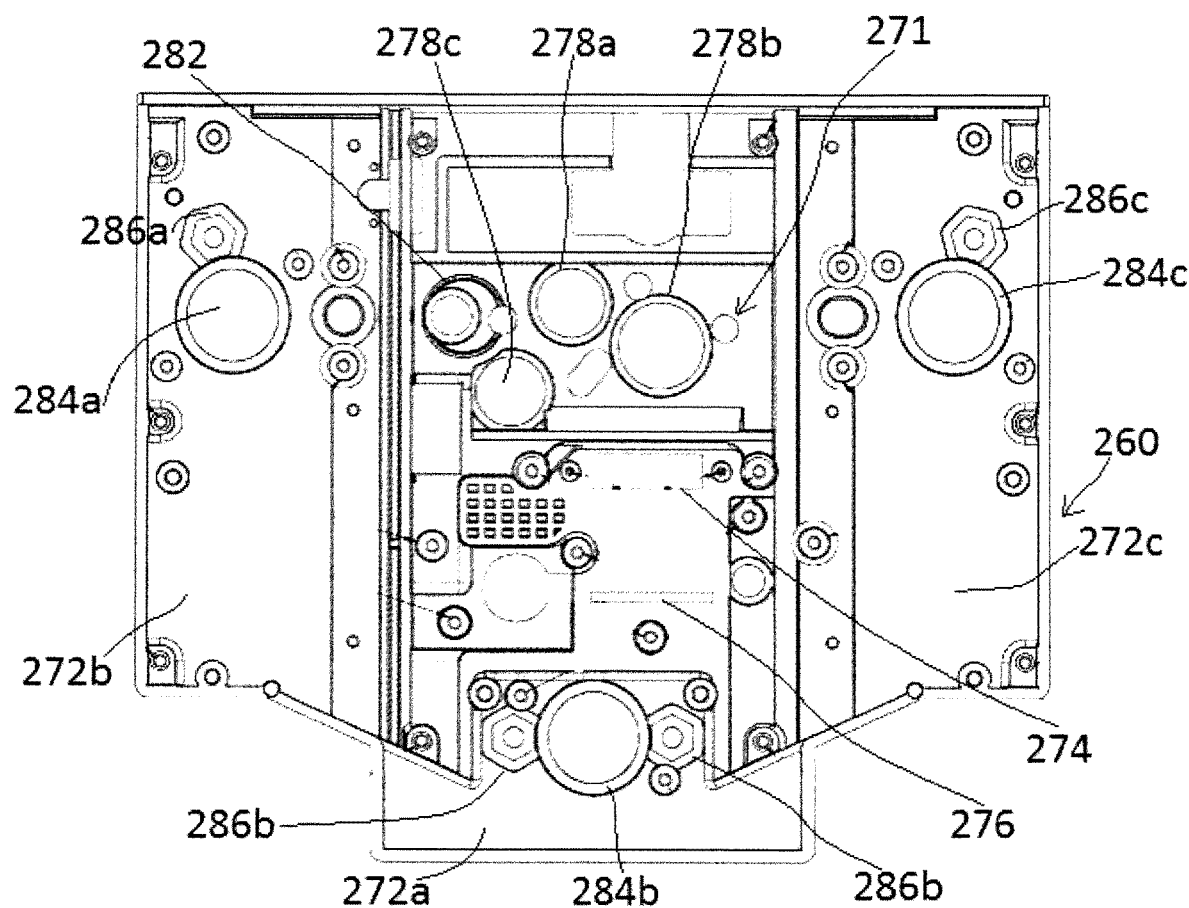
FIGS. 21a and 21b shows a plan view of the upper clamp and the lower clamp respectively.
Figure 21B:
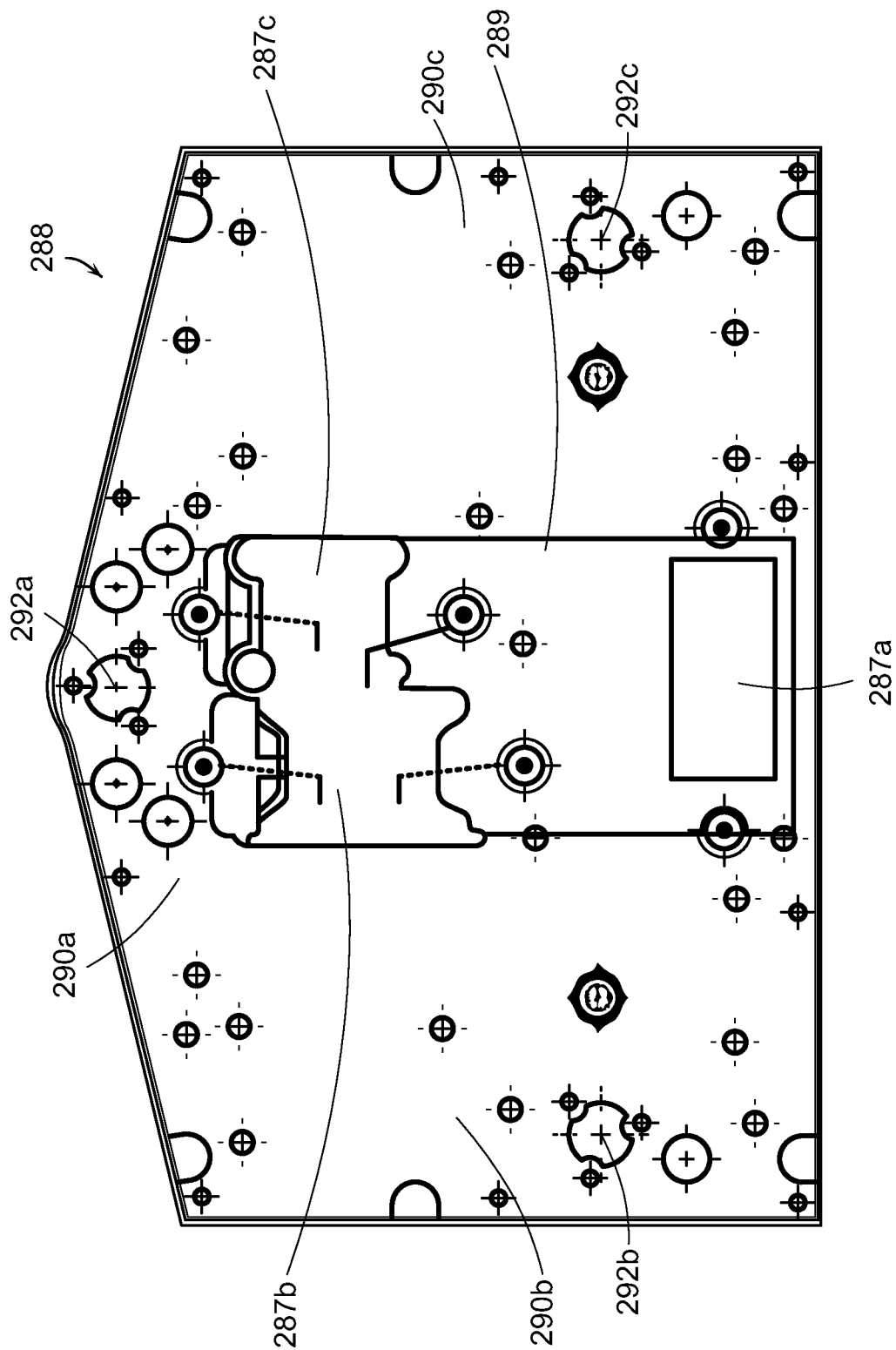

FIGS. 21a and 21b show schematic diagrams of the upper clamp 260 and the lower clamp 288 respectively. As shown in these figures, the clamps contain a number of screw-in inserts that provide fixing points for mating parts. To prevent the risk of the inserts pulling out, the design uses captive inserts that are screwed in from the opposite side to the fixing.

Referring now to FIG. 21a, the upper clamp 260 is fixedly mounted within the cartridge reader 200 comprises a cartridge receiving region 271, a rear portion 272a and two extending side portions 272b-c. The cartridge receiving region 272 comprises: a pneumatics interface 274; an electrical interface 276; first, second and third blister actuators 278a-c; a mechanical valve actuator 280; and an isolation valve actuator 282. First, second and third clamp actuators 284a-c are fixed within the rear and side portions of the upper clamp 260. Each clamp actuator comprises a leadscrew 291a-c driven by stepper motor (not shown). Adjacent each clamp actuator 284a-c, the upper clamp 260 comprises at least one hard stop 286.

Referring now to FIG. 21b, the lower clamp 288 is movable within the cartridge reader relative to the upper clamp and comprises a central raised portion 289, a rear portion 290a two side portions 290b-c extending either side of the central raised portion 289. The raised central portion 289 is dimensioned to fit through the cut out 254 provided in the drawer 202. First second and third clamp actuator nuts 292a-c are mounted in the rear portion and the first and second side portions of the lower clamp 288 respectively. Each of the three clamp actuators nuts 292a-c is threadedly engaged with the corresponding clamp actuator 284a-c mounted in the upper clamp 260. In addition to the above, the lower clamp 288 comprises first, second and third heat stacks 287a-c, which will be described in more detail hereafter.

Figure 22:
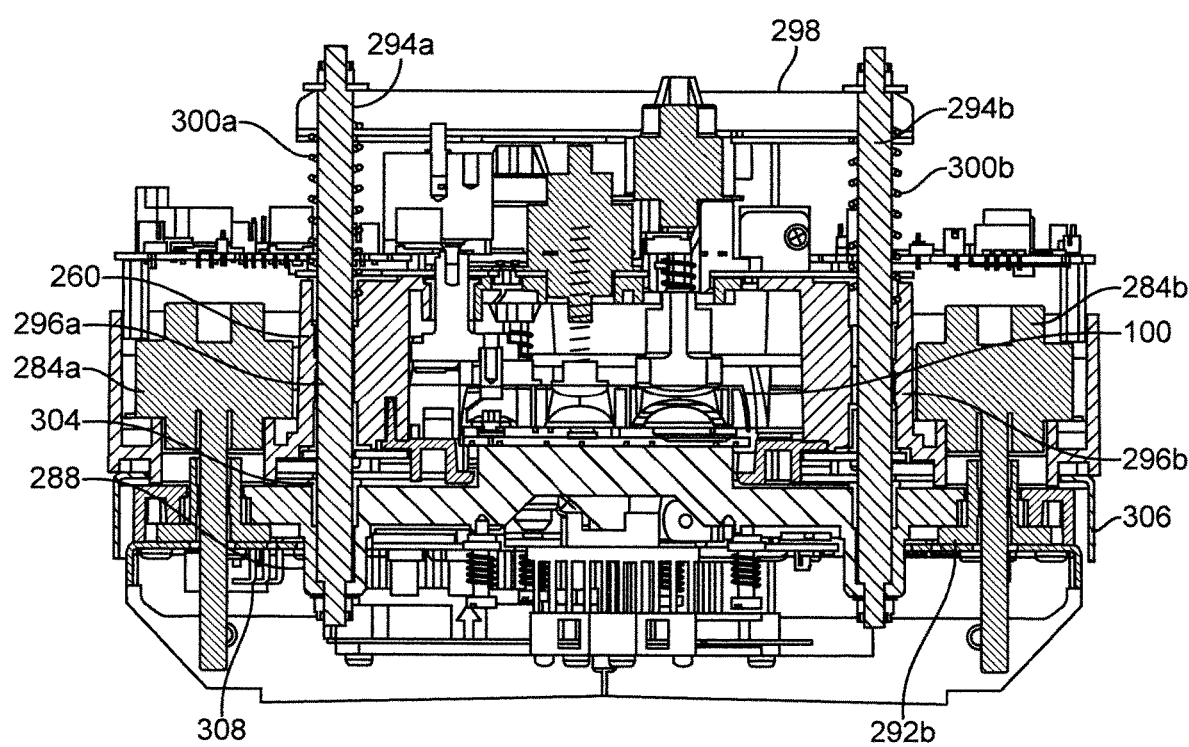
FIG. 22 shows a cross section of a clamping assembly of the exemplary reader.

FIG. 22 show a cross-section of a cartridge 100 clamped between the upper and lower clamps.

The three clamp actuators 284a-c connecting the upper clamp 260 to the lower clamp 288 are clearly shown.

Two static alignment shafts 294a-b are fixedly connected to the lower clamp 288 and pass through two corresponding apertures 296 on first and second side portions of the upper clamp 260. However, a skilled person will understand that more than two alignment shafts may be provided. A gantry 298 is fixedly connected between the two alignment shafts 294 above the upper clamp 260. First and second priming springs 300a-b are provided between the upper clamp 260 and the gantry 298, preferably around each of the static alignment shafts 294. Two location pins 302 protrude from a lower surface of the upper clamp 260, for aligning with two corresponding recesses in an exemplary cartridge 100 inserted into the reader.

Fixed bushes 304 in the lower clamp 288 ensure that the alignment shafts 294 remain perpendicular to the lower clamp 288 whilst the clamp actuator nuts 292a-c are allowed to float in a captive space between the lower clamp 288 and its support bracket 306. At least one moulded stop feature (not shown) in the lower clamp 288 prevents rotation of the clamp actuator nuts 292a-c and the design ensures that the nuts 292a-c only experience vertical forces, not rotational forces that could shear off the posts 308.

During a test, the clamp actuators 284a-c move the lower clamp 288 between three positions: a fully open position, in which each of the three clamp actuators 284a-c stalls against the hard stop features 286a-c comprised in the upper clamp 260, and a fully closed position, in which at least a portion of the upper clamp 260 abuts at least a portion of the upper clamp 260. In the fully closed position, the cartridge 100 is held firmly against the upper clamp 260, thereby engaging the pneumatic and electrical interfaces comprised in the upper clamp with the corresponding interfaces provided on the exemplary cartridge. Preferably, the cartridge is held against the upper clamp with a force of at least 100N, more preferably at least 150N and most preferably at least 200N provided by the clamp actuators 284a-c, via the lower clamp 288.

The movement of the lower clamp relative to the upper clamp throughout an exemplary test cycle will now be described with reference to FIG. 23, which shows a schematic of the steps involved in an exemplary test cycle.

A user initiates a test cycle by requesting a test. Following initiation, the three clamp actuators 284a-c move the lower clamp 288 to the fully open position, defined by a point at which each of the three clamp actuators 284a-c stalls against its corresponding hard stop 286a-c. Once all of the clamp actuators 284a-c have stalled against hard stops 286a-c, the lower clamp 288 is aligned parallel to the upper clamp 260 and the isolation valve latching mechanism is primed. The isolation valve latching mechanism will be described in more detail hereafter.

The lower clamp 288 is then moved to an intermediate 'home' position. In the home position, the lower clamp 288 is spaced apart from the upper clamp 260, and raised central portion 289 of the lower clamp 288 is located beneath the cut-out 254 of the drawer 202. When the lower clamp 288 reaches the home position, the reader activates the drawer de-latching mechanism described, above the drawer 202 opens automatically. Once a user has inserted a cartridge 100 and closed the drawer 202, the lower clamp 288 moves to a fully closed position.

In the fully closed position, the raised central portion 289 of the lower clamp 288 projects through the cut-out 254 in the drawer tray 253, thereby lifting the cartridge 100 out of the drawer 202 and holding in it firm contact with the upper clamp 260. This engages the pneumatic and electrical interfaces on the upper clamp and the exemplary cartridge and aligns the mechanical actuators with their counterparts on the cartridge 100.

Once the test has finished, the clamp actuators 284a-c return the lower clamp 288 to the home position, lowering the cartridge 100 into the drawer tray 253 and the drawer 202 opens automatically for the user to remove and dispose of the used cartridge 100.

The clamp actuator system described above is open loop and relies on positional control of the lower clamp defined by the hard stops 286 comprised in the upper clamp 260 for the actuators to stall against. This technique ensures that the lower clamp 288 is always parallel to the upper clamp 260 at the start of the clamping process and that the fully open position is well defined. However, a skilled person will understand that alternative methods of halting the clamp actuators 284a-c may be provided. For example, the motors may be separately actuated until the clamp reaches optical sensors (not shown) at the required position.

Figure 23I:
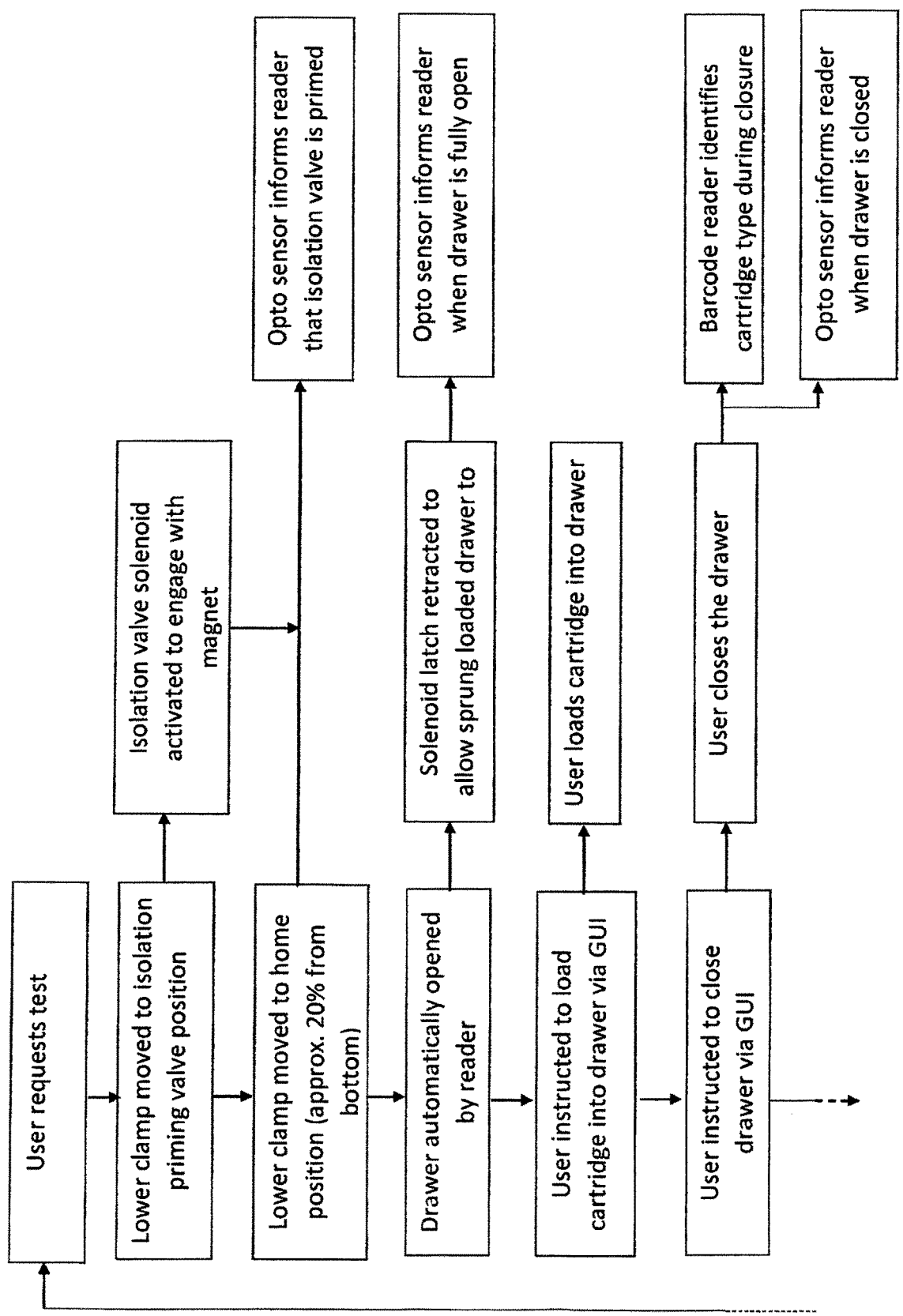
FIG. 23 shows a schematic of the steps performed by the reader during a test cycle.
Figure 23:
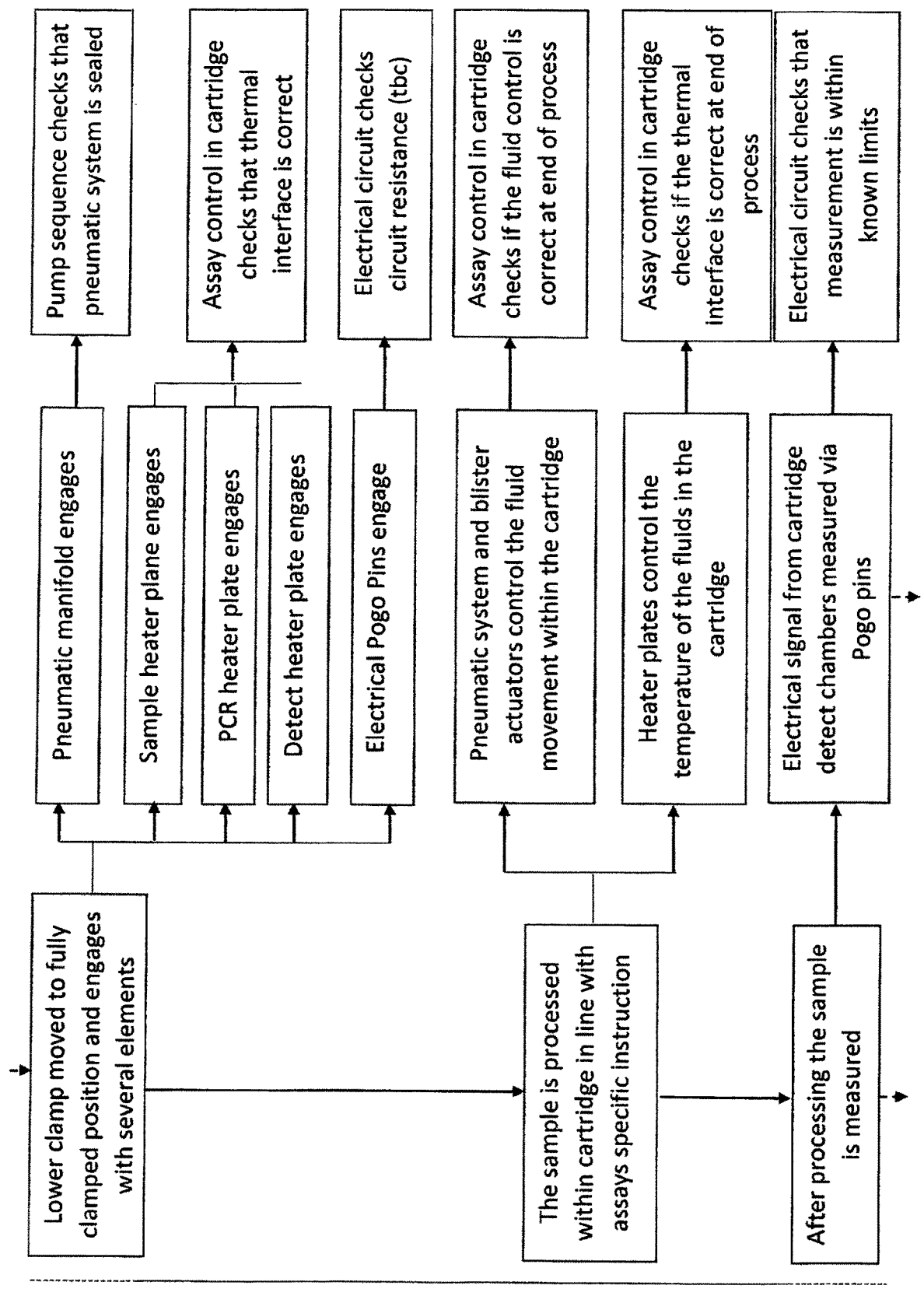

As shown in FIG. 23 in one embodiment, the exemplary reader 200 may move the lower clamp 288 to the fully open position after a test has been completed and before the lower clamp 288 is returned to its home position and the drawer 202 opens for removal of the cartridge. This allows the isolation valve latching mechanism described in further detail hereafter to be re-set ready for the next test, before the used cartridge 100 is removed.

In the exemplary embodiment described above, the upper clamp and the lower clamp are dimensioned such that a distance D between the upper surface of the lower clamp and the lower surface of the upper clamp is approximately 0mm when the lower clamp is in its fully closed position, approximately 7.8 mm when the lower clamp is in its home position and approximately 14.5 mm when the lower clamp is in its fully open position. However, a skilled person will understand that distance D between the upper clamp and the lower clamp may be decided based upon a number of factors. For example, the distance D may be adjusted for different cartridge dimensions, or for different clamp geometries. Moreover, a skilled person will understand that two clamp actuators may be provided, or four or more clamp actuators.

In the exemplary reader described herein, the upper and lower clamp are preferably formed of glass fibre reinforced PBT (Polybutylene terephthalate), each reinforced with a stainless steel bracket. However, a skilled person will understand that other materials may be used for the upper and lower clamps. For example, PPS (Polyphenylene sulfide) or a PC (polycarbonate) may be used.

2.4 Isolation Valve Actuator

Figure 24:
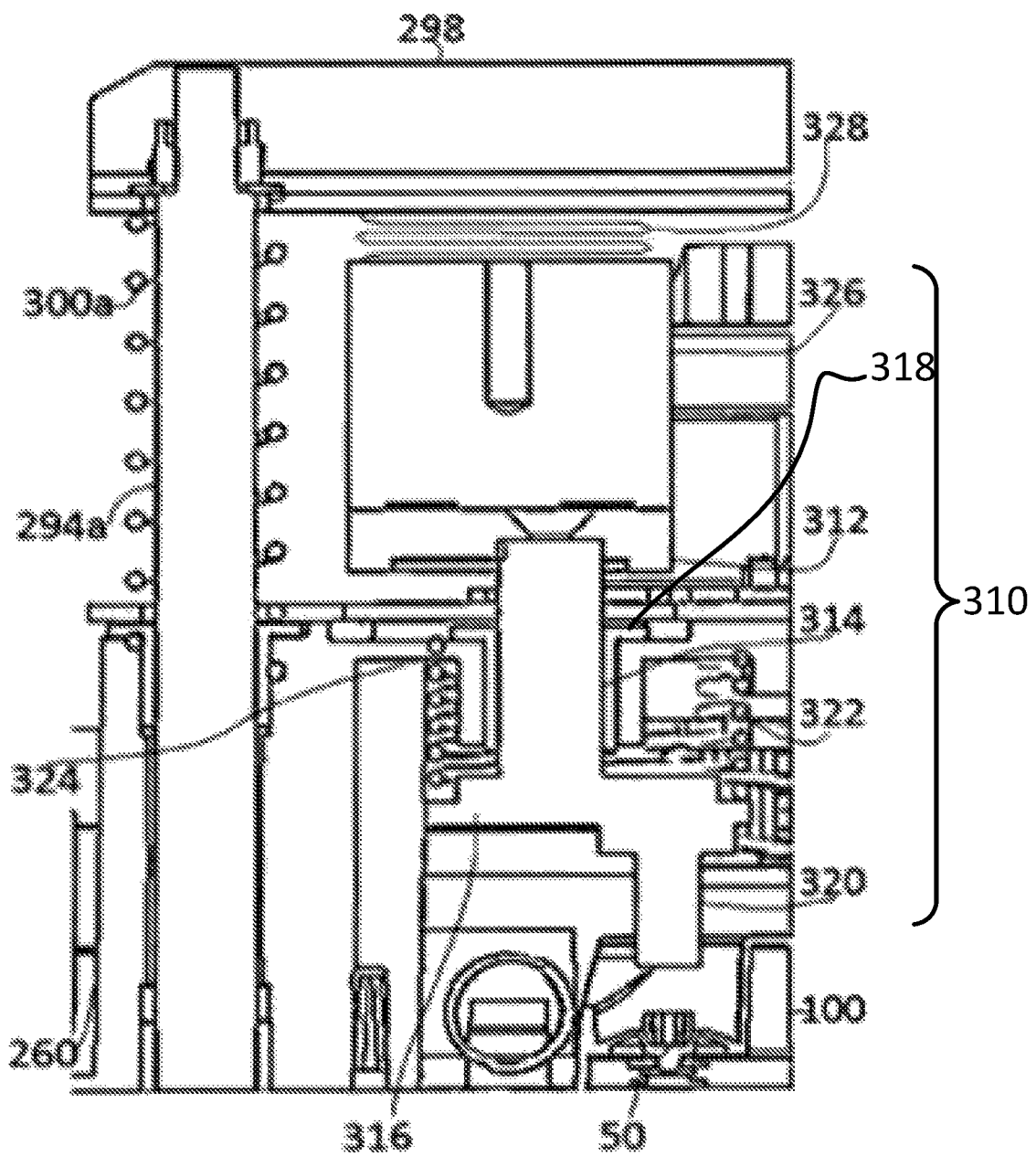
FIG. 24 shows an isolation valve latching mechanism comprised in the upper clamp.

FIG. 24 shows the isolation valve actuation mechanism in more detail. As shown in FIG. 24, the upper clamp comprises an actuation assembly 310. The actuation assembly 310 comprises an armature 312, which may be formed of a ferromagnetic material, comprised above the upper clamp 260 and a second portion 316 comprised below the upper clamp 260, in the cartridge receiving region 271 of the upper clamp 260. A shaft 314 passes through an opening 318 provided in the upper clamp 260 and connects the armature 312 and the second portion 316. A plunger 320, mounted on the second portion 316 aligns with a recess provided in the exemplary cartridge 100, in which the isolation valve 50 is located. The plunger may comprise any shape, but preferably comprises a flat end portion configured to contact a valve actuator of the isolation valve.

An actuation spring 322 is confined between an upper surface of the second portion 316 and a bearing surface 324 provided on the upper clamp 260, such that the actuation assembly 310 is biased downwardly with respect to the upper clamp 260 and into a position in which the plunger 320 actuates the isolation valve 50 on the exemplary cartridge 100. An electromagnet 326 is mounted on the gantry 298 above the upper clamp, in alignment with the first portion of the actuation assembly 290 below. Preferably, a mounting spring 328 connects the electromagnet 326 to the gantry 298.

The isolation valve activation system shown in FIG. 24 is designed to close the isolation valve 50 on the cartridge 100 to reduce the escape of amplified test material. It closes the valve either at the end of the test or event of a power failure.

At the start of the test, the isolation valve activation mechanism is primed by the movement of the lower clamp 288 to its fully open position.

As the lower clamp 288 is moved to the fully open position at the start of the test process, the clamp actuators 284a-c compress and store energy in the two priming springs 300a-b provided around the two alignment shafts 294. The springs 300a-b, are compressed between the upper clamp 260 and the gantry 298 affixed to the lower clamp 288 by the alignment shafts 294. As the lower clamp 288 is moved to its fully open position, the gantry 298 is lowered to a point at which the electromagnet 326, attached to the gantry 298, bottoms out on the armature 312 of the actuation assembly 310. If the electromagnet 326 is spring mounted on the gantry 298, the electromagnet will contact the armature 312 before the lower clamp reaches its fully open position. As the lower clamp 288 moves to the fully open position, the mounting spring 328 is compressed.

The electromagnet 326 is activated to engage the armature 312, such that it pulls the actuation assembly 310 up, compressing the actuation spring 322 when the lower clamp 288 is raised to its home position. When the isolation valve activation mechanism is primed, and the lower clamp 288 is in its home position, the plunger 320 is clear of the recess provided in the exemplary cartridge 100.

Preferably, the vertical force provided by the two priming springs 300*a-b* exceeds the force required to compress the actuator spring. However, a skilled person will understand that no priming springs may be provided or that the vertical force provided by the two priming springs 300*a-b* may be equal to or less than the force require to compress the actuator springs and that the clamp actuators may be configured to provide the force required to overcome the actuation spring as the lower clamp 288 moves to its clamped position.

In the exemplary reader described herein, the electromagnet 326 is activated when the lower clamp reaches its fully open position. However, a skilled person will understand that the electromagnet 326 may be activated slightly before or after the lower clamp 288 reaches the fully open position. Once the isolation valve actuation mechanism has been primed, a cartridge 100 may be inserted into the reader 200, and a test carried out.

At the end of the test (or in the event of power loss) the reader 200 de-energises the electromagnet 326, causing the actuation spring 322 to force the plunger 320 onto the isolation valve 50 in the cartridge 100 below, with enough force to close it. Once the reader has actuated the isolation valve, the valve remains latched closed.

Due to geometry constraints, in the exemplary reader 200, the central axis of the plunger 320 is not in-line with the central axis of the electromagnet 396; however the geometry of the mechanism prevents any jamming of the plunger 320 by ensuring that the forces acting along the actuation assembly 310 from the electromagnet 396 (during priming) and on the isolation valve 50 (during activation) are within the diameter of the actuation spring 322. Clearly, a reader according to the present invention may be provided in which the central axes of the electromagnet, actuation assembly and plunger are substantially the same.

2.5 Thermal Stacks

Referring again to FIG. 21*b*, the lower clamp 288 comprises three thermal stacks 287*a-c*.

Figure 25:
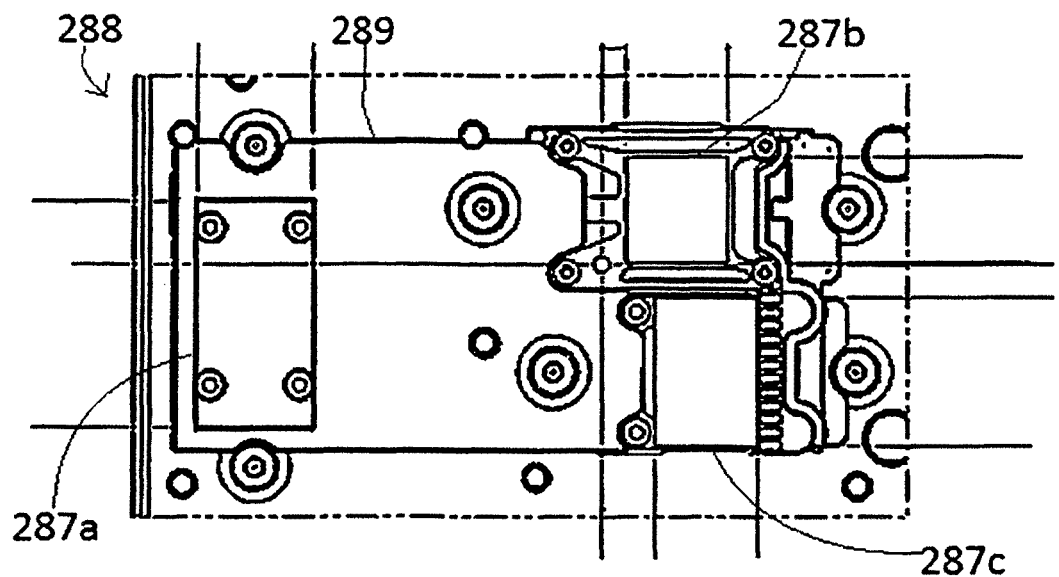
FIG. 25 is a plan view showing first, second and third thermal stacks arranged on the lower clamp of the exemplary reader.

FIG. 25 shows a plan view of the raised central portion 289 of the lower clamp 288, comprising the three thermal stacks 287*a-c*. A first thermal stack 287*a* is provided at the front of the raised portion 289, and is positioned to align with the sample preparation region of an exemplary cartridge inserted into the reader. Second and third thermal stacks 287*b-c* are provided adjacent each other at the rear of the raised portion 289. The second and third thermal stacks 287*b-c* are positioned to align with a sample processing region (for example one or more PCR chambers) of the exemplary cartridge and a detection region of the cartridge respectively. Each of the first, second and third thermal stacks 287*a-c* is aligned with an opening in the lower clamp 288 (shown in FIG. 21*b*) and is configured to contact and exchange heat with the fluidic foil in the region of the cartridge with which it is aligned.

Figure 28:
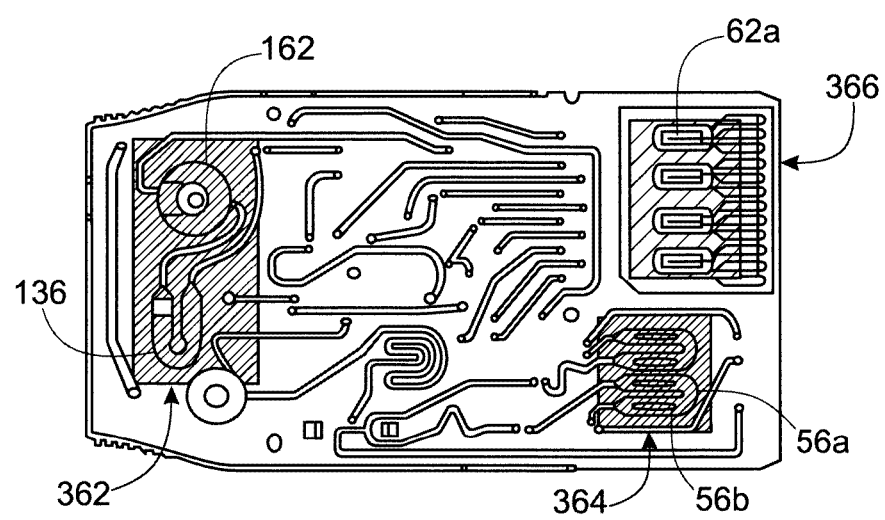
FIG. 28 shows a plan view of the exemplary cartridge with first, second and third zones to heated and/or cooled by the thermal stacks in FIG. 25.

In use, the thermal stacks 287*a-c* are used to contact and exchange heat with the fluidic foil bordering the sample preparation region, the sample processing chambers and the detection chambers, thereby controlling the temperature of the sample within the sample preparation region, the sample processing chambers and the detection chambers. FIG. 28 shows the regions of an exemplary fluidic cartridge that each of the thermal stacks is configured to contact. The first thermal stack is aligned with and configured to contact the fluidic foil in a first region 362, which covers the region of the sample mixing chamber 136 and the coarse filter 162. The second thermal stack is aligned with and configured to contact the fluidic foil in a second region 364 which covers the sample processing chambers, for example a PCR chamber 56*a-b*. The third thermal stack is configured to align with and contact the fluidic foil in a third region which covers the detection chambers 62*a-d*. As illustrated in FIG. 25, in an exemplary reader configured for used with the exemplary cartridge described above, the first thermal stack is configured to contact the foil across an area of approximately 43 mm×22 mm; the second thermal stack 287*b* is configured to contact the foil across an area of 20 mm×20 mm; and the third thermal stack is configured to contact across an area of 28 mm by 20 mm. A distance D between the first thermal stacks and the second and third thermal stacks is approximately 50 mm. A skilled person will understand that these dimensions correspond to a reader designed for use with an exemplary cartridge and that the size and location of the first second and thermal stacks may be modified accordingly to align with and contact the required regions of an alternative fluidic cartridge.

Figure 26A:
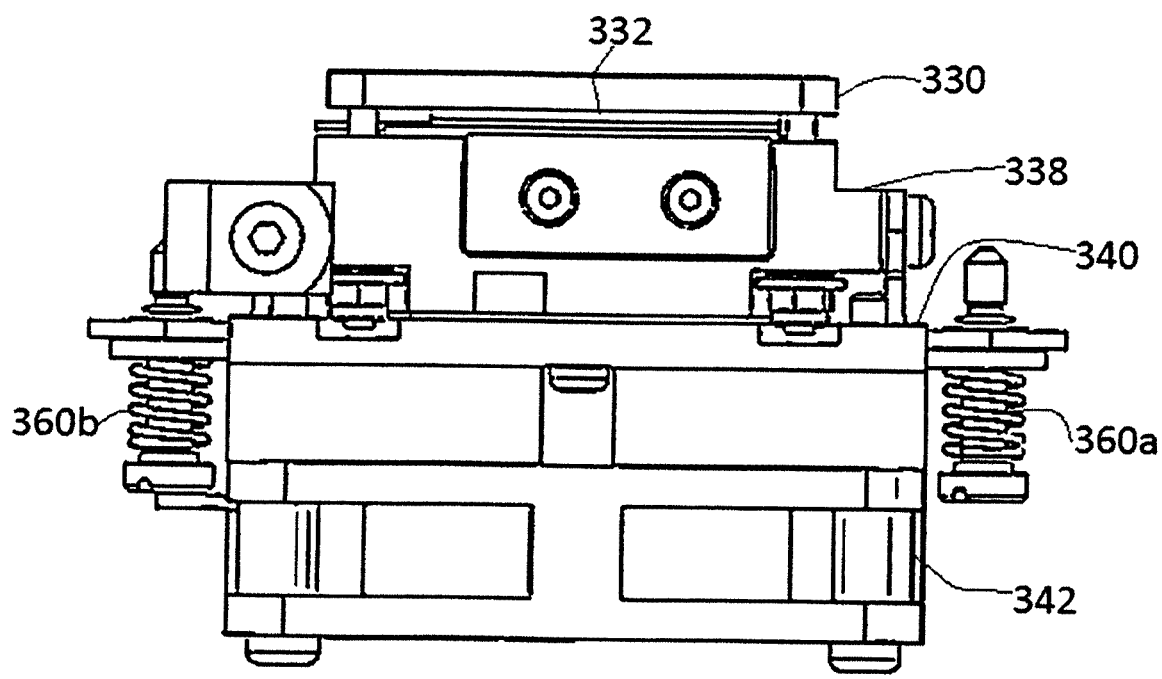
FIGS. 26a-c show a thermal stack comprised in the exemplary reader.
Figure 26B:
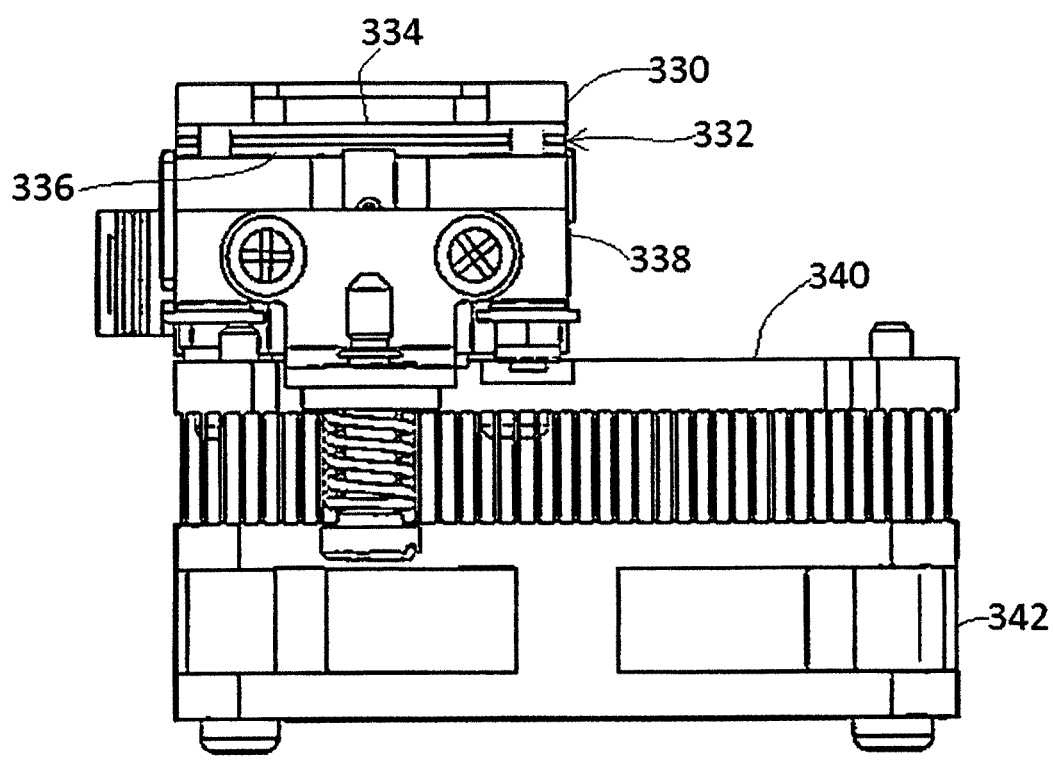
Figure 26C:
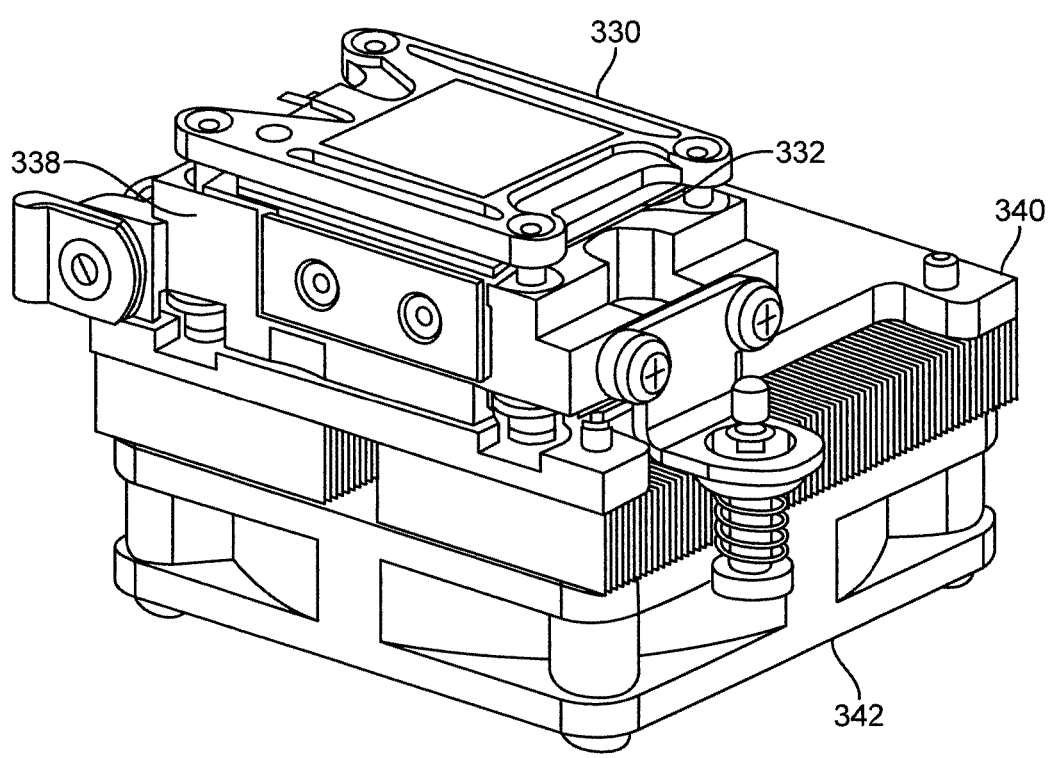

Turning now to FIGS. 26*a-c*, each of the first, second and third thermal stacks 287*a-c* comprises a spreader plate 330, a reservoir block 338, a heat sink 340, and a fan 342. A peltier device 332 having a first side 334 and a second side 336 is provided between the spreader plate 330 and the reservoir block 332. The first side 334 of the peltier device 332 is in thermal contact with the spreader plate 330 whilst the second side 336 of the peltier device is in thermal contact with the reservoir block 338. This peltier device is typically a Marlow device, optimised for high power and thermocycling purposes.

One or more temperature sensors (not shown) are mounted in the spreader plate 330 and the reservoir block 338. Typically, a temperature sensor is embedded in a machined recess provided in each of the spreader plate 330 and the reservoir block 338, and set in an epoxy resin. However, a skilled person will recognise that more than one temperature sensor may be provided in each spreader plate 330 and each reservoir block 338. Typically, the reservoir block 338 is formed of aluminium, whilst the heat sink 340 is formed of copper, although a skilled person will recognise that other thermally conductive materials may be used.

In the exemplary reader, first and third thermal stacks 287*a*, 287*c* are designed to provide a static controlled temperature, whilst the second stack 287*b* is designed to change the surface temperature of the second heater as quickly as possible. This is achieved by modifying the spreader plate 330*b* of the second stack 287*b* to minimise its mass.

Figure 27:
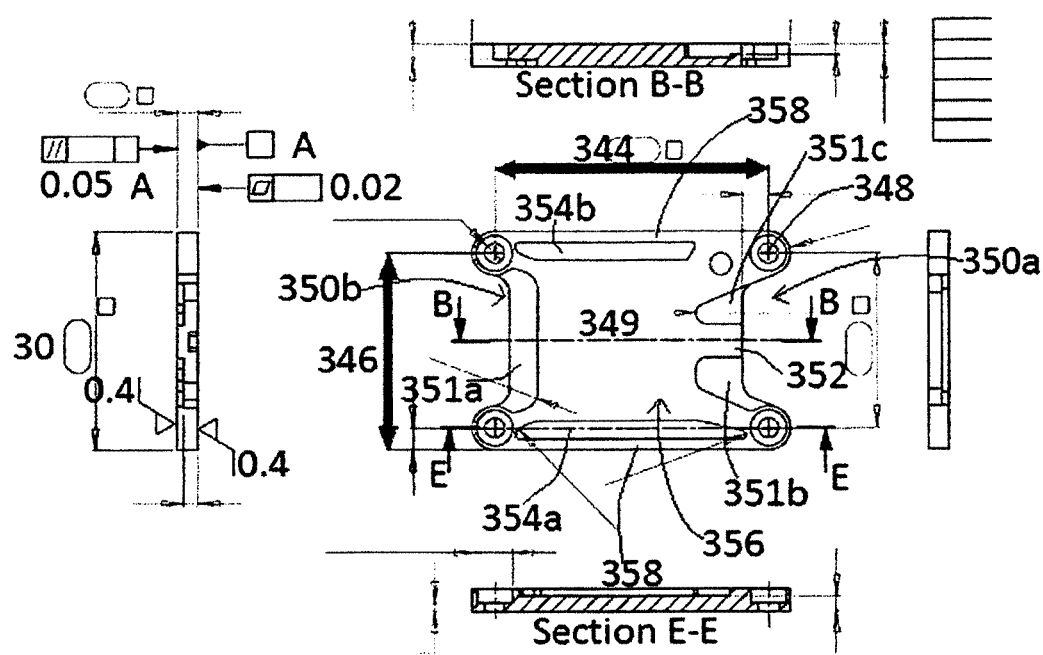
FIG. 27 shows an aluminium spreader plate provided in the thermal stack of FIG. 26.

FIG. 27 shows the spreader plate 330*b* of the second thermal stack 287*b* in more detail. The spreader plate 330*b* has a first face 356 and a second face (not shown), and is preferably comprised of aluminium. The first face 356 comprises a substantially planar central portion 349 for contacting the fluidic foil of the exemplary cartridge whilst the second face comprises a substantially planar central portion for contacting the first side 334 of the peltier device 332. As shown in FIG. 27, the spreader plate 330*b* has a substantially rectangular footprint having a long side 344 along its length and a short side 346 along its width. Fixation points 348 are provided at each corner of the spreader plate 330*b*. Preferably, fixation points 348 are recessed apertures through which a screw may be inserted.

The spreader plate 330*b* has first and second cut-outs 350*a-b* extending along each of its short sides between adjacent fixation points 348. At the periphery of each of its short sides 346, the spreader plate 330*b* comprises at least one area of reduced thickness 351*a-c*. In the exemplary embodiment shown in FIG. 27, the spreader plate 330*b* comprises a first area of reduced thickness 351*a* along one short side, and two further areas of reduced thickness 351*b-c*, separated by a ridge 352, on the other. One or more areas of reduced thickness 354*a-b* are also provided extending along each of its long sides between adjacent fixation points 348. Preferably, the areas of reduced thickness 354*a-b* extending along each of the long sides are provided as elongated recesses extending along each of the long sides, such that a ridge 358 bounds the outer edge of the long sides 344. However, a skilled person will understand that one or more areas of reduced thickness may be provided extending along each of the long edges of the spreader plate.

Typically, the thickness of the spreader plate 330*b* is approximately 3 mm, except in regions of reduced thickness where the thickness is approximately 1 mm. By reducing the thickness of the spreader plate 330 in at least one of the regions shown in FIG. 27, the mass of the spreader plate can be reduced, whilst maintaining the rigidity required to withstand the clamping forces applied repeatedly throughout multiple test cycles.

The first and third spreader plates 330*a,c* are preferably formed of aluminium and Typically have a larger, simpler shape than the PCR since their performance is less critical and as such is not optimised.

Referring again to FIGS. 26*a-c*, to ensure good thermal contact with the cartridge, each thermal stack is spring mounted with respect to the lower clamp 288. Generally, two springs 360*a-b* are provided either side of each thermal stack 287*a-c*, as shown in FIGS. 26*a-c*. Preferably, each thermal stack 287*a-c* is spring mounted in the lower clamp 288 such that the upper surface of each thermal stack 287*a-c* is approximately 1 mm proud of the lower clamp when the springs 360*a-b* are uncompressed.

At the start of the test, the thermal stacks 287*a-c* are brought into contact with the fluidic foil on the underside of the cartridge 100 inserted into the machine as the lower clamp 288 is moved towards its fully closed position. As the lower clamp 288 moves to its fully closed position, the springs 360*a-b* on which the thermal stacks 287*a-c* are mounted are compressed.

Each of the first, second and third thermal stacks 287*a-c* are applied to the fluidic foil of the cartridge with a different force, depending on the degree of thermal contact required. Typically, the first thermal stack 287*a* is applied to the fluidic foil with a first force, the second first thermal stack 287*b* with a second force and the third thermal stack is applied to the fluidic foil with a third force, wherein the second force is greater than the first force, and the first force is greater than the second force. Ideally, the first thermal stack is applied to the foil with a force of 30N±10N; the second thermal stack is applied to the foil with a force of 45N±10N; and the third thermal stack is applied to the foil with a force of 25N±10N.

The force applied to the fluidic foil by the first, second and third thermal stacks 287*a-c* may be determined by the stiffness of the springs 360*a-b* on which each of the thermal stacks 287*a-c* is mounted in the lower clamp 288. Alternatively, the distance by which each of the stacks protrudes may be varied, such that each of the springs 360*a-c* must be compressed by a different amount.

The surface temperature of each of the thermal stacks 287*a-c* is individually controlled by the thermal board 221, which is mounted directly below the main control board 220. A schematic diagram of the thermal board is shown in FIG. 15. It carries drive circuits for the peltier devices 232*a-c* and the three DC fans. These circuits connect to the peltier devices and fans via the connector board 224.

In use, the surface temperature of each of the first, second and third thermal stacks is monitored by the thermal sensors (not shown) and maintained by the peltier drivers on the thermal board. The temperature sensors are configured to measure a temperature of the surface of each thermal stack 287*a-c*. This information is fed back to the thermal board, which, based on the signal from the temperature sensors at the surface of each of the thermal stacks 287*a-c*, varies the signal supplied by the peltier driver to each of the peltier devices 232*a-c* to achieve a desired temperature at the fluidic foil. As will be understood by the skilled person, the first side of each peltier device may be driven as a cooler or a heater for each portion of the fluidic foil as required.

During a test, the thermal board is typically configured to maintain the first thermal stack at a constant temperature between 35° C. and 40° C., preferably approximately 37° C.

The design of the second thermal stack, including the low mass of the second spreader plate, allows rapid cycling of the sample processing region. Typically, the second thermal stack cycles the temperature of the sample processing region between approximately 65° C. and approximately 95° C. Due to the low mass of the spreader plate 330*b*, a cycle time of between 7 and 8.5 s is possible (cycle=time taken for the surface of the thermal stack to go from 65° C.-95° C., and from 95° C.-65° C.). Preferably, one cycle is 7 s. Typically, 35 to 45 (preferably 40) thermal cycles are completed in a single test sequence. Thereafter, the PCR stack is held at a constant temperature for movement of the sample to the detection chamber.

Preferably, the third thermal stack maintains a surface temperature of approximately 20° C. This prevents the reagents provided in the detection chambers 62*a-d* from overheating. In practice, since the sample processing region is adjacent to the detection chamber and is heated to much higher temperature, the third thermal stack is configured as a cooler for the detection chamber for at least a part of the test cycle.

After a test has been completed, the lower clamp returns to its home position, and the thermal stacks 287*a-c* move out of contact with the fluidic foil once the cartridge has been lowered into the drawer 202. By providing the second thermal stack at the rear of the lower clamp, the second thermal stack (having the highest temperature) is not accessible to the user, even when the drawer is open.

2.6 Blister and Valve Actuation

Figure 29:
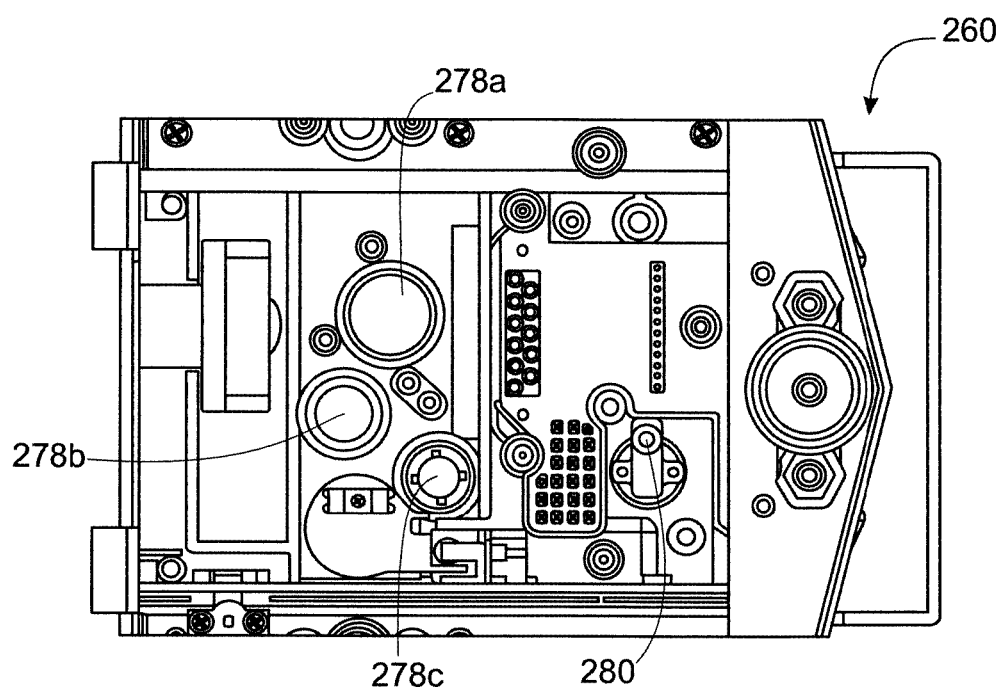
FIG. 29 is a plan view of the upper clamp, comprising first, second and third blister actuators and a mechanical valve actuator.

Referring now to FIG. 29, the upper clamp 260 comprises four mechanical actuators; three mechanical blister actuators 278*a-c* and a mechanical valve actuator 280. Each of the blister actuators comprises a housing 395, a linear actuator (not shown), a stem portion 395, and a tip portion 370. Each of the linear actuators preferably comprises a stepper motor engaged with a splined shaft (for example a Haydon Kerk unit, model no. 25443-05-048) although a skilled person will understand that other linear actuators may be provided.

In the exemplary cartridge, three blisters are provided, containing one each of lysis buffer, wash buffer, and elution buffer. However, a skilled person will recognise that the blister actuators described herein may be implemented with any fluid-filled blister sub-assembly.

Figure 30:
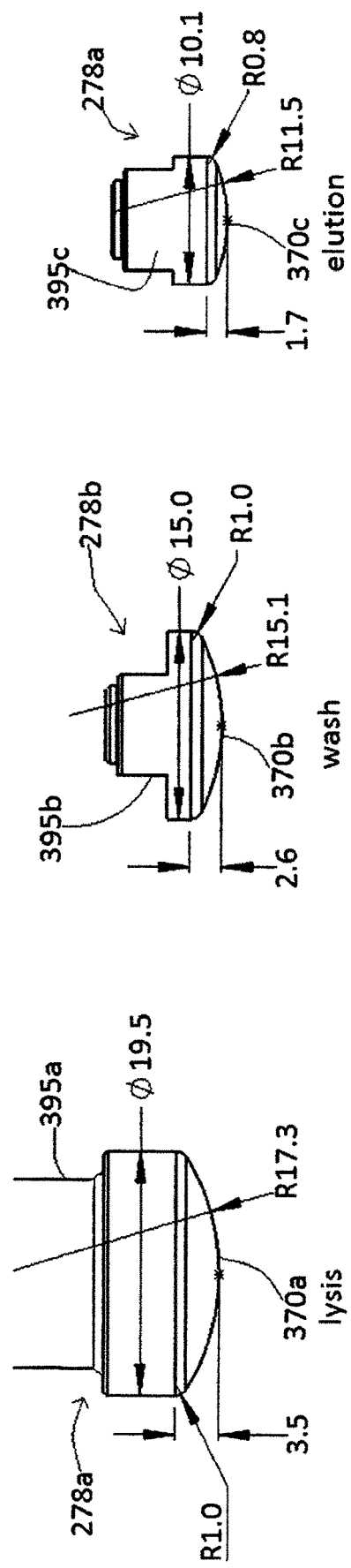
FIG. 30 shows the tip geometries of the first, second and third blister actuators from FIG. 29.

FIG. 30 shows the tip geometries of the first, second and third blister actuators 278*a-c* each comprising stem 395 and a tip 370. Each tip comprises a diameter D, and is dimensioned to align with and collapse a corresponding blister on a cartridge 100 inserted between the upper and lower clamps. Preferably, the actuator tip configured to actuate the lysis blister of the exemplary cartridge has a diameter $D_L$ of approximately 19.5 mm; the blister tip configured to actuate the wash blister has a diameter $D_W$ of 15.0 mm; and the actuator tip configured to actuate the elution blister has a diameter $D_E$ has a diameter of approximately 10.1 mm, although a skilled person will understand that the radius of each actuator tip may be modified reflect the size of the blister to be actuated. A spring 374 (shown in FIG. 20) may be provided between the actuator housing and the blister actuator tips 370.

As shown in FIG. 30, the actuator tip may have a domed actuation surface configured to contact a collapsible blister comprised in the exemplary cartridge. Ideally, the radius of curvature R of the domed surface for the lysis actuator is 17.3 mm, the radius of curvature for the wash actuator is 15.1 mm, and the radius of curvature for the elution actuator is 11.5 mm. In one embodiment, at least one of the first, second and third blister actuators comprise a flat tip for contacting the corresponding blister. By providing a blister actuator having a substantially flat tip, the reader can expel substantially all of the fluid contained in the collapsible blister.

In use, the reader is configured to actuate the lysis blister, then the wash blister and then the elution blister. In order to actuate each blister, the reader moves the actuator from a first position in which the actuator tip is spaced apart from the blister beneath it, to a second position, in which the blister actuator has entirely collapsed the collapsible blister and expelled the contents into the cartridge. Preferably, the reader holds the blisters actuators 278a-c in their second position for a time T after the blister has been collapsed, thereby preventing the expelled contents of the blister from re-entering the blister chamber. Preferably, time T is at least 5 s, more preferably at least 7 s and more preferably approximately 10 s. Preferably, the distance travelled by each actuator tip is at least 30 mm, more preferably at least 40 mm and more preferably approximately 44 mm. Preferably, the reader maintains the each blister actuator in its fully actuated position. Furthermore, each of the linear actuators are configured so that it is impossible to back-drive the tips, thereby preventing the blister contents re-entering the blister after actuation. An example of a suitable linear actuator that cannot be back-driven may be a Haydon Kerk unit, model no. 25443-05-048.

Figure 31A:
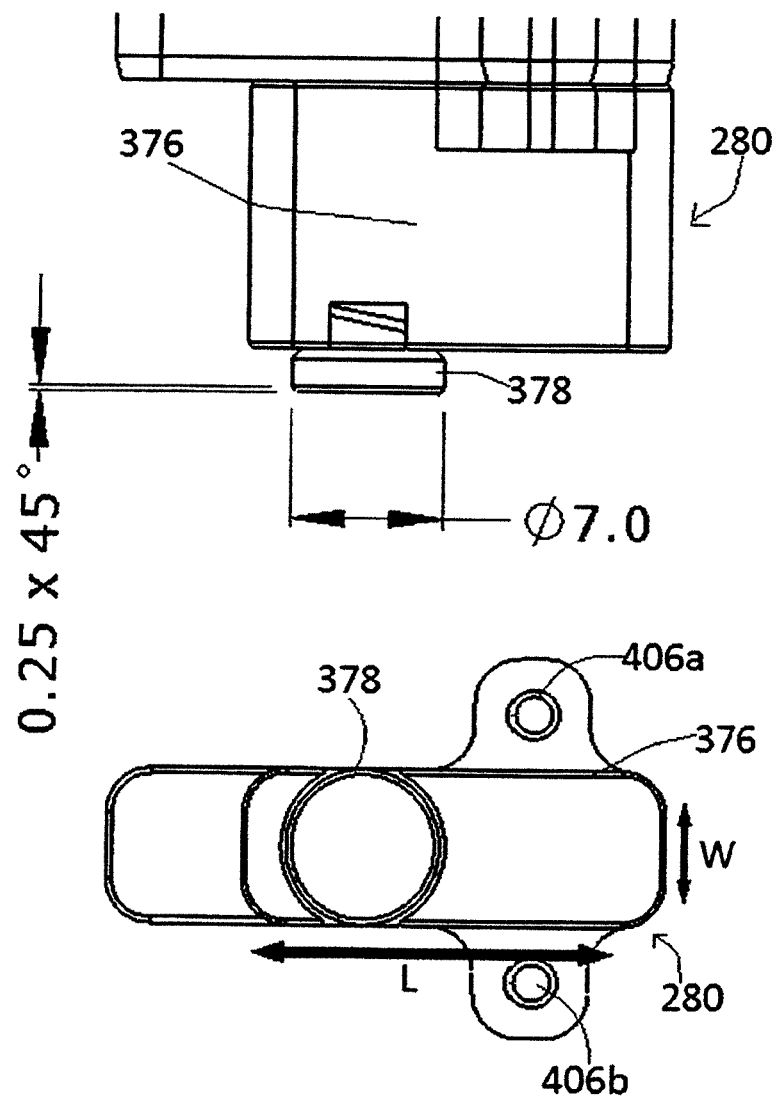
FIG. 31a shows the tip geometry of the mechanical actuator from FIG. 29.
Figure 31B:
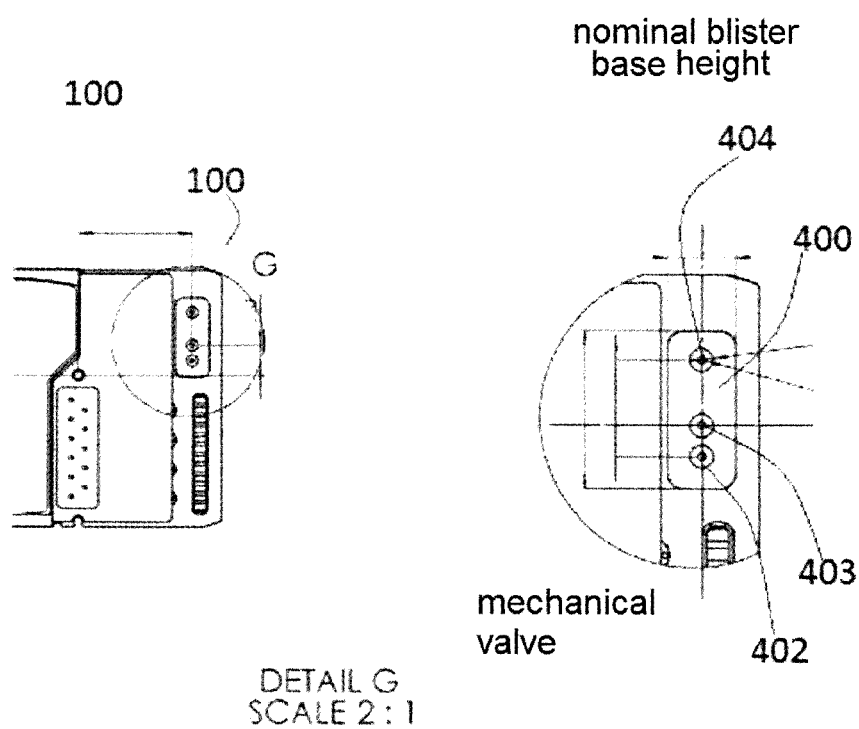
FIG. 31b shows the valve cavity of a mechanical valve comprised in an exemplary cartridge.
Figure 32:
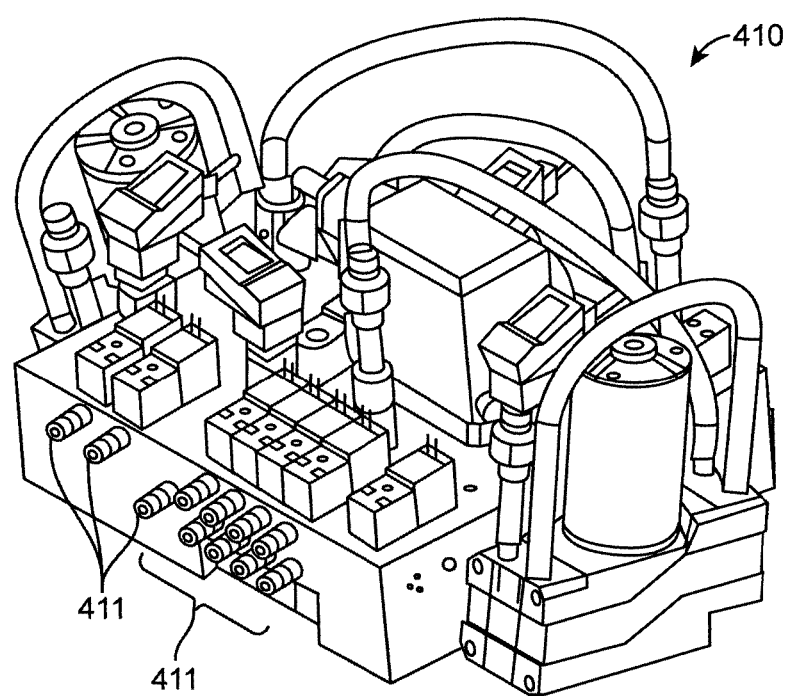
FIG. 32 is a perspective view of a pneumatics block comprised in the reader.
Figure 33:
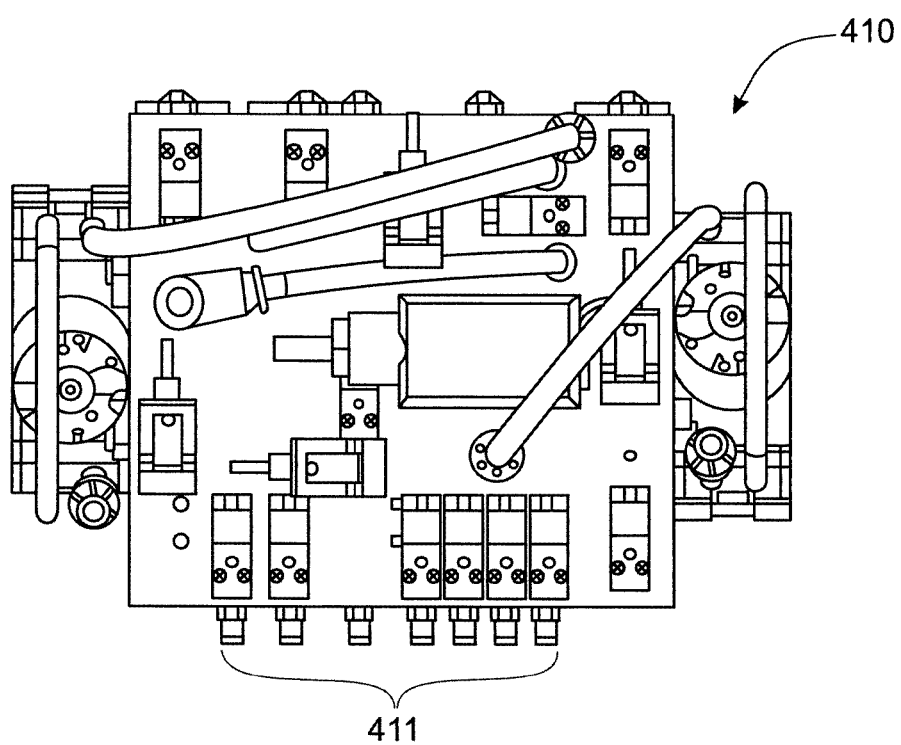
FIG. 33 is a top view of the pneumatics block of FIG. 32.
Figure 34:
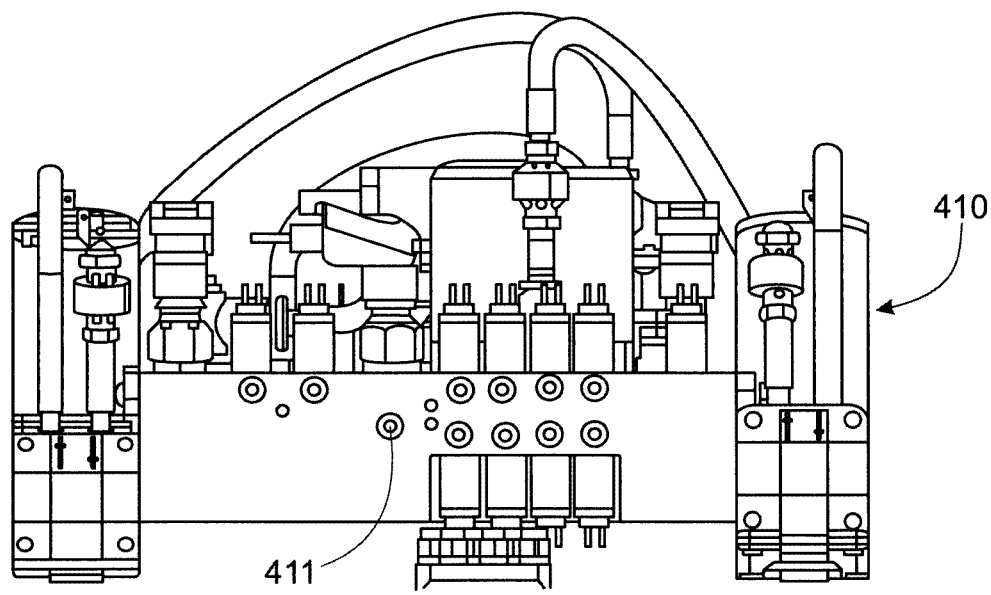
FIG. 34 is a side view of the pneumatics block of FIG. 32.

Referring now to FIGS. 31a-b, the upper clamp further comprises a mechanical valve actuator 280. The mechanical valve actuator 280 aligns with and is configured to actuate a mechanical valve comprised in a cartridge 100 inserted into the reader.

As shown in FIG. 31b, the mechanical valve comprised in the exemplary cartridge preferably comprises a valve chamber 400, containing first and second valve seats. The first valve seat comprises a first opening 402, whilst the second valve seat comprises second and third openings 403, 404. The first opening is spaced apart from the second opening by a distance a, and the second opening is spaced apart from the third opening by a distance b, wherein a>b. A valve membrane seals the valve chamber, and comprises a first portion, for sealing against first opening in the first valve seat, and a second portion, for sealing against the second and third openings in the second valve seat.

FIG. 31a shows the mechanical valve actuator 280 in more detail. The mechanical valve actuator comprises a first actuation portion 376, a second actuation portion 378. The first actuation portion comprises a substantially oblong body having a first substantially planar portion 380 for contacting the first valve membrane portion. The substantially planar portion 380 comprises a length L and a width W, wherein the length is longer than the width. Typically, the first actuation portion 376 is dimensioned to fit within the valve cavity comprised in the exemplary cartridge, and has a complementary footprint, with rounded corners, which covers substantially all of the valve membrane. The second actuator portion 378 comprises a substantially cylindrical body, having a second substantially planar portion 382 for contacting the second valve membrane portion, and is provided on the first planar portion 380 of the first actuation member. A diameter D of the second portion is equal to or less than the width W. Preferably D=W=7 mm. The second actuator portion 378 is provided towards one end of the length L, and is movably mounted relative to the first actuator portion 376 and biased by a spring 277 away from the first portion, towards a cartridge clamped between the upper and lower clamps. The substantially oblong body of the first actuation portion comprises a recess into which the second actuation portion fits such that when the spring 277 is compressed, the lower surfaces of the first and second actuation portions are flush. Optionally, fixation means 406a-b may be provided on each of the long sides.

The reader is configured to actuate the mechanical valve in two stages, of a continuous movement, the first actuator portion sealing the first portion of the valve membrane against the first opening, whilst the second portion of the actuator seals the second portion of the valve membrane against the second and third openings.

In use, the reader closes the mechanical valve by sealing the second and third openings, then sealing the first opening. The reverse is true when the valve opens—the first valve opening is opened, then the second and third valve openings are opened.

To close the valve, the reader moves the first actuator portion towards a clamped cartridge, thereby bringing the second actuator portion into contact with the second portion of the valve membrane. The second actuator portion deforms the second valve membrane portion, and seals it against the second and third openings. At this point, the first actuator portion is spaced apart from the first valve membrane portion.

As the actuator continues to move the first actuator towards the cartridge the spring 377 is compressed between the second actuator portion and the first actuator portion. As the first actuator portion continues to move towards the clamped cartridge, the first actuator portion contacts the first portion of the valve membrane, eventually deforming the valve membrane and sealing it against the first opening.

To open the valve, the reader moves the first actuator portion towards the upper clamp, away from the clamped cartridge. In doing so, the first actuator portion moves to a position in which it no longer seals the first valve membrane portion against the first opening, whilst the second actuator portion maintains the seal over the second and third openings under the influence of the spring 377. As the first actuator portion moves further from the cartridge, the spring 377 reaches its full extension and the second actuator portion is moved away from the second valve membrane portion, thereby opening the second and third openings.

The mechanical valve actuator 280 may also be used in combination with the isolation valve actuator to depressurise the back end of the cartridge once a test has been completed. In order to depressurise the back end of the cartridge, the reader seals the first portion of the valve membrane against the first and second valve seats, and then seals the second valve membrane portion against the third valve seat. At the end of the test, reader actuates the isolation valve actuator, and closes the isolation valve in the fluidic cartridge as described above. In closing the isolation valve, the reader creates a closed system within the back end of the cartridge. Following actuation of the isolation valve, the actuation valve is opened, as described above, thereby increasing the volume of the closed system sealed by the isolation valve.

2.7 Pneumatics

The pneumatics system will now be described with reference to FIGS. 32 to 38. The system comprises a pneumatics block situated within the cartridge reader housing, connected to a pneumatics manifold which includes eleven pneumatic ports that form a pneumatics interface that connects to a pneumatics interface on a cartridge inserted into the reader.

FIGS. 32 to 37 show the pneumatics block 410, which is constructed from machined aluminium and associated components. The pneumatics block comprises all components necessary to generate a positive pressure and a negative pressure for use in controlling bellows and valves using 'pneumatic logic' (explained further below), a reference pressure, or a positive 'blower' pressure for evacuating a channel in the cartridge. These components include, among others, a pump for generating positive pressure (henceforth a pressure pump); a pump for generating negative pressure (henceforth a vacuum pump); three pressure reservoirs— two positive pressure reservoirs and one negative pressure reservoir; and a plurality of solenoid valves, each of which couples one pneumatic port to one or more pressure reservoirs.

Figure 35:
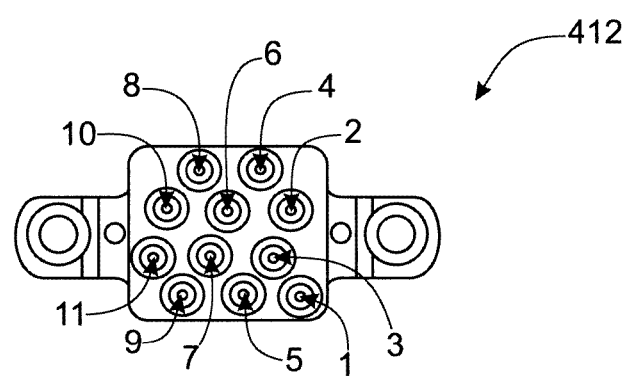
FIG. 35 shows an interface on the manifold to which the pneumatic pipes from the pneumatic block are connected.
Figure 36:
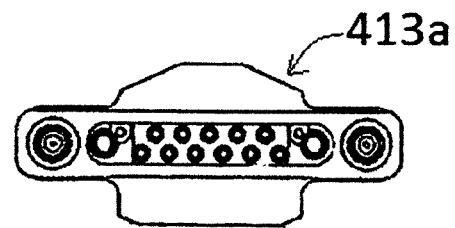
FIG. 36 shows an interface on the manifold which is configured to couple to a corresponding interface on the cartridge.

Provided on the pneumatic block are eleven pneumatics ports 411 which connect to pneumatic tubes, which in turn connect to the pneumatics manifold. FIG. 35 show an interface 412 on the manifold to which the pneumatic pipes from the pneumatic block are connected. FIG. 36 shows an interface 413a on the manifold which is configured to couple to a corresponding interface 413b on the cartridge.

As shown in FIG. 36, the pneumatic ports on the pneumatics manifold are arranged in two rows of 5 ports and 4 ports, respectively. The ports are offset from each other such that a port in one of the rows is aligned equidistantly between two ports of the other. The ports are numbered, and port number 1 is located at one end of the row of 5 ports. Each subsequent port number is adjacent the previous port but on the other row. Thus, the row of 5 ports contains odd-numbered ports (numbers 1, 3, 5, 7, 9 and 11); whereas the row of 4 ports contains even-numbered ports (numbers 2, 4, 6, 8 and 10). The numbering of the ports will be explained in more detail below.

Figure 37:
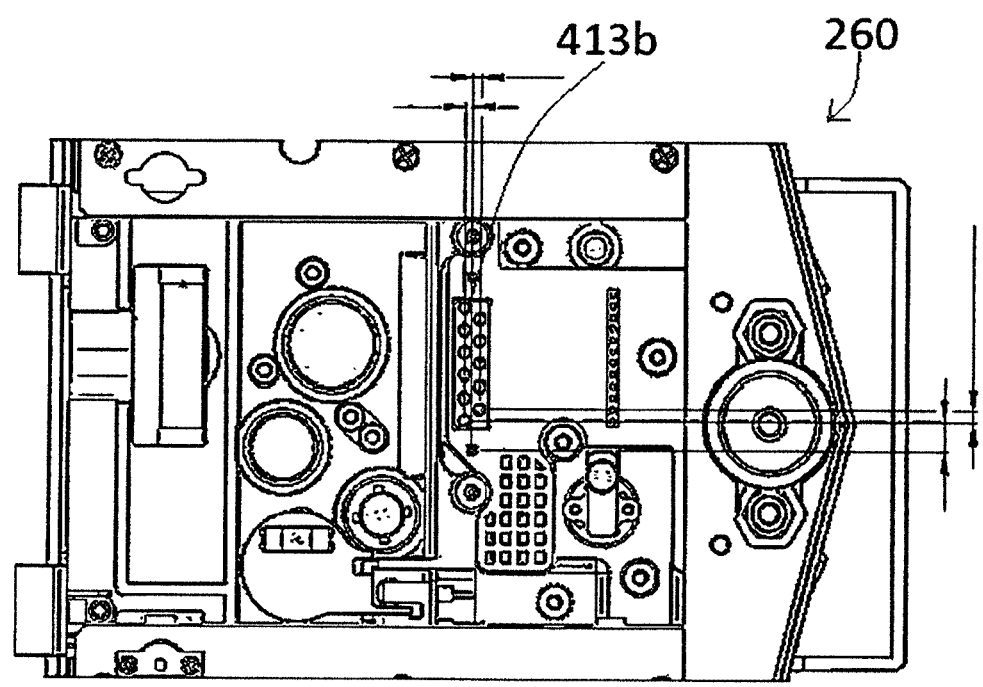
FIG. 37 shows the pneumatic interface located on the upper clamp.

FIG. 37 shows the pneumatic interface located on the upper clamp.

Figure 38I:
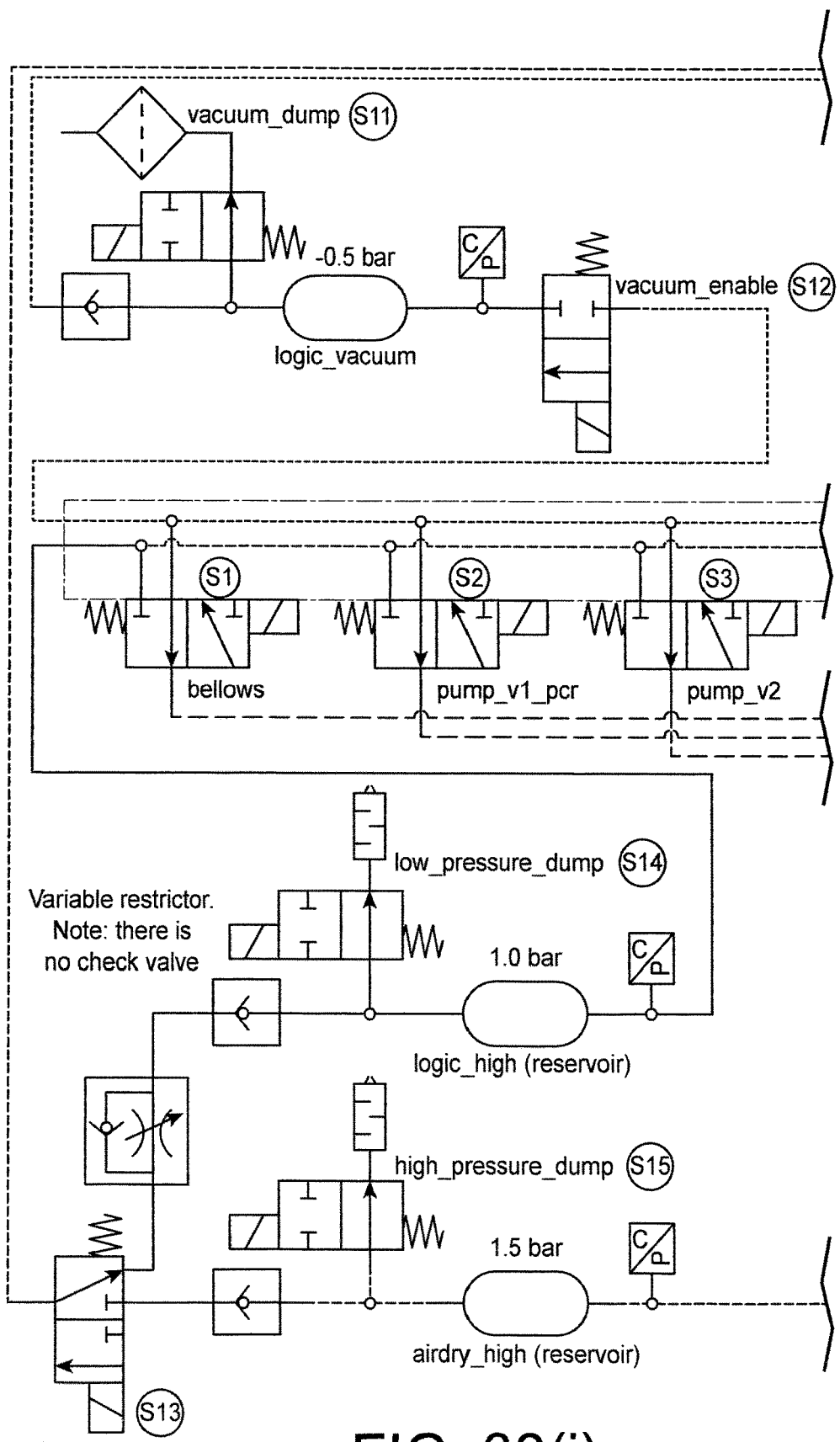
FIG. 38 shows a pneumatic circuit diagram for the pneumatic block.

FIG. 38 shows a pneumatic circuit diagram for the pneumatic block. The circuit comprises a positive pressure sub-system and a negative pressure sub-system. Each of the eleven pneumatic ports is coupled to a solenoid valve, of which eight are '3-port; 2-position' solenoid valves that are coupled to supply lines of the positive pressure sub-system and the negative pressure sub-system (henceforth, the 'pneumatic logic' solenoid valves); of which a further two are '2-port; 2-position' solenoid valves that are coupled to a supply line of the positive pressure sub-system only (henceforth, the 'blower' solenoid valves); and a final one is a '3-port; 2-position' solenoid valves that is coupled to a supply line of the positive pressure sub-system only (henceforth the 'reference-pressure' solenoid valve).

The negative pressure subsystem comprises a vacuum pump coupled to a vacuum reservoir. The pump is configured to maintain a gauge pressure of −0.5 barg in the vacuum reservoir. The vacuum reservoir is coupled to a '2-port; 2-position' solenoid valve which controls whether or not vacuum may be applied to a supply line to which the eight 'pneumatic logic' solenoid valves are each coupled.

The positive pressure subsystem comprises a pressure pump coupled to first and second pressure reservoirs. The pump is configured to maintain a gauge pressure of 1 barg in the first pressure reservoir and to maintain a gauge pressure of 1.5 barg in the second pressure reservoir. A '2-port; 2-position' solenoid valve selectively couples the pump to the first and second pressure reservoirs. The first pressure reservoir applies pressure to a first supply line to which the eight 'pneumatic logic' solenoid valves are each coupled.

The eight 'pneumatic logic' solenoid valves each have an output port coupled to a pneumatic interface port, and first and second input ports. By default (i.e. in their normal, unactuated positions) the valves are configured to couple the first input port to the output port, and must be actuated in order to couple the second input port to the output port. The supply line of the negative pressure sub-assembly is coupled to the first input ports of the eight 'pneumatic logic' solenoid valves, whereas the first supply line of the positive pressure sub-assembly is coupled to the second input ports. Thus, by default (and assuming the '2-port; 2-position' solenoid valve of the negative pressure sub-assembly is open), the eight 'pneumatic logic' solenoid valves allow a negative pressure to be applied to their corresponding pneumatic interface ports. When individually or collectively actuated, the eight 'pneumatic logic' solenoid valves allow a positive pressure to be applied to their corresponding pneumatic interface ports.

The second pressure reservoir applies pressure to a second supply line to which the two 'blower' solenoid valves and the 'reference-pressure' solenoid valve are each coupled. More specifically, the second supply line branches into first a second branches, the first of which is coupled to the two 'blower' solenoid valves. The second branch of the second supply line is coupled to the 'reference-pressure' solenoid valve via a pressure regulator.

The two 'blower' solenoid valves each have an output port coupled to a pneumatic interface port, and an input port coupled to the second pressure reservoir. By default (i.e. in their normal, unactuated positions) the valves are closed, such that the input port is disconnected from the output port. When actuated, the two 'blower' solenoid valves allow a positive pressure to be applied to their corresponding pneumatic interface ports. The second pressure reservoir is configured to supply a flow rate of at least 1.5 litres per minute at 1 barg for this purpose.

The 'reference-pressure' solenoid valve has an output port coupled to a pneumatic interface port, and first and second input ports. By default (i.e. in their normal, unactuated positions) the valves are configured to couple the first input port to the output port, and must be actuated in order to couple the second input port to the output port. The first input port is a channel connected to a further 'vent' solenoid valve that is normally closed but nay be opened to atmosphere, whereas the second input port is coupled to the second pressure reservoir via the pressure regulator. Thus, by default, the 'reference pressure' solenoid valve seals the corresponding pneumatic interface port. When the 'vent' solenoid is actuated, the pneumatic interface is connected to atmosphere. When the 'reference pressure' solenoid valve is actuated, it allows a regulated pressure to be applied to the corresponding pneumatic interface port.

A controller on the main board controls the actuation of the pressure pump, the vacuum pump and all solenoid valves. Thus, during a test, the controller may operate the pumps and valves according to a predetermined cycle.

The pneumatics system performs 4 basic functions on a fluidic cartridge. The first is to operate the bellows that pumps the fluid sample around the cartridge; the second is to operate the various pneumatic valves located in the cartridge; the third is to evacuate channels in the cartridge; and the fourth is to provide a reference pressure.

Operation of the bellows and valves is performed by the eight 'pneumatic logic' solenoid valves. The valves are capable of applying either a positive pressure (of 1 barg) or a negative pressure (of −0.5 barg) to each pneumatic port coupled to those valves. The valves and bellows of the cartridge are open when a negative pressure is applied and closed when a positive pressure is applied. Thus, the bellows and pneumatic valves of a cartridge may be controlled.

The operation of the bellows will be described by way of example. A valve is placed either side of the bellows. Air is drawn in to the bellows by opening the bellows (applying a negative pressure) whilst the upstream valve is open (applying a negative pressure) and the downstream valve is closed (applying a positive pressure). Then, the upstream valve is closed (applying a positive pressure) and air is expelled from the bellows by closing the bellows (applying a positive pressure) whilst the downstream valve is open (applying a negative pressure). This cycle repeats to pump a fluid downstream.

Evacuation of channels in the cartridge is performed by the two 'blower' solenoid valves. These valves are capable of applying a positive pressure of 1.5 barg, and achieve a flow rate of at least 1.5 litres per minute at a pressure of 1 barg. Each valve evacuates and dries a different section of channels of the cartridge.

It will be appreciated that in order to evacuate and dry the channels of the cartridge, it is necessary to open pneumatic valves. Since the reader is able to apply a negative pressure and a positive pressure simultaneously (owing to the two pumps), it is possible to open the requisite pneumatic valves on the cartridge by operating the appropriate 'pneumatic logic' solenoid valves accordingly, and then evacuate the channels of the cartridge by operating the 'blower' solenoid valves accordingly.

In the preferred case (corresponding to the exemplary cartridge described above), pneumatic interface port numbers 1 to 4, 6, 8, 10 and 11 are coupled to 'pneumatic logic' solenoid valves; pneumatic interface port numbers 5 and 7 are coupled to 'blower' solenoid valves and pneumatic interface port number 9 is coupled to the reference-pressure solenoid valve.

Between each of the two 'blower' solenoid valves and the 'reference-pressure' solenoid valves and their respective pneumatic interface ports there is provided a fluid trap for capturing any fluid that flows from the cartridge into the reader, thus preventing such fluid from damaging the reader.

Each pneumatic interface port shall be not less than 3 mm in diameter, and the pneumatic interface of the exemplary cartridge shall be configured to receive pneumatic interface ports that are not less than 3mm in diameter.

2.8 Improved Arrangement of Electrodes and Cartridge Reader

As discussed above, the reader comprises an electrical interface, comprised in the upper clamp and configured to contact the electrodes comprised in the cartridge.

Conventionally, the counter electrode in a potentiostat is larger than the working electrode to provide an ample supply of surplus electrons. However, it has been found that reversing this convention surprisingly offers better results for the exemplary cartridge. For the electrochemistry performed on the liquid sample described above in the exemplary cartridge, it is found that having a working electrode which is larger than the counter electrode provides larger signals and improved results by way of increased sensitivity. In other words, having a current flow from a relatively large working electrode to a relatively small counter electrode offers improvements over the conventional arrangement. The improvement is particularly effective for detecting labels comprising modified Ferrocene Carboxylic Acids in aqueous buffers.

Referring to FIG. 10, preferably each working electrodes 169*a-d* is formed in a U-shape and each counter electrode 170*a-d* is formed in a straight elongate shape between the two prongs of the respective U-shaped working electrode.

In FIG. 10, each of the working electrodes 169*a-d* has a total length of 8.1 mm. Each electrode is made up of a short prong 174*a-d* of length 5.1 mm, connected to an interconnecting portion 176*a-d* of length 1.3 mm oriented at 90° to the short prong 174*a-d*, connected to a long prong 178*a-d* of length 8.1 mm oriented at 90° to the interconnecting portion 176*a-d* and parallel to and adjacent with the short prong 174*a-d*. The width of the working electrodes is 0.74 mm along its length, which provides a total surface area of 10.2 mm$^2$.

Each of the counter electrodes 170*a-d* is made up of an elongate portion of length 7.2 mm and width 0.35 mm, which provides a total surface area of 2.5 mm. Thus, the ratio of surface area of the counter electrode to the surface area of the working electrode is 1:4. This ratio has been found to be particularly effective at providing larger signals that can be measured effectively because of the increased sensitivity.

As shown in FIG. 10, each electrode in the set of electrodes is connected to an electrical contact for electrically connecting to a corresponding electrical contact in a cartridge reader. For instance, each working electrode 169*a-d* is connected to an electrical contact 180*a-d*; each counter electrode 170*a-d* is connected to an electrical contact 184*a-d;* and each reference electrode 171*a-d* is connected to an electrical contact 182*a-d*. For a cartridge having four detection chambers, there are 12 electrical contacts 180*a-d,* 182*a-d,* 184*a-d*.

Figure 39:
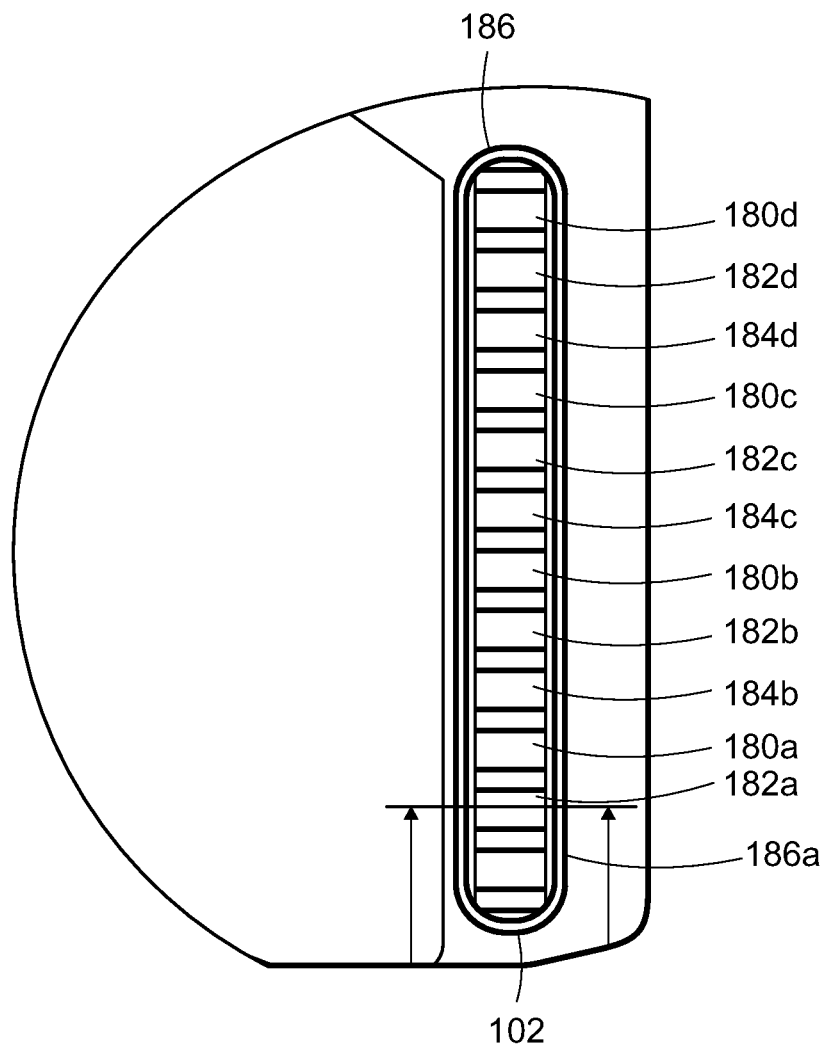
FIG. 39 shows a portion of the housing of the exemplary cartridge in which the invention is implemented.

FIG. 39 shows a portion of the housing of the exemplary cartridge in which the invention is implemented. Visible in the figure is the electrical interface 102 shown in FIG. 39. The electrical interface comprises the 12 electrical contacts 180*a-d,* 182*a-d,* 184*a-d* which are accessible through an elongate aperture 186 in the housing, thereby providing a contact area on each electrical contact 180*a-d,* 182*a-d,* 184*a-d* for electrically connecting to a corresponding electrical contact on the reader. As shown, each electrical contact presents a contact area of 2.7 mm by 1.5 mm. It is possible to provide smaller or larger contact areas for each electrical contact, for instance the contact areas may each be at least 0.5 mm by 0.5 mm; preferably at least 1 mm by 0.5 mm; more preferably at least 2 mm by 1 mm, more preferably at least 2.7 mm by 1.5 mm.

A reader into which the exemplary cartridge is inserted in order to perform a test comprises a control module and an electronics interface (not shown) having 12 electrical contacts corresponding to the 12 electrical contacts on the cartridge. The electrical contacts of the reader take the form of 12 pins which are sprung so as to be biased toward a cartridge inserted into the reader. When a cartridge is inserted into the reader and the pins contact the electrical contacts of the cartridge, the pins apply a spring force of between 300 and 900 mN (per pin) against the electrical contacts. The pins are gold plated to provide optical electrical connectivity between the cartridge and the reader.

To carry out an electrochemical test on a sample in the cartridge, the control module and electronic interface of the reader apply a potential difference across the pins which contact the counter, references and working electrodes of the cartridge (180a-d; 184a-d). The current flowing between these electrodes is then measured. A suitable circuit for applying this potential difference and measuring the resulting current is shown in FIG. 10, together with a diagrammatic representation of what is taking place in the circuit. In summary, a signal generator in the control module and electronic interface of the reader applies a potential difference ($V_{applied}$), corrected for activity on the reference electrode, across the working and counter electrodes, and the resulting current flowing from the working electrode to the counter electrode is measured by a current measuring means I. In a given test carried out by the reader, the potential difference applied across the pins which contact the counter electrodes and working electrodes of the cartridge (180a-d; 184a-d) varies according to a voltage sweep, as described below.

Figure 40:
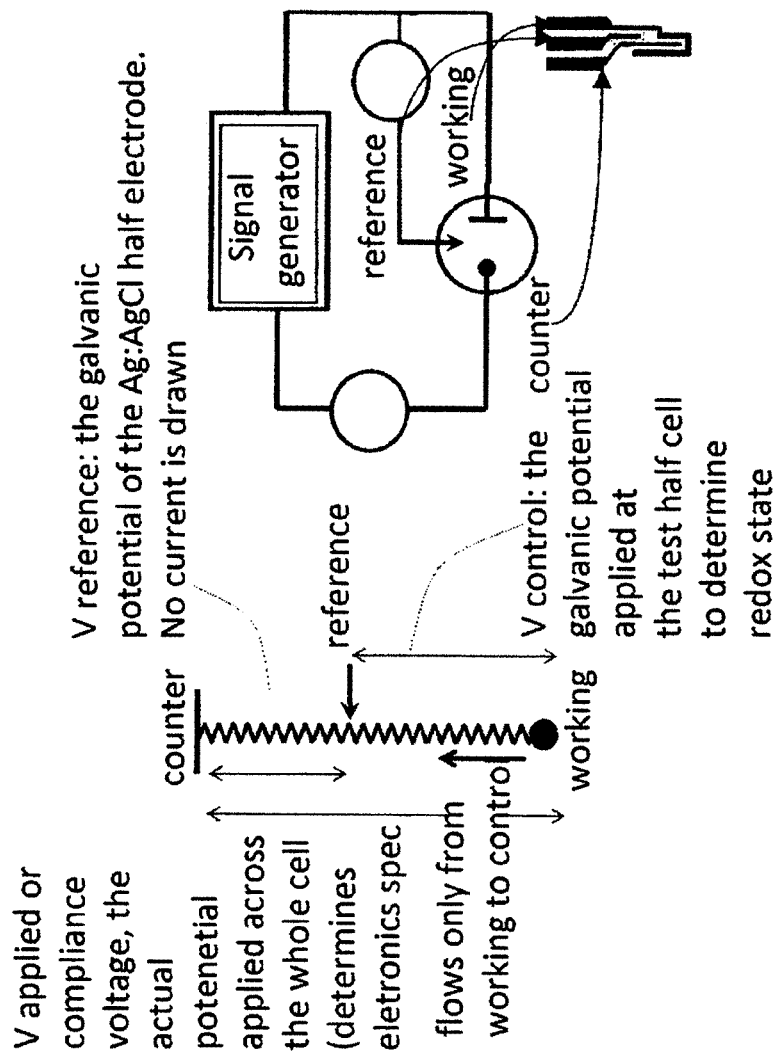
FIG. 40 shows an exemplary circuit containing the electrodes.

The pins in the reader which contact the reference electrodes of the cartridge (182a-d) are coupled to a voltage measuring means V. The circuit shown in FIG. 40 is thus able to measure the voltage between the reference electrode and the working electrode ($V_{control}$) and the voltage between the reference electrode and the counter electrode ($V_{reference}$). The reference electrode is used as a reference such that all other voltages are declared with respect to this reference electrode, and therefore pertain to the activity of the working electrode only. This is because the voltage of the reference electrode is largely independent of the redox conditions and therefore means that it is only the redox state of the chemistry at the working electrode that is being measured.

The control module and electronic interface of the reader are configured to conduct a test using differential pulse voltammetry or square wave pulse voltammetry.

Figure 41:
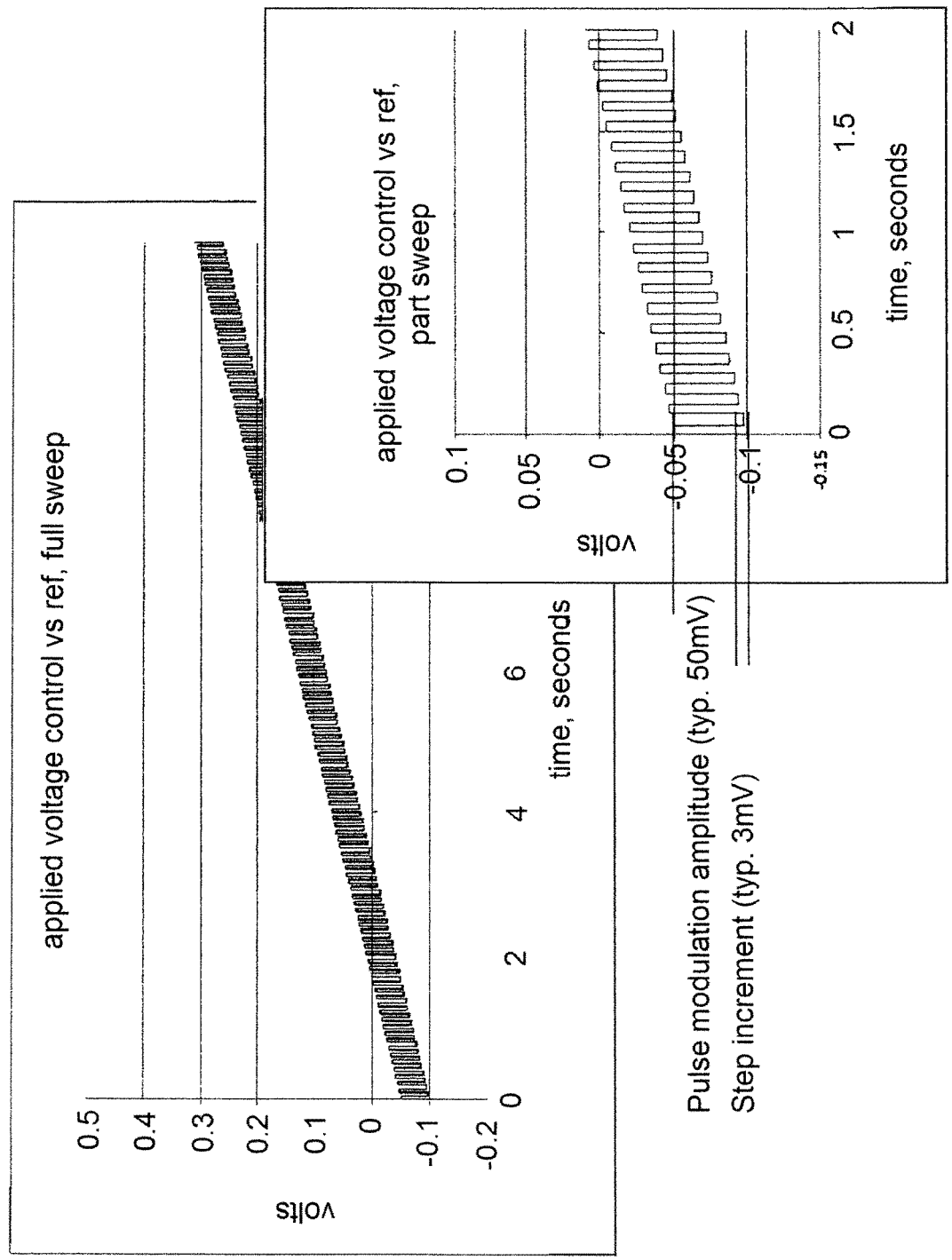
FIG. 41 shows the results of a test using differential pulse voltammetry or square wave pulse voltammetry.

A first exemplary test using differential pulse voltammetry will now be described with reference to FIG. 41.

In the first exemplary test, a slowly incrementing voltage sweep is applied across the working and control electrodes (i.e. $V_{applied}$) with a relatively large step pulse overlaid at the start of each increment. The full sweep is from around −0.7 volts to +1 volts relative to reference electrode. This range is within the practical half-cell ranges limited by partial hydrolysis of water and degradation of DNA molecules themselves.

Each pulse has a magnitude of 50 mV and the sweep increases by a step increment of 3 mV per pulse. The duration of the test may be shortened by increasing the step increment, but this leads to coarser results. Accordingly, a step increment of between 1 mV and 5 mV is preferred, preferably between 2 mV and 4 mV.

Figure 42:
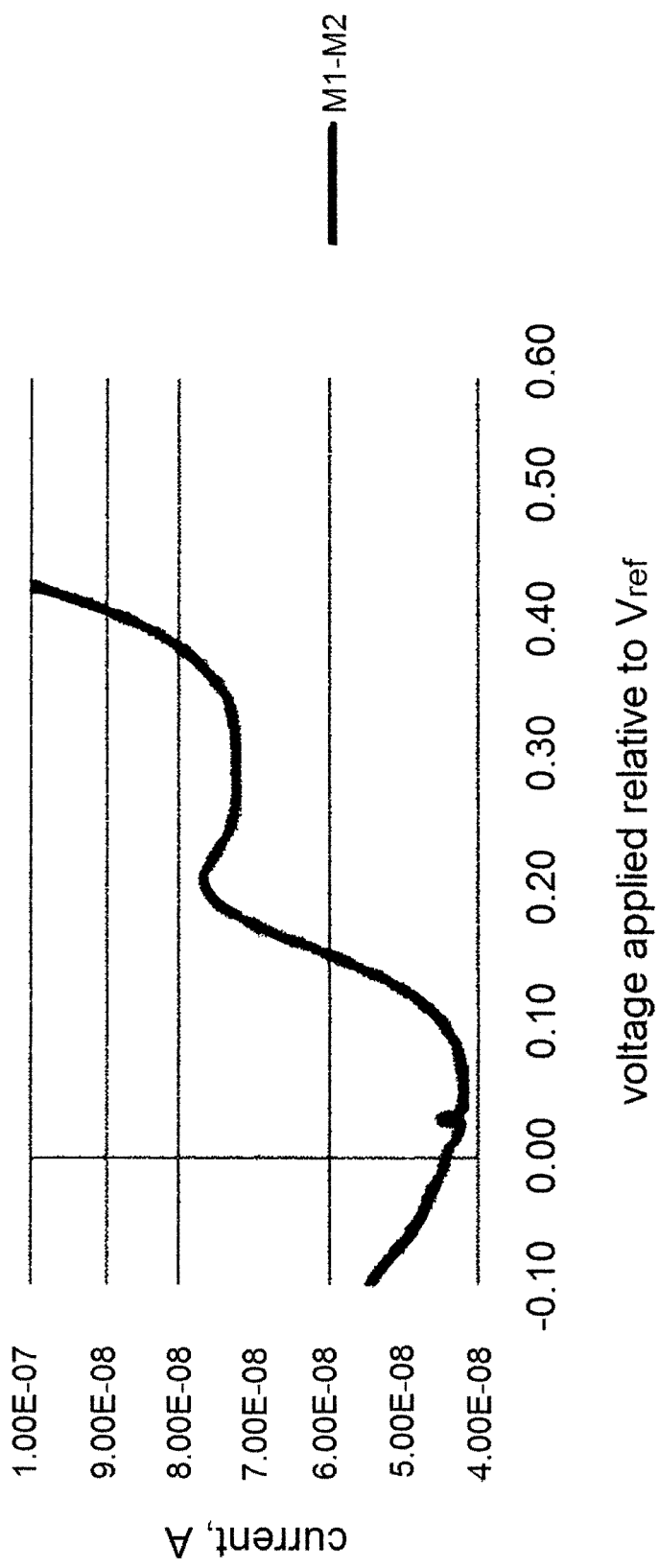
FIG. 42 shows the forward and reverse current for ferrocene in a buffer.

Each pulse causes two different currents to flow through the sample—one during the peak of the pulse and one during the trough of the pulse. The current flowing during the pulse peak is the forward current (M1) and the current flowing during the pulse trough is the reverse current (M2). These currents are measured, and may be plotted against $V_{applied}$ (relative to $V_{reference}$). In particular, the differential current between M1 and M2 may be plotted against $V_{applied}$ (relative to $V_{reference}$), as shown in FIG. 42. From these, a peak differential current associated with electrochemical activity of a label may be identified, providing the signal that is indicative of the labels in the sample.

The skilled person will be capable of modifying the exemplary cartridge to implement the inventive aspects described herein in various ways depending on circumstances. It is intended that the scope of the present invention is defined by the following claims.

The invention claimed is:

1. A cartridge reader for carrying out a diagnostic test on a sample contained in a fluidic cartridge comprising a mechanical valve for isolating the sample with the cartridge, the cartridge reader comprising a system for actuating the mechanical valve comprising:
   an actuation member configured to move the mechanical valve from an open position to a closed position;
   an armature connected to the actuation member, configured to engage an electromagnet, wherein the electromagnet can be switched between an active state in which it electromagnetically holds the armature and an inactive state in which it does not electromagnetically hold the armature;
   a first biasing means, disposed between the actuation member and a bearing surface, wherein the first biasing means is configured to bias the actuation member into a first position in which it actuates a mechanical valve in a fluidic cartridge inserted into the reader;
   wherein the actuation member is held in a second position against the bias of the first biasing means by the electromagnet when the electromagnet is in its active state, and is moved into its first position by the first biasing means when the electromagnet is in its inactive state;
   an upper clamp having a fixed position relative to the cartridge reader and a lower clamp, movable relative to the upper clamp, wherein the upper clamp and the lower clamp are configured to receive the fluidic cartridge therebetween;
   a gantry, fixedly connected to the lower clamp by at least one alignment shaft which passes through at least one aperture in the upper clamp such that at least a portion of the gantry extends above the upper clamp, wherein the electromagnet is connected to the gantry and the bearing surface is comprised in the upper clamp; and
   a processing means for controlling operation of the cartridge reader and configured to determine when a diagnostic test carried out by the reader has been completed, and to switch the electromagnet to its inactive state at the end of the diagnostic test so as to move the mechanical valve from an open position to a closed position to isolate the sample within the cartridge.

2. The cartridge reader of claim 1, wherein, in the event of a fault or power failure, the electromagnet becomes inactive and the mechanical valve moves to its closed position to isolate the sample.

3. The cartridge reader of claim 2, wherein the armature and the actuation member are connected by a shaft which passes through an aperture in the upper clamp.

4. The cartridge of claim 2, wherein the reader is further configured to:
   move the lower clamp from a first position in which the electromagnet mounted on the gantry is spaced apart from the armature when the armature is in its first position, to a second position in which the electromagnet contacts the armature;

activate the electromagnet when it reaches the second position, thereby engaging the electromagnet with the armature; and move the lower clamp from its second position to a third position, whilst magnetically holding the armature, thereby moving the actuation member to its second position.

5. The cartridge of claim 4, further comprising a first coil spring disposed around the at least one alignment shaft, between the actuation member and the upper clamp.

6. The cartridge reader of claim 4, wherein central axes of the electromagnet, the alignment shaft and the actuation member are offset from each other.

7. The cartridge reader of claim 6, wherein the first biasing means comprises a coil spring, and wherein each of the axes is within a circumference of the first biasing means.

8. The cartridge reader of claim 2, further comprising second biasing means between the upper clamp and the gantry.

9. The cartridge reader of claim 8, wherein a force exerted by the second biasing means exceeds the force exerted by the first biasing means.

10. A fluidic cartridge for carrying out a diagnostic test on a sample contained therein, the cartridge comprising a mechanical valve for isolating the sample with the cartridge and configured for use with a cartridge reader of claim 1, the mechanical valve configured to be moved from an open position to a closed position by the actuation member.

\* \* \* \* \*